(12) United States Patent
Bencivenga et al.

(10) Patent No.: US 11,001,580 B2
(45) Date of Patent: May 11, 2021

(54) AMINOTHIAZOLE COMPOUNDS AS C-KIT INHIBITORS

(71) Applicant: Ariad Pharmaceuticals, Inc., Cambridge, MA (US)

(72) Inventors: Nicholas E. Bencivenga, Cambridge, MA (US); David C. Dalgarno, Cambridge, MA (US); Joseph M. Gozgit, Cambridge, MA (US); Wei-Sheng Huang, Cambridge, MA (US); Anna Kohlmann, Cambridge, MA (US); Feng Li, Cambridge, MA (US); Jiwei Qi, Cambridge, MA (US); William C. Shakespeare, Cambridge, MA (US); Ranny M. Thomas, Cambridge, MA (US); Yihan Wang, Cambridge, MA (US); Xiaotian Zhu, Cambridge, MA (US)

(73) Assignee: ARIAD PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/469,517

(22) PCT Filed: Dec. 14, 2017

(86) PCT No.: PCT/US2017/066291
§ 371 (c)(1),
(2) Date: Jun. 13, 2019

(87) PCT Pub. No.: WO2018/112136
PCT Pub. Date: Jun. 21, 2018

(65) Prior Publication Data
US 2019/0352298 A1    Nov. 21, 2019

Related U.S. Application Data

(60) Provisional application No. 62/434,845, filed on Dec. 15, 2016.

(51) Int. Cl.
*C07D 417/14* (2006.01)
*C07D 417/12* (2006.01)

(52) U.S. Cl.
CPC ......... *C07D 417/14* (2013.01); *C07D 417/12* (2013.01)

(58) Field of Classification Search
CPC .................................................. C07D 417/14
See application file for complete search history.

(56) References Cited

U.S. PATENT DOCUMENTS 8,278,307 B2 * 10/2012 Shakespeare ........ C07D 403/12
514/254.05
2009/0149471 A1    6/2009 Shakespeare et al.

FOREIGN PATENT DOCUMENTS

| CN | 102584830 A | 7/2012 |
| WO | 2007/1335626 A2 | 11/2007 |
| WO | WO-2007/133562 A3 | 10/2008 |
| WO | 2012/089106 A1 | 7/2012 |

OTHER PUBLICATIONS

Thomas et al (2011): STN International HCAPLUS database, (Columbus, Ohio), Accession No. 2011: 716237.*
International Search Report for PCT/US2017/066291, 3 pages (dated Feb. 22, 2018).
Mathew Thomas, et al: "Discovery of 5-(arenethynly) Heteromonocyclic Derivatives As Potent Inhibitors of BCRABL Including the T315I Gatekeeper Mutant", Bioorganic & Medicinal Chemistry Letters, Pergamon, Amsterdam, NL, vol. 21, No. 12, Apr. 14, 2011 (Apr. 14, 2011), pp. 3743-3748, XP028387839, ISSN: 0960-894X, DOI: 10.1016/J.BMCL.2011.04.060.

* cited by examiner

Primary Examiner — Golam M Shameem
(74) Attorney, Agent, or Firm — Proskauer Rose LLP; Fangli Chen

(57) ABSTRACT

The invention relates to c-Kit inhibitors useful in the treatment of cancers, and other-threonine kinase mediated diseases, having the Formula: (I) wherein A, L, $R_1$, $R_2$, $R_3$, and n are described herein.

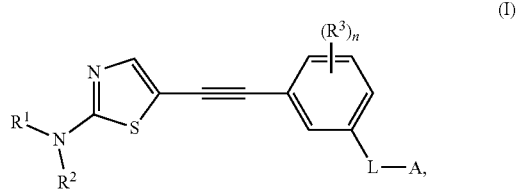

14 Claims, No Drawings

AMINOTHIAZOLE COMPOUNDS AS C-KIT INHIBITORS

CROSS REFERENCE TO RELATED APPLICATIONS

This application is a 35 U.S.C. § 371 National Stage Application of International Application No. PCT/US2017/066291, filed Dec. 14, 2017, which claims priority to U.S. Provisional Patent Application Ser. No. 62/434,845 filed Dec. 15, 2016, the entirety of which is hereby incorporated by reference.

FIELD OF INVENTION

The present invention is directed to inhibitors of tyrosine-protein kinase Kit (c-Kit) useful in the treatment of diseases or disorders associated with c-Kit. Specifically, the invention is concerned with compounds and compositions inhibiting c-Kit, methods of treating diseases or disorders associated with c-Kit, and methods of synthesis of these compounds.

BACKGROUND OF THE INVENTION

The discovery that the tyrosine kinase inhibitor (TKI) imatinib inhibits KIT, and its introduction as a treatment, transformed the clinical management of gastrointestinal stromal tumors (GIST) (Corless, C. L. et al., *Nat. Rev. Cancer* 2011, 11: 865-78). Nonetheless, most imatinib-treated patients ultimately relapse due to outgrowth of clones with secondary, drug-resistant KIT mutations (Heinrich, M. C., et al., *J. Clin. Oncol.* 2006, 24: 4764-74). Secondary mutations typically occur in the ATP binding pocket encoded by exons 13 and 14, and the activation loop (A-loop) encoded by exons 17 and 18. The challenge of treating imatinib resistant GISTs is compounded by mutational heterogeneity, as patients can harbor multiple different secondary mutations in distinct tumor lesions, or even within different regions of the same lesion (Wardelmann E., et al., *Clin. Cancer Res.* 2006, 12: 1743-9).

GIST patients with imatinib-resistant tumors are treated with sunitinib, which potently inhibits KIT ATP-pocket mutants (Heinrich, M. C., et al., J Clin Oncol 2008; 26: 5352-9). However, sunitinib is ineffective against A-loop mutants, which account for 50% of imatinib-resistance mutations. This may explain why overall response rates (ORR) are low (7%) and median progression-free survival (PFS) is short (6.2 months; Demetri, G. D., et al., Lancet 2006; 368: 1329-38). Regorafenib was recently approved as third line therapy, but also shows only moderate activity, with ORR of 4.5% and median PFS of 4.8 months (Demetri, G. D., et al., Lancet 2013; 381: 295-302). The KIT inhibitory properties of regorafenib have not yet been analyzed extensively, but both clinical and initial preclinical data suggest a limited spectrum of sensitive KIT mutants (George, S., et al., *J. Clin. Oncol.* 2012, 30: 2401-7; and Serrano-Garcia, C., et al., *ASCO Meeting Abstracts* 2013; 31 (15_suppl): 10510). Thus, additional agents are needed to overcome resistance mutations in KIT, in particular those in the A-loop.

The KIT inhibitors imatinib, sunitinib and regorafenib are effective GIST therapies, though most patients develop resistance to these drugs due to somatic acquisition of polyclonal secondary KIT mutants. The lack of efficacy of any single agent against the complete set of potential ATP-binding pocket and A-loop secondary mutants makes achievement of prolonged complete disease control in late stage patients challenging. To address this unmet medical need, presented herein are compounds that target a broad range of primary and secondary KIT mutants, including those within the A-loop.

SUMMARY OF THE INVENTION

The present disclosure provides novel aminothiazole compounds and pharmaceutically acceptable salts as effective c-Kit inhibitors.

A first aspect of the invention relates to compounds of Formula (I):

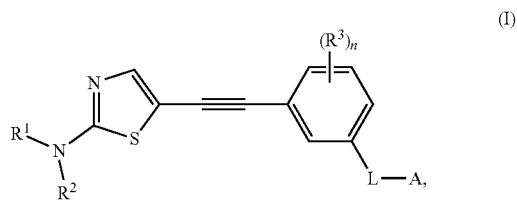

and pharmaceutically acceptable salts, hydrates, solvates, prodrugs, stereoisomers, and tautomers thereof,
wherein:
L is —C(O)NR$^5$— or —NR$^5$C(O)—;
A is (C$_3$-C$_8$) cycloalkyl, (C$_6$-C$_{10}$) aryl, or 5- to 10-membered heteroaryl wherein the cycloalkyl, aryl, or heteroaryl is optionally substituted with one or more R$^4$;
R$^1$ is H, (C$_1$-C$_6$) alkyl, —(CH$_2$)$_q$C(O)OH, or —C(O)N(R$^7$)$_2$;
R$^2$ is (C$_1$-C$_6$) alkyl, —C(O)R$_8$, or —C(O)NR$^9$R$^{10}$;
each R$^3$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, or OH;
each R$^4$ is independently at each occurrence (C$_1$-C$_6$) alkyl, (C$_1$-C$_6$) alkoxy, (C$_1$-C$_6$) haloalkyl, (C$_1$-C$_6$) haloalkoxy, halogen, —OH, CN, —(C(R$^6$)$_2$)$_p$-heterocycloalkyl wherein the heterocycloalkyl comprises a 4- to 7-membered ring and 1 to 3 heteroatoms selected from N, O, and S, or —(C(R$^6$)$_2$)$_p$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from (C$_1$-C$_6$) alkyl, —NH$_2$, (C$_1$-C$_6$) alkylamino, and (C$_1$-C$_6$) dialkylamino;
R$^5$ is H, (C$_1$-C$_6$) alkyl, or (C$_1$-C$_6$) haloalkyl;
each R$^6$ is independently H or (C$_1$-C$_6$) alkyl;
each R$^7$ is independently H or (C$_1$-C$_6$) alkyl;
R$^8$ is (C$_1$-C$_6$) alkyl, (C$_3$-C$_7$) cycloalkyl, (C$_2$-C$_6$) alkenyl, (C$_1$-C$_3$) alkoxy, (C$_1$-C$_6$) haloalkyl, (C$_1$-C$_6$) haloalkoxy, or 4 to 7-membered heterocycloalkyl comprising 1 to 3 heteroatoms selected from N, O, and S;
R$^9$ is H, (C$_1$-C$_6$) alkyl, (C$_1$-C$_6$) haloalkyl, (C$_3$-C$_7$) cycloalkyl, or 4 to 7-membered heterocycloalkyl comprising 1 to 3 heteroatoms selected from N, O, or S;
R$^{10}$ is H, (C$_1$-C$_6$) alkyl, (C$_1$-C$_6$) haloalkyl, (C$_3$-C$_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from (C$_1$-C$_6$) alkyl, —NH$_2$, (C$_1$-C$_6$) alkylamino, (C$_1$-C$_6$) dialkylamino, and —OH, and wherein the (C$_1$-C$_6$) alkyl is optionally substituted with one or more R$^{11}$;
or R$^9$ and R$^{10}$ together with the nitrogen atom to which they are attached form a 4- to 7-membered heterocycloalkyl ring comprising 1 to 3 heteroatom selected from N, O, and S, optionally substituted with one or more substituent each independently selected from $(C_1-C_6)$ alkyl, $(C_1-C_6)$ hydroxyalkyl, $-(CH_2)_q-NH_2$, $-(CH_2)_q-(C_1-C_6)$ alkylamino, $-(CH_2)_q(C_1-C_6)$ dialkylamino, $-C(O)(C_1-C_6)$ alkyl, $-OH$, and 4- to 7-membered heterocycloalkyl comprising 1 to 3 heteroatom selected from N, O, and S, and optionally substituted with one or more $(C_1-C_6)$ alkyl;

$R^{11}$ is $(C_1-C_6)$ alkoxy, $-OH$, $-NH_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and each n, p, and q is independently 0, 1 or 2; and
provided that when A is phenyl and $R_1$ is H, then $R_2$ is not $-C(O)CH_3$.

A second aspect of the invention relates to a method of treating a c-Kit-mediated disease or disorder. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of preventing a c-Kit-mediated disease or disorder. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of inhibiting c-Kit. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a disease or disorder associated with inhibiting c-Kit. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of preventing a disease or disorder associated with inhibiting c-Kit. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with inhibiting c-Kit.

Another aspect of the present invention relates to a compound of Formula (I), or a pharmaceutically acceptable salt, hydrate, solvate, prodrug, stereoisomer, or tautomer thereof, for use in the manufacture of a medicament for preventing a disease associated with inhibiting c-Kit.

Another aspect of the present invention relates to the use of a compound of Formula (I), or a pharmaceutically acceptable salt, hydrate, solvate, prodrug, stereoisomer, or tautomer thereof, in the treatment of a disease associated with inhibiting c-Kit.

Another aspect of the present invention relates to the use of a compound of Formula (I), or a pharmaceutically acceptable salt, hydrate, solvate, prodrug, stereoisomer, or tautomer thereof, in the prevention of a disease associated with inhibiting c-Kit.

The present invention further provides methods of treating or preventing a disease or disorder associated with modulation of c-Kit including, cancer, metastasis, inflammation and auto-immune pathogenesis, comprising administering to a patient suffering from at least one of said diseases or disorder a compound of Formula (I), or a pharmaceutically acceptable salt, hydrate, solvate, prodrug, stereoisomer, or tautomer thereof.

The present invention provides inhibitors of c-Kit that are therapeutic agents in the treatment of diseases such as cancer, metastasis, inflammation and auto-immune pathogenesis.

The present disclosure provides agents with novel mechanisms of action toward c-Kit enzymes in the treatment of various types of diseases including cancer and cell proliferative disorders, multiple sclerosis, asthma, mastocytosis, inflammatory disorders, allergic reactions, fibrotic disorders, auto-immune pathogenesis and metabolic disorders. Ultimately the present invention provides the medical community with a novel pharmacological strategy for the treatment of diseases and disorders associated with c-Kit.

DETAILED DESCRIPTION OF THE INVENTION

The present invention relates to compounds and compositions that are capable of inhibiting the activity of c-Kit. The invention features methods of treating, preventing or ameliorating a disease or disorder in which c-Kit plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of c-Kit dependent diseases and disorders by inhibiting the activity of c-Kit enzymes. Inhibition of c-Kit provides a novel approach to the treatment, prevention, or amelioration of diseases including, but not limited to, cancer and metastasis.

In a first aspect of the invention, the compounds of Formula (I) are described:

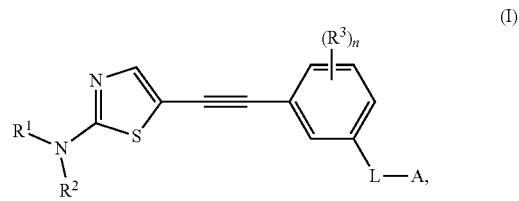

and pharmaceutically acceptable salts, hydrates, solvates, prodrugs, stereoisomers, and tautomers thereof, wherein A, L, $R_1$, $R_2$, $R_3$, and n are as described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$) haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1λ$^2$-pyrrolo[2,1-b]pyrimidine, dibenzo[b,d] thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Heterocyclyl" or "heterocycloalkyl" monocyclic rings containing carbon and heteroatoms taken from oxygen, nitrogen, or sulfur and wherein there is not delocalized π electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more —OH groups. Examples of hydroxyalkyl groups include HO—$CH_2$—, HO—$CH_2$—$CH_2$— and $CH_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "amine" as used herein refers to primary (R—$NH_2$, R H), secondary ($R_2$—NH, $R_2 \neq$H) and tertiary ($R_3$—N, R H) amines. A substituted amine is intended to mean an amine where at least one of the hydrogen atoms has been replaced by the substituent.

The term "amino" as used herein means a substituent containing at least one nitrogen atom. Specifically, $NH_2$, —NH(alkyl) or alkylamino, —N(alkyl)$_2$ or dialkylamino, amide-, carbamide-, urea, and sulfamide substituents are included in the term "amino".

The term "alkylamino" as used herein refers to an amino or $NH_2$ group where one of the hydrogens has been replaced with an alkyl group, as defined herein above, i.e., —NH(alkyl). Example of alkylamino groups include, but are not limited to, methylamino (i.e., —NH($CH_3$)), ethylamino, propylamino, iso-propylamino, n-butylamino, sec-butylamino, tert-butylamino, etc.

The term "dialkylamino" as used herein refers to an amino or $NH_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N($CH_3$)$_2$), diethylamino, dipropylamino, diiso-propyl amino, di-n-butylamino, di-sec-butylamino, di-tert-butylamino, methyl(ethyl)amino, methyl(butylamino), etc.

The term "oxo" as used herein refers to an "=O" group.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

As used herein, "treating" or "treat" describes the management and care of a patient for the purpose of reversing, inhibiting, or combating a disease, condition, or disorder and includes the administration of a compound of the present disclosure (i.e., a compound of Formula (I), or a pharmaceutically acceptable salt, prodrug, metabolite, polymorph or solvate thereof, to reverse the disease, condition, or disorder, eliminate the disease, condition, or disorder, or inhibit the process of the disease, condition, or disorder.

A compound of the present disclosure (e.g., a compound of Formula (I), or a pharmaceutically acceptable salt, prodrug, metabolite, polymorph or solvate thereof, can also be used to prevent a disease, condition, or disorder or one or more symptoms of such disease, condition, or disorder. As used herein, "preventing" or "prevent" describes reducing or eliminating the onset of the symptoms or complications of the disease, condition, or disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting c-Kit, which are useful for the treatment of diseases and disorders associated with modulation of a c-Kit enzyme. The invention further relates to compounds, or pharmaceutically acceptable salts, hydrates, solvates, prodrugs, stereoisomers, or tautomers thereof, which are useful for inhibiting c-Kit.

In one embodiment, the compounds of Formula (I) have the structure of Formula (Ia):

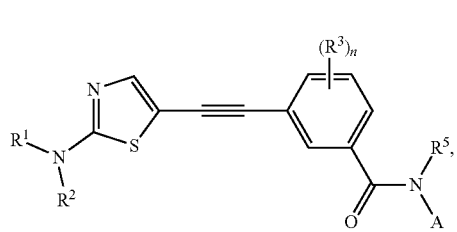

(Ia)

and pharmaceutically acceptable salts, hydrates, solvates, prodrugs, stereoisomers, and tautomers thereof.

In another embodiment, the compounds of Formula (I) have the structure of Formula (Ib):

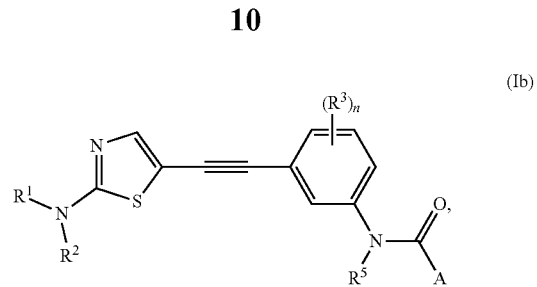

(Ib)

and pharmaceutically acceptable salts, hydrates, solvates, prodrugs, stereoisomers, and tautomers thereof.

In another embodiment, the compounds of Formula (I) have the structure of Formula (Ic):

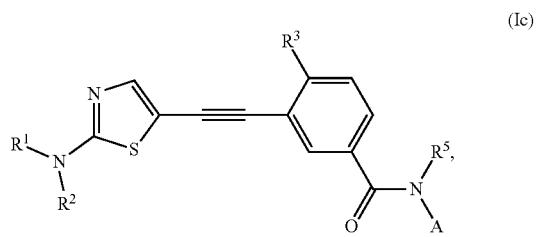

(Ic)

and pharmaceutically acceptable salts, hydrates, solvates, prodrugs, stereoisomers, and tautomers thereof.

In another embodiment, the compounds of Formula (I) have the structure of Formula (Id):

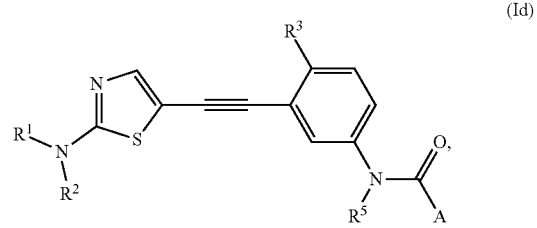

(Id)

and pharmaceutically acceptable salts, hydrates, solvates, prodrugs, stereoisomers, and tautomers thereof.

In another embodiment, the compounds of Formula (I) have the structure of Formula (Ie):

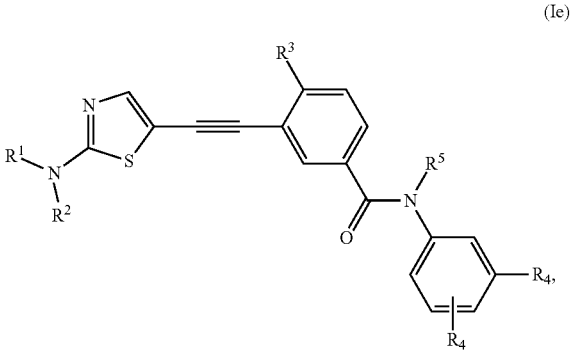

(Ie)

and pharmaceutically acceptable salts, hydrates, solvates, prodrugs, stereoisomers, and tautomers thereof.

In another embodiment, the compounds of Formula (I) have the structure of Formula (If):

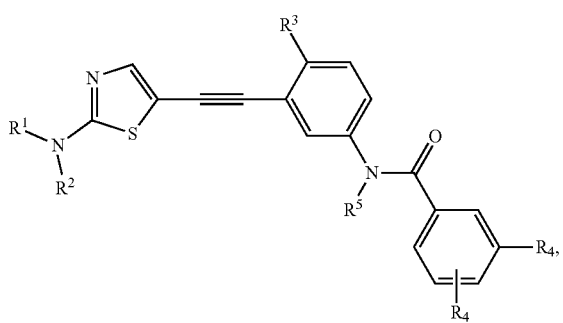

and pharmaceutically acceptable salts, hydrates, solvates, prodrugs, stereoisomers, and tautomers thereof.

In another embodiment, the compounds of Formula (I) have the structure of Formula (Ig):

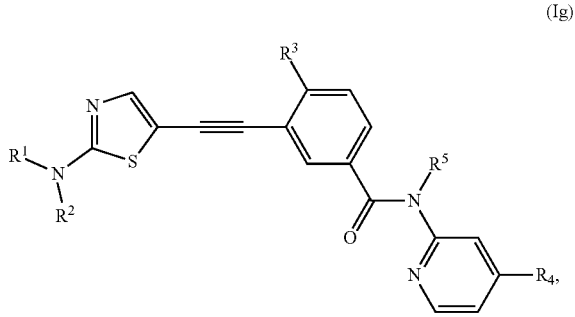

and pharmaceutically acceptable salts, hydrates, solvates, prodrugs, stereoisomers, and tautomers thereof.

In another embodiment, the compounds of Formula (I) have the structure of Formula (Ih):

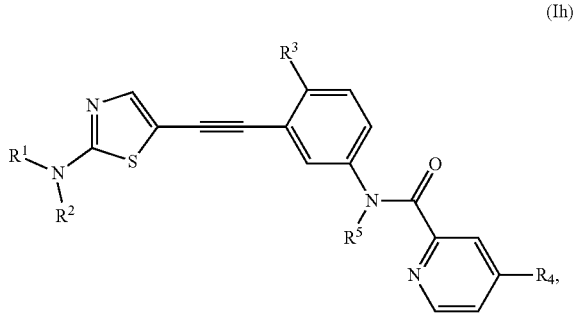

and pharmaceutically acceptable salts, hydrates, solvates, prodrugs, stereoisomers, and tautomers thereof.

In some embodiments of the Formulae above, A is ($C_6$-$C_{10}$) aryl. In another embodiment, A is 5- or 6-membered heteroaryl. In yet another embodiment, A is 6-membered aryl. In another embodiment, A is 6-membered heteroaryl. In yet another embodiment, A is phenyl. In a further embodiment, A is pyridinyl.

In some embodiments of the Formulae above, L is —C(O)NR$^5$—. In another embodiment, L is -C(O)NH—.

In some embodiments of the Formulae above, L is —NR$^5$C(O)—. In another embodiment, L is —NHC(O)—.

In some embodiments of the Formulae above, R$^1$ is H, ($C_1$-$C_6$) alkyl, —(CH$_2$)$_q$C(O)OH, or —C(O)N(R$^7$)$_2$. In another embodiment, R$^1$ is ($C_1$-$C_6$) alkyl, —(CH$_2$)$_q$C(O)OH, or —C(O)N(R$^7$)$_2$. In another embodiment, R$^1$ is H, —(CH$_2$)$_q$C(O)OH, or —C(O)N(R$^7$)$_2$. In yet another embodiment, R$^1$ is H, ($C_1$-$C_6$) alkyl, or —C(O)N(R$^7$)$_2$. In another embodiment, R$^1$ is H, ($C_1$-$C_6$) alkyl, or —(CH$_2$)$_q$C(O)OH. In another embodiment, R$^1$ is —(CH$_2$)$_q$C(O)OH, or —C(O)N(R$^7$)$_2$. In yet another embodiment, R$^1$ is H or ($C_1$-$C_6$) alkyl. In another embodiment, R$^1$ is H or —(CH$_2$)$_q$C(O)OH. In yet another embodiment, R$^1$ is H or —C(O)N(R$^7$)$_2$. In another embodiment, R$^1$ is H or ($C_1$-$C_6$) alkyl. In yet another embodiment, R$^1$ is H.

In some embodiments of the Formulae above, R$^2$ is ($C_1$-$C_6$) alkyl, —C(O)R$_8$, or —C(O)NR$^9$R$^{10}$. In another embodiment, R$^2$ is ($C_1$-$C_6$) alkyl or —C(O)R$_8$. In yet another embodiment, R$^2$ is —C(O)R$_8$ or —C(O)NR$^9$R$^{10}$. In another embodiment, R$^2$ is ($C_1$-$C_6$) alkyl or —C(O)NR$^9$R$^{10}$. In another embodiment, R$^2$ is ($C_1$-$C_6$) alkyl. In yet another embodiment, R$^2$ is —C(O)R$_8$. In another embodiment, R$^2$ is —C(O)NR$^9$R$^{10}$. In yet another embodiment, R$^2$ is —C(O)OCH$_3$. In another embodiment, R$^2$ is —C(O)CH$_3$. In yet another embodiment, R$^2$ is —C(O)-t-butyl.

In some embodiments of the Formulae above, R$^9$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S. In another embodiment, R$^9$ is H, ($C_1$-$C_6$) alkyl, ($C_1$-$C_6$) haloalkyl, or ($C_3$-$C_7$) cycloalkyl. In yet another embodiment, R$^9$ is H, ($C_1$-$C_6$) alkyl, or ($C_1$-$C_6$) haloalkyl. In another embodiment, R$^9$ is H or ($C_1$-$C_6$) alkyl. In yet another embodiment, R$^9$ is ($C_1$-$C_6$) alkyl. In another embodiment, R$^9$ is H, methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, or 2,3-dimethyl butane. In another embodiment, R$^9$ is H. In yet another embodiment, R$^9$ is methyl.

In some embodiments of the Formulae above, R$^{10}$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from ($C_1$-$C_6$) alkyl, —NH$_2$, ($C_1$-$C_6$) alkylamino, ($C_1$-$C_6$) dialkylamino, and —OH, and wherein the ($C_1$-$C_6$) alkyl is optionally substituted with one or more R$^{11}$. In another embodiment, R$^{10}$ is H, ($C_1$-$C_6$) alkyl, ($C_3$-$C_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from ($C_1$-$C_6$) alkyl, —NH$_2$, ($C_1$-$C_6$) alkylamino, ($C_1$-$C_6$) dialkylamino, and —OH, and wherein the ($C_1$-$C_6$) alkyl is optionally substituted with one or more R$^{11}$. In yet another embodiment, R$^{10}$ is H, ($C_1$-$C_6$) alkyl, or ($C_3$-$C_7$) cycloalkyl, wherein the cycloalkyl is optionally substituted with one or more substituents each independently selected from ($C_1$-$C_6$) alkyl, —NH$_2$, ($C_1$-$C_6$) alkylamino, ($C_1$-$C_6$) dialkylamino, and —OH, and wherein the ($C_1$-$C_6$) alkyl is optionally substituted with one or more R$^{11}$. In another embodiment, R$^{10}$ is H or ($C_1$-$C_6$) alkyl, wherein the ($C_1$-$C_6$) alkyl is optionally substituted with one or more R$^{11}$. In yet another embodiment, R$^{10}$ is ($C_1$-$C_6$) alkyl is optionally substituted with one or more R$^{11}$. In another embodiment, R$^{10}$ is methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, or 2,3-dimethyl butane, wherein the methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, or 2,3-dimethyl butane is optionally substituted with one or more $R^{11}$. In yet another embodiment, $R^{10}$ is H. In another embodiment, $R^{10}$ is methyl, ethyl, n-propyl, or n-butyl, wherein the methyl, ethyl, n-propyl, or n-butyl is optionally substituted with one or more $R^{11}$.

In an embodiment, $R^{10}$ is $(C_3-C_7)$ cycloalkyl, wherein the cycloalkyl is optionally substituted with one or more substituents each independently selected from $(C_1-C_6)$ alkyl, —$NH_2$, $(C_1-C_6)$ alkylamino, $(C_1-C_6)$ dialkylamino, and —OH. In another embodiment, $R^{10}$ is cyclopropyl or cyclohexyl, wherein the cyclopropyl or cyclohexyl is optionally substituted with one or more substituents each independently selected from $(C_1-C_6)$ alkyl, —$NH_2$, $(C_1-C_6)$ alkylamino, $(C_1-C_6)$ dialkylamino, and —OH.

In an embodiment, $R^{10}$ is 4 to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl, —$NH_2$, $(C_1-C_6)$ alkylamino, $(C_1-C_6)$ dialkylamino, and —OH. In another embodiment, $R^{10}$ is azetidinyl or piperidinyl, wherein the azetidinyl or piperidinyl is optionally substituted with one or more substituents each independently selected from $(C_1-C_6)$ alkyl, —$NH_2$, $(C_1-C_6)$ alkylamino, $(C_1-C_6)$ dialkylamino, and —OH.

In some embodiments of the Formulae above, $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from $(C_1-C_6)$ alkyl, $(C_1-C_6)$ hydroxyalkyl, —$(CH_2)_q$—$NH_2$, —$(CH_2)_q$—$(C_1-C_6)$ alkylamino, —$(CH_2)_q$—$(C_1-C_6)$ dialkylamino, —$C(O)(C_1-C_6)$ alkyl, —OH, and 4- to 7-membered heterocycloalkyl comprising 1 to 3 heteroatom selected from N, O, and S, and optionally substituted with one or more $(C_1-C_6)$ alkyl. In another embodiment, $R^9$ and $R^{10}$ together with the nitrogen atom to which they are attached form azetidinyl, morpholinyl, piperidinyl, or piperazinyl, optionally substituted with one or more substituent each independently selected from $(C_1-C_6)$ alkyl, $(C_1-C_6)$ hydroxyalkyl, —$(CH_2)_q$—$NH_2$, —$(CH_2)_q$—$(C_1-C_6)$ alkylamino, —$(CH_2)_q$—$(C_1-C_6)$ dialkylamino, —$C(O)(C_1-C_6)$ alkyl, —OH, and 4- to 7-membered heterocycloalkyl comprising 1 to 3 heteroatom selected from N, O, and S, and optionally substituted with one or more $(C_1-C_6)$ alkyl. In yet another embodiment, $R^9$ and $R^{10}$ together with the nitrogen atom to which they are attached form azetidinyl, morpholinyl, piperidinyl, or piperazinyl, optionally substituted with one or more substituent each independently selected from $(C_1-C_6)$ alkyl, $(C_1-C_6)$ hydroxyalkyl, —$(CH_2)_q$—$(C_1-C_6)$ dialkylamino, —$C(O)(C_1-C_6)$ alkyl, —OH, and 4- to 7-membered heterocycloalkyl comprising 1 to 3 heteroatom selected from N, O, and S, and optionally substituted with one or more $(C_1-C_6)$ alkyl.

In some embodiments of the Formulae above, $R^{11}$ is $(C_1-C_6)$ alkoxy, —OH, —$NH_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH. In another embodiment, $R^{11}$ is $(C_1-C_6)$ alkoxy, $(C_1-C_6)$ alkylamino, or $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH. In another embodiment, $R^{11}$ is 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH. In yet another embodiment, $R^{11}$ is OH. In another embodiment, $R^{11}$ is —$OCH_3$. In yet another embodiment, $R^{11}$ is —$NH_2$, —$NHCH_3$, —$N(CH_3)_2$, or —$N(CH_2CH_3)_2$. In yet another embodiment, $R^{11}$ is pyrrolidinyl, piperidinyl, piperazinyl, morpholinyl, or pyridinyl, wherein the pyrrolidinyl, piperidinyl, piperazinyl, or morpholinyl is optionally substituted with one or more substituents each independently selected from $(C_1-C_6)$ alkyl and OH.

In some embodiments of the Formulae above, $R^3$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or OH. In another embodiment, $R^3$ is independently at each occurrence $(C_1-C_6)$ alkyl, halogen, or OH. In yet another embodiment, $R^3$ is independently at each occurrence $(C_1-C_6)$ alkyl or halogen. In another embodiment, $R^3$ is independently at each occurrence methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, or 2,3-dimethyl butane. In yet another embodiment, $R^3$ is independently at each occurrence fluoro, chloro, bromo, or iodo. In another embodiment, $R^3$ is independently at each occurrence methyl or fluoro. In another embodiment, $R^3$ is methyl. In another embodiment, $R^3$ is fluoro.

In some embodiments of the Formulae above, $R^4$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, CN, —$(C(R^6)_2)_p$-heterocycloalkyl wherein the heterocycloalkyl comprises a 4- to 7-membered ring and 1 to 3 heteroatoms selected from N, O, and S, or —$(C(R^6)_2)_p$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from $(C_1-C_6)$ alkyl, —$NH_2$, $(C_1-C_6)$ alkylamino, and $(C_1-C_6)$ dialkylamino. In another embodiment, $R^4$ is independently at each occurrence $(C_1-C_6)$ alkoxy, $(C_1-C_6)$ haloalkyl, $(C_1-C_6)$ haloalkoxy, CN, or —$(C(R^6)_2)_p$-heterocycloalkyl wherein the heterocycloalkyl comprises a 4- to 7-membered ring and 1 to 3 heteroatoms selected from N, O, and S, wherein the heterocycloalkyl is optionally substituted with one or more substituents each independently selected from $(C_1-C_6)$ alkyl, —$NH_2$, $(C_1-C_6)$ alkylamino, and $(C_1-C_6)$ dialkylamino. In another embodiment, $R^4$ is independently at each occurrence $(C_1-C_6)$ alkoxy, $(C_1-C_6)$ haloalkyl, $(C_1-C_6)$ haloalkoxy, —OH, CN, or —$(C(R^6)_2)_p$-heterocycloalkyl wherein the heterocycloalkyl comprises a 5- or 6-membered ring and 1 to 3 heteroatoms selected from N, wherein the heterocycloalkyl is optionally substituted with one or more substituents each independently selected from $(C_1-C_6)$ alkyl. In another embodiment, $R^4$ is —$CF_3$. In yet another embodiment, $R^4$ is —$OCF_3$. In another embodiment, $R^4$ is —$OCH_3$. In yet another embodiment, $R^4$ is —$(C(R^6)_2)_p$-heterocycloalkyl wherein the heterocycloalkyl comprises pyrrolidinyl or piperazinyl, wherein the pyrrolidinyl or piperazinyl is optionally substituted with one or more substituents each independently selected from $(C_1-C_6)$ alkyl.

In some embodiments of the Formulae above, $R^5$ is H, $(C_1-C_6)$ alkyl, or $(C_1-C_6)$ haloalkyl. In another embodiment, $R^5$ is H or $(C_1-C_6)$ alkyl. In yet another embodiment, $R^5$ is H or $(C_1-C_6)$ haloalkyl. In another embodiment, $R^5$ is $(C_1-C_6)$ alkyl or $(C_1-C_6)$ haloalkyl. In another embodiment, $R^5$ is $(C_1-C_6)$ alkyl. In yet another embodiment, $R^5$ is methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, or 2,3-dimethyl butane. In another embodiment, $R^5$ is $(C_1-C_6)$ haloalkyl. In yet another embodiment, $R^5$ is H.

In some embodiments of the Formulae above, $R^6$ is H or $(C_1-C_6)$ alkyl. In another embodiment, $R^6$ is $(C_1-C_6)$ alkyl. In yet another embodiment, $R^6$ is H, methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, or 2,3-dimethyl butane. In another embodiment, $R^6$ is H. In yet another embodiment, $R^6$ is methyl.

In some embodiments of the Formulae above, $R^7$ is H or $(C_1-C_6)$ alkyl. In another embodiment, $R^7$ is $(C_1-C_6)$ alkyl. In yet another embodiment, $R^7$ is H, methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, or 2,3-dimethyl butane. In another embodiment, $R^7$ is H. In yet another embodiment, $R^7$ is methyl.

In some embodiments of the Formulae above, $R^8$ is $(C_1-C_6)$ alkyl, $(C_3-C_7)$ cycloalkyl, $(C_2-C_6)$ alkenyl, $(C_1-C_3)$ alkoxy, $(C_1-C_6)$ haloalkyl, $(C_1-C_6)$ haloalkoxy, or 4 to 7-membered heterocycloalkyl comprising 1 to 3 heteroatoms selected from N, O, and S. In another embodiment, $R^8$ is $(C_1-C_6)$ alkyl or $(C_1-C_3)$ alkoxy. In yet another embodiment, $R^8$ is methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, or 2,3-dimethyl butane. In another embodiment, $R^8$ is methyl or tert-butyl. In another embodiment, $R^8$ is $(C_1-C_3)$ alkoxy. In another embodiment, $R^8$ is methoxy.

In some embodiments of the Formulae above, each n, p, and q is independently 0, 1 or 2. In another embodiment, n is 0 or 1. In yet another embodiment, n is 0. In yet another embodiment, n is 1. In another embodiment, p is 0 or 1. In yet another embodiment, p is 0. In another embodiment, p is 1. In another embodiment, q is 0 or 1. In yet another embodiment, q is 0. In another embodiment, q is 1.

In some embodiments of the Formulae above, L is —C(O)NR$^5$—.

In some embodiments of the Formulae above, L is —NR$^5$C(O)—.

In some embodiments of the Formulae above, $R^3$ is $(C_1-C_6)$ alkyl or halogen.

In some embodiments of the Formulae above, n is 1 and $R^3$ is methyl or F.

In some embodiments of the Formulae above, n is 1 and $R^3$ is methyl.

In some embodiments of the Formulae above, A is $(C_6-C_{10})$ aryl optionally substituted with one or more $R^4$.

In some embodiments of the Formulae above, A is 6-membered heteroaryl optionally substituted with one or more $R^4$.

In some embodiments of the Formulae above, A is phenyl or pyridinyl optionally substituted with one or more $R^4$.

In some embodiments of the Formulae above, A is phenyl or pyridinyl substituted with one or more $R^4$.

In some embodiments of the Formulae above, $R^5$ is H.

In some embodiments of the Formulae above, n is 0.

In some embodiments of the Formulae above, n is 1.

In some embodiments of the Formulae above, n is 1 and $R^3$ is ortho to the alkyne.

In some embodiments of the Formulae above, $R^1$ is H, —C(O)N(CH$_3$)$_2$ or —CH$_2$CH$_2$C(O)OH.

In some embodiments of the Formulae above, $R^1$ is H.

In some embodiments of the Formulae above, one $R^4$ is $(C_1-C_6)$ haloalkyl and the other $R^4$ is $(C_1-C_6)$ alkoxy, CN, or —$(C(R^6)_2)_p$-heterocycloalkyl wherein the heterocycloalkyl comprises a 4- to 7-membered ring and 1 to 3 heteroatoms selected from N, O, and S.

In some embodiments of the Formulae above, at least one $R^4$ is CF$_3$ and the other $R^4$ is $(C_1-C_6)$ alkoxy, CN, or —$(C(R^6)_2)_p$-heterocycloalkyl wherein the heterocycloalkyl comprises a 4- to 7-membered ring and 1 to 3 heteroatoms selected from N, O, and S.

In some embodiments of the Formulae above, at least one $R^4$ is CF$_3$ and the other $R^4$ is —OCH$_3$, CN, or —(CH$_2$)-pyrrolyl.

In another embodiment, $R^1$ is H and $R^2$ is —C(O)NR$^9$R$^{10}$.

In some embodiments of the Formulae above, $R^9$ is H and $R^{10}$ is $(C_1-C_6)$ alkyl.

In some embodiments of the Formulae above, $R^9$ is H and $R^{10}$ is $(C_1-C_6)$ alkyl substituted with one $R_{11}$.

In some embodiments of the Formulae above, $R^{11}$ is $(C_1-C_6)$ alkoxy.

In some embodiments of the Formulae above, the $(C_1-C_6)$ alkoxy is —OCH$_3$.

In some embodiments of the Formulae above, $R^9$ is $(C_1-C_6)$ alkyl and $R^{10}$ is $(C_1-C_6)$ alkyl.

In some embodiments of the Formulae above, $R^9$ is $(C_1-C_6)$ alkyl and $R^{10}$ is $(C_1-C_6)$ alkyl substituted with one $R_{11}$.

In some embodiments of the Formulae above, $R^4$ is $(C_1-C_6)$ haloalkyl.

In some embodiments of the Formulae above, $R^4$ is CF$_3$.

In some embodiments of the Formulae above, n is 1 and $R^3$ is methyl.

In some embodiments of the Formulae above, $R^1$ is H and $R^2$ is $(C_1-C_6)$ alkyl.

In some embodiments of the Formulae above, $(C_1-C_6)$ alkyl is selected from methyl, ethyl, n-propyl, iso-propyl, n-butyl, sec-butyl, iso-butyl, tert-butyl, n-pentyl, iso-pentyl, tert-pentyl, neo-pentyl, sec-pentyl, 3-pentyl, n-hexane, 2-methyl pentane, 3-methyl pentane, 2,2-dimethyl butane, and 2,3-dimethyl butane.

In some embodiments of the Formulae above, $(C_1-C_6)$ alkyl is ethyl.

In some embodiments of the Formulae above, $(C_1-C_6)$ alkyl is methyl.

In some embodiments of the Formulae above, $R^1$ is H and $R^2$ is —C(O)R$^8$.

In another embodiment, $R^8$ is $(C_1-C_3)$ alkoxy.

In some embodiments of the Formulae above, $(C_1-C_3)$ alkoxy is OCH$_3$.

In some embodiments of the Formulae above, $R^1$ is H and $R^2$ is —C(O)NR$^9$R$^{10}$.

In some embodiments of the Formulae above, $R^9$ is H and $R^{10}$ is $(C_1-C_6)$ alkyl substituted with one $R^{11}$.

In some embodiments of the Formulae above, $R^{11}$ is $(C_1-C_6)$ dialkylamino.

In some embodiments of the Formulae above, $(C_1-C_6)$ dialkylamino is $-N(CH_3)_2$ or $-N(CH_2CH_3)_2$.

In some embodiments of the Formulae above, $R^{11}$ is $(C_1-C_6)$ alkylamino.

In some embodiments of the Formulae above, $(C_1-C_6)$ alkylamino is $-N(H)CH_3$.

In some embodiments of the Formulae above, $R^{11}$ is $-NH_2$.

In some embodiments of the Formulae above, $R^{11}$ is 5- or 6-membered heterocycloalkyl comprising 1 to 3 heteroatoms selected from N, O, or S, optionally substituted with $(C_1-C_6)$ alkyl or OH.

In some embodiments of the Formulae above, $R^{11}$ is 6-membered heteroaryl comprising 1 to 3 heteroatoms selected from N, O, or S.

In some embodiments of the Formulae above, $R^{11}$ is $-OH$.

In some embodiments of the Formulae above, $R^9$ is H and $R^{10}$ is $(C_3-C_7)$ cycloalkyl optionally substituted with $-OH$ or $-NH_2$.

In some embodiments of the Formulae above, $(C_3-C_7)$ cycloalkyl is cyclopropyl or cyclohexyl optionally substituted with $-OH$ or $-NH_2$.

In some embodiments of the Formulae above, $R^9$ is H and $R^{10}$ is 4 to 6-membered heterocycloalkyl comprising 1 to 3 heteroatoms selected from N, O, or S, optionally substituted with methyl.

In some embodiments of the Formulae above, $R^9$ is $(C_1-C_6)$ alkyl and $R^{10}$ is 4 to 6-membered heterocycloalkyl comprising 1 to 3 heteroatoms selected from N, O, or S, optionally substituted with methyl.

In some embodiments of the Formulae above, $R^9$ and $R^{10}$ together with the nitrogen atom to which they are attached form a 4- to 6-membered heterocycloalkyl ring comprising 1 to 3 heteroatom selected from N, O, and S, optionally substituted with one or more substituents each independently selected from $(C_1-C_6)$ alkyl, $(C_1-C_6)$ hydroxyalkyl, $-(CH_2)_q-(C_1-C_6)$ dialkylamino, $-C(O)(C_1-C_6)$ alkyl, OH, or 6-membered heterocycloalkyl comprising 1 to 3 heteroatom selected from N, O, and S, and optionally substituted with $(C_1-C_6)$ alkyl.

In some embodiments of the Formulae above, $(R^1$ is $-C(O)N(R^7)_2$ and $R^2$ is $-C(O)NR^9R^{10}$.

In some embodiments of the Formulae above, $R^1$ is $-(CH_2)_qC(O)OH$ and $R^2$ is $-C(O)R_8$.

In some embodiments of the Formulae above, $R^8$ is $(C_2-C_3)$ alkenyl.

In some embodiments of the Formulae above, n is 1 and $R^3$ is F.

In some embodiments of the Formulae above, $R^1$ is H and $R^2$ is $-C(O)NR^9R^{10}$.

In some embodiments of the Formulae above, n is 0, $R^1$ is H, and $R^2$ is $-C(O)NR^9R^{10}$.

In some embodiments of the Formulae above, when A is phenyl and $R^1$ is H, then $R^2$ is not $-C(O)CH_3$.

In some embodiments of the Formulae above, A is phenyl and $R^1$ is H, an $R^2$ is $(C_1-C_6)$ alkyl, $-C(O)R_8$, or $-C(O)NR^9R^{10}$, and $R^8$ is $(C_2-C_6)$ alkyl, $(C_3-C_7)$ cycloalkyl, $(C_2-C_6)$ alkenyl, $(C_1-C_3)$ alkoxy, $(C_1-C_6)$ haloalkyl, $(C_1-C_6)$ haloalkoxy, or 4 to 7-membered heterocycloalkyl comprising 1 to 3 heteroatoms selected from N, O, and S.

In some embodiments of the Formulae above, L is $-C(O)NR^5-$ or $-NR^5C(O)-$, A is $(C_3-C_8)$ cycloalkyl, $(C_6-C_{10})$ aryl, or 5- to 10-membered heteroaryl wherein the cycloalkyl, aryl, or heteroaryl is optionally substituted with one or more $R^4$, $R^1$ is H, $(C_1-C_6)$ alkyl, $-(CH_2)_qC(O)OH$, or $-C(O)N(R^7)_2$, $R^2$ is $(C_1-C_6)$ alkyl, $-C(O)R_8$, or $-C(O)NR^9R^{10}$, each $R^3$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or OH, each $R^4$ is independently at each occurrence $(C_1-C_6)$ alkyl, $(C_1-C_6)$ alkoxy, $(C_1-C_6)$ haloalkyl, $(C_1-C_6)$ haloalkoxy, halogen, $-OH$, CN, $-(C(R^6)_2)_p$-heterocycloalkyl wherein the heterocycloalkyl comprises a 4- to 7-membered ring and 1 to 3 heteroatoms selected from N, O, and S, or $-(C(R^6)_2)_p$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from $(C_1-C_6)$ alkyl, $-NH_2$, $(C_1-C_6)$ alkylamino, and $(C_1-C_6)$ dialkylamino, $R^5$ is H, $(C_1-C_6)$ alkyl, or $(C_1-C_6)$ haloalkyl, each $R^6$ is independently H or $(C_1-C_6)$ alkyl, each $R^7$ is independently H or $(C_1-C_6)$ alkyl, $R^8$ is $(C_1-C_6)$ alkyl, $(C_3-C_7)$ cycloalkyl, $(C_2-C_6)$ alkenyl, $(C_1-C_3)$ alkoxy, $(C_1-C_6)$ haloalkyl, $(C_1-C_6)$ haloalkoxy, or 4 to 7-membered heterocycloalkyl comprising 1 to 3 heteroatoms selected from N, O, and S, $R^9$ is H, $(C_1-C_6)$ alkyl, $(C_1-C_6)$ haloalkyl, $(C_3-C_7)$ cycloalkyl, or 4 to 7-membered heterocycloalkyl comprising 1 to 3 heteroatoms selected from N, O, or S, $R^{10}$ is H, $(C_1-C_6)$ alkyl, $(C_1-C_6)$ haloalkyl, $(C_3-C_7)$ cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from $(C_1-C_6)$ alkyl, $-NH_2$, $(C_1-C_6)$ alkylamino, $(C_1-C_6)$ dialkylamino, and $-OH$, and wherein the $(C_1-C_6)$ alkyl is optionally substituted with one or more $R^{11}$, or $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from $(C_1-C_6)$ alkyl, $(C_1-C_6)$ hydroxyalkyl, $-(CH_2)_q-NH_2$, $-(CH_2)_q-(C_1-C_6)$ alkylamino, $-(CH_2)_q-(C_1-C_6)$ dialkylamino, $-C(O)(C_1-C_6)$ alkyl, $-OH$, and 4- to 7-membered heterocycloalkyl comprising 1 to 3 heteroatom selected from N, O, and S, and optionally substituted with one or more $(C_1-C_6)$ alkyl, $R^1$ is $(C_1-C_6)$ alkoxy, $-OH$, $-NH_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and each n, p, and q is independently 0, 1 or 2; and provided that when A is phenyl and $R^1$ is H, then $R^2$ is not $-C(O)CH_3$.

In some embodiments of the Formulae above, L is $-C(O)NR^5-$, A is $(C_6-C_{10})$ aryl wherein the aryl is optionally substituted with one or more $R^4$, $R^1$ is H, $R^2$ is $(C_1-C_6)$ alkyl, $-C(O)R_8$, or $-C(O)NR^9R^{10}$, $R^3$ is $(C_1-C_6)$ alkyl, $R^4$ is $(C_1-C_6)$ haloalkyl, $R^5$ is H, $(C_1-C_6)$ alkyl, or $(C_1-C_6)$ haloalkyl, $R^8$ is $(C_1-C_6)$ alkyl, $(C_3-C_7)$ cycloalkyl, $(C_2-C_6)$ alkenyl, $(C_1-C_3)$ alkoxy, $(C_1-C_6)$ haloalkyl, $(C_1-C_6)$ haloalkoxy, or 4 to 7-membered heterocycloalkyl comprising 1 to 3 heteroatoms selected from N, O, and S, $R^9$ is H, $(C_1-C_6)$ alkyl, $(C_1-C_6)$ haloalkyl, $(C_3-C_7)$ cycloalkyl, or 4 to 7-membered heterocycloalkyl comprising 1 to 3 heteroatoms selected from N, O, or S, $R^{10}$ is H, $(C_1-C_6)$ alkyl, $(C_1-C_6)$ haloalkyl, $(C_3-C_7)$ cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from ($C_1$-$C_6$) alkyl, —$NH_2$, ($C_1$-$C_6$) alkylamino, ($C_1$-$C_6$) dialkylamino, and —OH, and wherein the ($C_1$-$C_6$) alkyl is optionally substituted with one or more $R^{11}$, or $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from ($C_1$-$C_6$) alkyl, ($C_1$-$C_6$) hydroxyalkyl, —$(CH_2)_q$—$NH_2$, —$(CH_2)_q$—($C_1$-$C_6$) alkylamino, —$(CH_2)_q$—($C_1$-$C_6$) dialkylamino, —$C(O)(C_1$-$C_6)$ alkyl, —OH, and 4- to 7-membered heterocycloalkyl comprising 1 to 3 heteroatom selected from N, O, and S, and optionally substituted with one or more ($C_1$-$C_6$) alkyl, $R^{11}$ is ($C_1$-$C_6$) alkoxy, —OH, —$NH_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 1.

In some embodiments of the Formulae above, L is —C(O)$NR^5$—, A is 5- to 10-membered heteroaryl wherein the heteroaryl is optionally substituted with one or more $R^4$, $R^1$ is H, $R^2$ is ($C_1$-$C_6$) alkyl, —$C(O)R_8$, or —$C(O)NR^9R^{10}$, $R^3$ is ($C_1$-$C_6$) alkyl, $R^4$ is ($C_1$-$C_6$) haloalkyl, $R^5$ is H, ($C_1$-$C_6$) alkyl, or ($C_1$-$C_6$) haloalkyl, $R^8$ is ($C_1$-$C_6$) alkyl, ($C_3$-$C_7$) cycloalkyl, ($C_2$-$C_6$) alkenyl, ($C_1$-$C_3$) alkoxy, ($C_1$-$C_6$) haloalkyl, ($C_1$-$C_6$) haloalkoxy, or 4 to 7-membered heterocycloalkyl comprising 1 to 3 heteroatoms selected from N, O, and S, $R^9$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, $R^{10}$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from ($C_1$-$C_6$) alkyl, —$NH_2$, ($C_1$-$C_6$) alkylamino, ($C_1$-$C_6$) dialkylamino, and —OH, and wherein the ($C_1$-$C_6$) alkyl is optionally substituted with one or more $R^{11}$, or $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from ($C_1$-$C_6$) alkyl, ($C_1$-$C_6$) hydroxyalkyl, —$(CH_2)_q$—$NH_2$, —$(CH_2)_q$—($C_1$-$C_6$) alkylamino, —$(CH_2)_q$—($C_1$-$C_6$) dialkylamino, —$C(O)(C_1$-$C_6)$ alkyl, —OH, and 4- to 7-membered heterocycloalkyl comprising 1 to 3 heteroatom selected from N, O, and S, and optionally substituted with one or more ($C_1$-$C_6$) alkyl, $R^{11}$ is ($C_1$-$C_6$) alkoxy, —OH, —$NH_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 1.

In another embodiment, L is —C(O)$NR^5$—, wherein $R^5$ is H, A is pyridinyl optionally substituted with one or more $R^4$, wherein $R^4$ is —$CF_3$, $R^1$ is H, $R^2$ is —$C(O)R_8$, $R^3$ is methyl, $R^8$ is ($C_1$-$C_6$) alkyl, ($C_3$-$C_7$) cycloalkyl, ($C_2$-$C_6$) alkenyl, ($C_1$-$C_3$) alkoxy, ($C_1$-$C_6$) haloalkyl, ($C_1$-$C_6$) haloalkoxy, or 4 to 7-membered heterocycloalkyl comprising 1 to 3 heteroatoms selected from N, O, and S, and n is 1.

In another embodiment, L is —C(O)$NR^5$—, wherein $R^5$ is H, A is pyridinyl optionally substituted with one or more $R^4$, wherein $R^4$ is —$CF_3$, $R^1$ is H, $R^2$ is —$C(O)R_8$, $R^3$ is methyl, $R^8$ is ($C_1$-$C_6$) alkyl, ($C_3$-$C_7$) cycloalkyl, or ($C_1$-$C_3$) alkoxy, and n is 1. In another embodiment, $R^8$ is methoxy. In another embodiment, $R^8$ is methyl. In another embodiment, $R^8$ is t-butyl. In another embodiment, $R^8$ is cyclopropyl.

In another embodiment, L is —C(O)$NR^5$—, wherein $R^5$ is H, A is pyridinyl optionally substituted with one or more $R^4$, wherein $R^4$ is —$CF_3$, $R^1$ is H, $R^3$ is methyl, $R^2$ is —$C(O)NR^9R^{10}$, wherein $R^9$ is H and $R^{10}$ is H, ($C_1$-$C_6$) alkyl, or ($C_3$-$C_7$) cycloalkyl, wherein the ($C_1$-$C_6$) alkyl is optionally substituted with one or more $R^{11}$, wherein $R^{11}$ is ($C_1$-$C_6$) alkoxy, —OH, —$NH_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 1.

In another embodiment, L is —C(O)$NR^5$—, wherein $R^5$ is H, A is pyridinyl substituted with one or more $R^4$, wherein $R^4$ is —$CF_3$, $R^1$ is H, $R^3$ is methyl, $R^2$ is —$C(O)NR^9R^{10}$, wherein $R^9$ is H and $R^{10}$ is H, methyl, ethyl, propyl, n-butyl, isobutyl, or cyclopropyl, wherein the methyl, ethyl, propyl, n-butyl, or isobutyl is optionally substituted with one or more $R^{11}$, wherein $R^{11}$ is ($C_1$-$C_6$) alkoxy, —OH, —$NH_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1. In another embodiment, $R^{10}$ is H. In another embodiment, $R^{10}$ is cyclopropyl.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is H and $R^{10}$ is methyl, ethyl, propyl, n-butyl, or isobutyl, wherein the methyl, ethyl, propyl, n-butyl, or isobutyl is substituted with one or more $R^{11}$, wherein $R^{11}$ is $(C_1-C_6)$ alkoxy, —OH, —NH$_2$, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is H and $R^{10}$ is methyl, wherein the methyl is optionally substituted with one or more $R^{11}$, wherein $R^{11}$ is 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1. In another embodiment, $R^{10}$ is methyl. In another embodiment, $R^{10}$ is methyl, wherein the methyl is substituted with $R^{11}$, wherein $R^{11}$ is N-methylpiperidinyl. In another embodiment, $R^{10}$ is methyl, wherein the methyl is substituted with $R^{11}$, wherein $R^{11}$ is pyridinyl.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is H and $R^{10}$ is ethyl, wherein the ethyl is substituted with one or more $R^{11}$, wherein $R^{11}$ is $(C_1-C_6)$ alkoxy, —NH$_2$, $(C_1-C_6)$ dialkylamino, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1. In another embodiment, $R^{10}$ is ethyl, wherein the ethyl is substituted with $R^{11}$, wherein $R^{11}$ is methoxy. In another embodiment, $R^{10}$ is ethyl, wherein the ethyl is substituted with $R^{11}$, wherein $R^{11}$ is dimethylamino. In another embodiment, $R^{10}$ is ethyl, wherein the ethyl is substituted with one or more $R^{11}$, wherein $R^{11}$ is —NH$_2$, and n is 1.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is H and $R^{10}$ is ethyl, wherein the ethyl is substituted with one or more $R^{11}$, wherein $R^{11}$ is 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1. In another embodiment, $R^{10}$ is ethyl, wherein the ethyl is substituted with $R^{11}$, and wherein $R^{11}$ is morpholinyl. In another embodiment, $R^{10}$ is ethyl, wherein the ethyl is substituted with $R^1$, and wherein $R^{11}$ is pyrrolidinyl. In another embodiment, $R^{10}$ is ethyl, wherein the ethyl is substituted with $R^{11}$, and wherein $R^{11}$ is N-methylpiperazinyl. In another embodiment, $R^{10}$ is ethyl, wherein the ethyl is substituted with $R^{11}$, and wherein $R^{11}$ is 3-hydroxypyrrolidinyl.

In another embodiment, L is —C(O)NR$^5$—, wherein $R^5$ is H, A is pyridinyl substituted with one or more $R^4$, wherein $R^4$ is —CF$_3$, $R^1$ is H, $R^3$ is methyl, $R^2$ is —C(O)NR$^9$R$^{10}$, wherein $R^9$ is H and $R^{10}$ is H, methyl, ethyl, propyl, n-butyl, isobutyl, or cyclopropyl, wherein the methyl, ethyl, propyl, n-butyl, or isobutyl is optionally substituted with one or more $R^{11}$, wherein $R^{11}$ is —OH or —NH$_2$, and n is 1. In another embodiment, $R^{10}$ is isobutyl, wherein the isobutyl is substituted with $R^{11}$, wherein $R^{11}$ is —OH. In another embodiment, $R^{10}$ is n-butyl, wherein the n-butyl is substituted with $R^{11}$, wherein $R^{11}$ is —NH$_2$. In another embodiment, $R^{10}$ is n-propyl, wherein the n-propyl is substituted with $R^{11}$, wherein $R^{11}$ is —NH$_2$.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is H, $(C_1-C_6)$ alkyl, $(C_1-C_6)$ haloalkyl, $(C_3-C_7)$ cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from $(C_1-C_6)$ alkyl, —NH$_2$, $(C_1-C_6)$ alkylamino, $(C_1-C_6)$ dialkylamino, and —OH, and wherein the $(C_1-C_6)$ alkyl is optionally substituted with one or more $R^{11}$, wherein $R^{11}$ is $(C_1-C_6)$ alkoxy, —OH, —NH$_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1.

In another embodiment, L is —C(O)NR$^5$—, wherein $R^5$ is H, A is pyridinyl substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is methyl, ethyl, propyl, n-butyl, or isobutyl, wherein the methyl, ethyl, propyl, n-butyl, or isobutyl is optionally substituted with one or more $R^{11}$, wherein $R^{11}$ is $(C_1-C_6)$ alkoxy, —OH, —NH$_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1.

In another embodiment, L is —C(O)NR$^5$—, wherein $R^5$ is H, A is pyridinyl substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is methyl, ethyl, or isobutyl, wherein the methyl, ethyl, or isobutyl is optionally substituted with one or more $R^{11}$, wherein $R^{11}$ is $(C_1-C_6)$ alkoxy, —OH, —NH$_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1. In another embodiment, $R^{10}$ is methyl, wherein the methyl is substituted with $R^{11}$, wherein $R^{11}$ is 2-methylpyrrolidinyl. In another embodiment, $R^{10}$ is isobutyl, wherein the isobutyl is substituted with $R^{11}$, wherein $R^{11}$ is —OH. In another embodiment, $R^{10}$ is methyl. In another embodiment, $R^{10}$ is ethyl.

In another embodiment, L is —C(O)NR$^5$—, wherein $R^5$ is H, A is pyridinyl substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is ethyl, wherein the ethyl is substituted with one or more $R^{11}$, wherein $R^{11}$ is $(C_1-C_6)$ alkoxy, —OH, —NH$_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1.

In another embodiment, L is —C(O)NR$^5$—, wherein $R^5$ is H, A is pyridinyl substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is ethyl, wherein the ethyl is substituted with one or more $R^{11}$, wherein $R^{11}$ is $(C_1-C_6)$ alkoxy, —OH, $(C_1-C_6)$ alkylamino, $(C_1-C_6)$ dialkylamino, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1. In another embodiment, $R^{11}$ is methoxy. In another embodiment, $R^{11}$ is dimethylamino. In another embodiment, $R^{11}$ is —OH. In another embodiment, $R^{11}$ is —NHCH$_3$. In another embodiment, $R^{11}$ is N-methylpiperazinyl. In another embodiment, $R^{11}$ is pyrrolidinyl.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is $(C_3-C_7)$ cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from $(C_1-C_6)$ alkyl, —NH$_2$, $(C_1-C_6)$ alkylamino, $(C_1-C_6)$ dialkylamino, and —OH, and wherein the $(C_1-C_6)$ alkyl is optionally substituted with one or more $R^1$, wherein $R^{11}$ is $(C_1-C_6)$ alkoxy, —OH, —NH$_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and n is 1.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is $(C_3-C_7)$ cycloalkyl, wherein the cycloalkyl is optionally substituted with one or more substituents each independently selected from $(C_1-C_6)$ alkyl, —NH$_2$, $(C_1-C_6)$ alkylamino, $(C_1-C_6)$ dialkylamino, and —OH, and n is 1.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is cyclohexyl, wherein the cyclohexyl is optionally substituted with one or more substituents each independently selected from $(C_1-C_6)$ alkyl, —NH$_2$, $(C_1-C_6)$ alkylamino, $(C_1-C_6)$ dialkylamino, and —OH, and n is 1. In another embodiment, $R^{10}$ is cyclohexyl, wherein the cyclohexyl is substituted with —OH. In another embodiment, $R^{10}$ is cyclohexyl, wherein the cyclohexyl is substituted with —NH$_2$.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is 4 to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl, —NH$_2$, $(C_1-C_6)$ alkylamino, $(C_1-C_6)$ dialkylamino, and —OH, and n is 1.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is methyl, $R^2$ is —C(O)NR$^9$R$^{10}$, wherein $R^9$ is methyl and $R^{10}$ is piperidinyl, wherein the piperidinyl is optionally substituted with one or more substituents each independently selected from $(C_1-C_6)$ alkyl, —NH$_2$, $(C_1-C_6)$ alkylamino, $(C_1-C_6)$ dialkylamino, and —OH, and n is 1. In another embodiment, $R^{10}$ is piperidinyl, wherein the piperidinyl is substituted with methyl. In another embodiment, $R^{10}$ is azetidinyl, wherein the azetidinyl is substituted with methyl.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^2$ is —C(O)NR$^9$R$^{10}$, $R^3$ is methyl, $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from $(C_1-C_6)$ alkyl, $(C_1-C_6)$ hydroxyalkyl, —(CH$_2$)$_q$—NH$_2$, —(CH$_2$)$_q$—$(C_1-C_6)$ alkylamino, —(CH$_2$)$_q$—$(C_1-C_6)$ dialkylamino, —C(O)$(C_1-C_6)$ alkyl, —OH, and 4- to 7-membered heterocycloalkyl comprising 1 to 3 heteroatom selected from N, O, and S, and optionally substituted with one or more $(C_1-C_6)$ alkyl, and n is 1. In another embodiment, $R^9$ and $R^{10}$ together with the nitrogen atom to which they are attached form an azetidine ring, wherein the azetidine ring is substituted with methyl. In another embodiment, $R^9$ and $R^{10}$ together with the nitrogen atom to which they are attached form a pyrrolidine ring, wherein the pyrrolidine ring is substituted with dimethylamino.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^2$ is —C(O)NR$^9$R$^{10}$, $R^3$ is methyl, $R^9$ and $R^{10}$ together with the nitrogen atom to which they are attached form a piperazine ring, optionally substituted with one or more substituent each independently selected from $(C_1-C_6)$ alkyl, $(C_1-C_6)$ hydroxyalkyl, —(CH$_2$)$_q$—NH$_2$, —(CH$_2$)$_q$$(C_1-C_6)$ alkylamino, —(CH$_2$)$_q$—$(C_1-C_6)$ dialkylamino, —C(O)$(C_1-C_6)$ alkyl, —OH, and 4- to 7-membered heterocycloalkyl comprising 1 to 3 heteroatom selected from N, O, and S, and optionally substituted with one or more $(C_1-C_6)$ alkyl, and n is 1. In another embodiment, $R^9$ and $R^{10}$ together with the nitrogen atom to which they are attached form a piperazine ring. In another embodiment, $R^9$ and $R^{10}$ together with the nitrogen atom to which they are attached form a piperazine ring, wherein the piperazine ring is substituted with methyl. In another embodiment, $R^9$ and $R^{10}$ together with the nitrogen atom to which they are attached form a piperazine ring, wherein the piperazine ring is substituted with hydroxyethyl. In another embodiment, $R^9$ and $R^{10}$ together with the nitrogen atom to which they are attached form a piperazine ring, wherein the piperazine ring is substituted with C(O)CH$_3$.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^2$ is —C(O)NR$^9$R$^{10}$, $R^3$ is methyl, $R^9$ and $R^{10}$ together with the nitrogen atom to which they are attached form a piperidine ring, optionally substituted with one or more substituent each independently selected from $(C_1-C_6)$ alkyl, $(C_1-C_6)$ hydroxyalkyl, —(CH$_2$)$_q$—NH$_2$, —(CH$_2$)$_q$—$(C_1-C_6)$ alkylamino, —(CH$_2$)$_q$—$(C_1-C_6)$ dialkylamino, —C(O)$(C_1-C_6)$ alkyl, —OH, and 4- to 7-membered heterocycloalkyl comprising 1 to 3 heteroatom selected from N, O, and S, and optionally substituted with one or more ($C_1$-$C_6$) alkyl, and n is 1. In another embodiment, $R^9$ and $R^{10}$ together with the nitrogen atom to which they are attached form a piperidine ring, wherein the piperidine ring is substituted with methyl. In another embodiment, $R^9$ and $R^{10}$ together with the nitrogen atom to which they are attached form a piperidine ring, wherein the piperidine ring is substituted with N-methylpiperazine.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^2$ is —C(O)NR$^9$R$^{10}$, $R^3$ is methyl, $R^9$ and $R^{10}$ together with the nitrogen atom to which they are attached form a morpholine ring, optionally substituted with one or more substituent each independently selected from ($C_1$-$C_6$) alkyl, ($C_1$-$C_6$) hydroxyalkyl, —(CH$_2$)$_q$—NH$_2$, —(CH$_2$)$_q$($C_1$-$C_6$) alkylamino, —(CH$_2$)$_q$—($C_1$-$C_6$) dialkylamino, —C(O)($C_1$-$C_6$) alkyl, —OH, and 4- to 7-membered heterocycloalkyl comprising 1 to 3 heteroatom selected from N, O, and S, and optionally substituted with one or more ($C_1$-$C_6$) alkyl, and n is 1. In another embodiment, $R^9$ and $R^{10}$ together with the nitrogen atom to which they are attached form a morpholine ring. In another embodiment, $R^9$ and $R^{10}$ together with the nitrogen atom to which they are attached form a morpholine ring, wherein the morpholine ring is substituted with —(CH$_2$)$_q$—($C_1$-$C_6$) dialkylamino, wherein q is 1 and the —(CH$_2$)$_q$—($C_1$-$C_6$) dialkylamino is —CH$_2$N(CH$_3$)$_2$.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^2$ is ($C_1$-$C_6$) alkyl, —C(O)R$_8$, or —C(O)NR$^9$R$^{10}$, $R^3$ is fluoro, $R^8$ is ($C_1$-$C_6$) alkyl, ($C_3$-$C_7$) cycloalkyl, ($C_2$-$C_6$) alkenyl, ($C_1$-$C_3$) alkoxy, ($C_1$-$C_6$) haloalkyl, ($C_1$-$C_6$) haloalkoxy, or 4 to 7-membered heterocycloalkyl comprising 1 to 3 heteroatoms selected from N, O, and S, $R^9$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, $R^{10}$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from ($C_1$-$C_6$) alkyl, —NH$_2$, ($C_1$-$C_6$) alkylamino, ($C_1$-$C_6$) dialkylamino, and —OH, and wherein the ($C_1$-$C_6$) alkyl is optionally substituted with one or more $R^{11}$, or $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from ($C_1$-$C_6$) alkyl, ($C_1$-$C_6$) hydroxyalkyl, —(CH$_2$)$_q$—NH$_2$, —(CH$_2$)$_q$—($C_1$-$C_6$) alkylamino, —(CH$_2$)$_q$—($C_1$-$C_6$) dialkylamino, —C(O)($C_1$-$C_6$) alkyl, —OH, and 4- to 7-membered heterocycloalkyl comprising 1 to 3 heteroatom selected from N, O, and S, and optionally substituted with one or more ($C_1$-$C_6$) alkyl, $R^{11}$ is ($C_1$-$C_6$) alkoxy, —OH, —NH$_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 1.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is fluoro, $R^2$ is —C(O)NR$^9$R$^{10}$, wherein $R^9$ is H and $R^{10}$ is H or ($C_1$-$C_6$) alkyl, wherein the ($C_1$-$C_6$) alkyl is optionally substituted with one or more $R^{11}$, wherein $R^{11}$ is ($C_1$-$C_6$) alkoxy, —OH, —NH$_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 1.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^3$ is fluoro, $R^2$ is —C(O)NR$^9$R$^{10}$, wherein $R^9$ is H and $R^{10}$ is H or ($C_1$-$C_6$) alkyl, and n is 1. In another embodiment, $R^{10}$ is H. In another embodiment, $R^{10}$ is methyl.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^2$ is ($C_1$-$C_6$) alkyl, —C(O)R$_8$, or —C(O)NR$^9$R$^{10}$, $R^8$ is ($C_1$-$C_6$) alkyl, ($C_3$-$C_7$) cycloalkyl, ($C_2$-$C_6$) alkenyl, ($C_1$-$C_3$) alkoxy, ($C_1$-$C_6$) haloalkyl, ($C_1$-$C_6$) haloalkoxy, or 4 to 7-membered heterocycloalkyl comprising 1 to 3 heteroatoms selected from N, O, and S, $R^9$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, $R^{10}$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from ($C_1$-$C_6$) alkyl, —NH$_2$, ($C_1$-$C_6$) alkylamino, ($C_1$-$C_6$) dialkylamino, and —OH, and wherein the ($C_1$-$C_6$) alkyl is optionally substituted with one or more $R^{11}$, or $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from ($C_1$-$C_6$) alkyl, ($C_1$-$C_6$) hydroxyalkyl, —(CH$_2$)$_q$—NH$_2$, —(CH$_2$)$_q$—($C_1$-$C_6$) alkylamino, —(CH$_2$)$_q$($C_1$-$C_6$) dialkylamino, —C(O)($C_1$-$C_6$) alkyl, —OH, and 4- to 7-membered heterocycloalkyl comprising 1 to 3 heteroatom selected from N, O, and S, and optionally substituted with one or more ($C_1$-$C_6$) alkyl, $R^{11}$ is ($C_1$-$C_6$) alkoxy, —OH, —NH$_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 0.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^2$ is —C(O)NR$^9$R$^{10}$, wherein $R^9$ is H and $R^{10}$ is H or ($C_1$-$C_6$) alkyl, wherein the ($C_1$-$C_6$) alkyl is optionally substituted with one or more $R^{11}$, wherein $R^{11}$ is ($C_1$-$C_6$) alkoxy, —OH, —NH$_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 0.

In another embodiment, L is —C(O)NR$^5$—, wherein $R^5$ is H, A is pyridinyl optionally substituted with one or more $R^4$, wherein $R^4$ is —CF$_3$, $R^1$ is H, $R^2$ is —C(O)NR$^9$R$^{10}$, wherein $R^9$ is H and $R^{10}$ is ($C_1$-$C_6$) alkyl, and n is 0. In another embodiment, L is —C(O)NR$^5$—, wherein $R^5$ is H, A is pyridinyl optionally substituted with one or more $R^4$, wherein $R^4$ is —$CF_3$, $R^1$ is H, $R^2$ is —C(O)$NR^9R^{10}$, wherein $R^9$ is H and $R^{10}$ is methyl, and n is 0.

In another embodiment, L is —C(O)$NR^5$—, wherein $R^5$ is H, A is phenyl optionally substituted with one or more $R^4$, wherein $R^4$ is ($C_1$-$C_6$) alkyl, ($C_1$-$C_6$) alkoxy, ($C_1$-$C_6$) haloalkyl, ($C_1$-$C_6$) haloalkoxy, halogen, —OH, CN, —(C($R^6$)$_2$)$_p$-heterocycloalkyl wherein the heterocycloalkyl comprises a 4- to 7-membered ring and 1 to 3 heteroatoms selected from N, O, and S, or —(C($R^6$)$_2$)$_p$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from ($C_1$-$C_6$) alkyl, —$NH_2$, ($C_1$-$C_6$) alkylamino, and ($C_1$-$C_6$) dialkylamino, $R^1$ is H, $R^2$ is ($C_1$-$C_6$) alkyl, —C(O)$R_8$, or —C(O)$NR^9R^{10}$, $R^3$ is methyl, $R^8$ is ($C_1$-$C_6$) alkyl, ($C_3$-$C_7$) cycloalkyl, ($C_2$-$C_6$) alkenyl, ($C_1$-$C_3$) alkoxy, ($C_1$-$C_6$) haloalkyl, ($C_1$-$C_6$) haloalkoxy, or 4 to 7-membered heterocycloalkyl comprising 1 to 3 heteroatoms selected from N, O, and S, $R^9$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, $R^{10}$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from ($C_1$-$C_6$) alkyl, —$NH_2$, ($C_1$-$C_6$) alkylamino, ($C_1$-$C_6$) dialkylamino, and —OH, and wherein the ($C_1$-$C_6$) alkyl is optionally substituted with one or more $R^{11}$, or $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from ($C_1$-$C_6$) alkyl, ($C_1$-$C_6$) hydroxyalkyl, —(CH$_2$)$_q$—$NH_2$, —(CH$_2$)$_q$—($C_1$-$C_6$) alkylamino, —(CH$_2$)$_q$—($C_1$-$C_6$) dialkylamino, —C(O)($C_1$-$C_6$) alkyl, —OH, and 4- to 7-membered heterocycloalkyl comprising 1 to 3 heteroatom selected from N, O, and S, and optionally substituted with one or more ($C_1$-$C_6$) alkyl, $R^{11}$ is ($C_1$-$C_6$) alkoxy, —OH, —$NH_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 1.

In another embodiment, L is —C(O)$NR^5$—, wherein $R^5$ is H, A is phenyl optionally substituted with one or more $R^4$, wherein $R^4$ is ($C_1$-$C_6$) alkyl, ($C_1$-$C_6$) alkoxy, ($C_1$-$C_6$) haloalkyl, ($C_1$-$C_6$) haloalkoxy, halogen, —OH, CN, —(C($R^6$)$_2$)$_p$-heterocycloalkyl wherein the heterocycloalkyl comprises a 4- to 7-membered ring and 1 to 3 heteroatoms selected from N, O, and S, or —(C($R^6$)$_2$)$_p$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from ($C_1$-$C_6$) alkyl, —$NH_2$, ($C_1$-$C_6$) alkylamino, and ($C_1$-$C_6$) dialkylamino, $R^1$ is H, $R^2$ is —C(O)$R_8$, $R^3$ is methyl, $R^8$ is ($C_1$-$C_6$) alkyl, ($C_3$-$C_7$) cycloalkyl, ($C_2$-$C_6$) alkenyl, ($C_1$-$C_3$) alkoxy, ($C_1$-$C_6$) haloalkyl, ($C_1$-$C_6$) haloalkoxy, or 4 to 7-membered heterocycloalkyl comprising 1 to 3 heteroatoms selected from N, O, and S, and n is 1.

In another embodiment, L is —C(O)$NR^5$—, wherein $R^5$ is H, A is phenyl optionally substituted with one or more $R^4$, wherein $R^4$ is selected from —$CF_3$ and —$CH_2$—N—methylpiperazinyl, $R^1$ is H, $R^2$ is —C(O)$R_8$, $R^3$ is methyl, $R^8$ is ($C_1$-$C_6$) alkyl, ($C_3$-$C_7$) cycloalkyl, or ($C_1$-$C_3$) alkoxy, and n is 1.

In another embodiment, L is —C(O)$NR^5$—, wherein $R^5$ is H, A is phenyl optionally substituted with one or more $R^4$, wherein $R^4$ is selected from —$CF_3$ and —$CH_2$—N—methylpiperazinyl, $R^1$ is H, $R^2$ is —C(O)$R_8$, $R^3$ is methyl, $R^8$ is ($C_3$-$C_7$) cycloalkyl, and n is 1. In another embodiment, $R^8$ is cyclopropyl.

In another embodiment, L is —C(O)$NR^5$—, wherein $R^5$ is H, A is phenyl optionally substituted with one or more $R^4$, wherein $R^4$ is ($C_1$-$C_6$) alkyl, ($C_1$-$C_6$) alkoxy, ($C_1$-$C_6$) haloalkyl, ($C_1$-$C_6$) haloalkoxy, halogen, —OH, CN, —(C($R^6$)$_2$)$_p$-heterocycloalkyl wherein the heterocycloalkyl comprises a 4- to 7-membered ring and 1 to 3 heteroatoms selected from N, O, and S, or —(C($R^6$)$_2$)$_p$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from ($C_1$-$C_6$) alkyl, —$NH_2$, ($C_1$-$C_6$) alkylamino, and ($C_1$-$C_6$) dialkylamino, $R^1$ is H, $R^3$ is methyl, $R^2$ is —C(O)$NR^9R^{10}$, wherein $R^9$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, $R^{10}$ is H, ($C_1$-$C_6$) alkyl, ($C_1$-$C_6$) haloalkyl, ($C_3$-$C_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from ($C_1$-$C_6$) alkyl, —$NH_2$, ($C_1$-$C_6$) alkylamino, ($C_1$-$C_6$) dialkylamino, and —OH, and wherein the ($C_1$-$C_6$) alkyl is optionally substituted with one or more $R^{11}$, wherein $R^{11}$ is ($C_1$-$C_6$) alkoxy, —OH, —$NH_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 1.

In another embodiment, L is —C(O)$NR^5$—, wherein $R^5$ is H, A is phenyl optionally substituted with one or more $R^4$, wherein $R^4$ is ($C_1$-$C_6$) alkyl, ($C_1$-$C_6$) alkoxy, ($C_1$-$C_6$) haloalkyl, ($C_1$-$C_6$) haloalkoxy, halogen, —OH, CN, —(C($R^6$)$_2$)$_p$-heterocycloalkyl wherein the heterocycloalkyl comprises a 4- to 7-membered ring and 1 to 3 heteroatoms selected from N, O, and S, or —(C($R^6$)$_2$)$_p$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from ($C_1$-$C_6$) alkyl, —$NH_2$, ($C_1$-$C_6$) alkylamino, and ($C_1$-$C_6$) dialkylamino, $R^1$ is H, $R^3$ is methyl, $R^2$ is —C(O)$NR^9R^{10}$, wherein $R^9$ is methyl and $R^{10}$ is ($C_1$-$C_6$) alkyl, wherein the ($C_1$-$C_6$) alkyl is optionally substituted with one or more $R^{11}$, wherein $R^{11}$ is ($C_1$-$C_6$) alkoxy, —OH, —$NH_2$, ($C_1$-$C_6$) alkylamino, ($C_1$-$C_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from ($C_1$-$C_6$) alkyl and OH; and n is 1.

In another embodiment, L is —C(O)$NR^5$—, wherein $R^5$ is H, A is phenyl optionally substituted with one or more $R^4$, wherein $R^4$ is selected from —$CF_3$, CN, methoxy, and —C(R$^6$)$_2$)$_p$-heterocycloalkyl, wherein p is 1 and —C(R$^6$)$_2$)$_p$-heterocycloalkyl is CH$_2$-pyrrolidinyl, R$^1$ is H, R$^3$ is methyl, R$^2$ is —C(O)NR$^9$R$^{10}$, wherein R$^9$ is methyl and R$^{10}$ is (C$_1$-C$_6$) alkyl, wherein the (C$_1$-C$_6$) alkyl is optionally substituted with one or more R$^{11}$, wherein R$^{11}$ is (C$_1$-C$_6$) alkoxy, —OH, —NH$_2$, (C$_1$-C$_6$) alkylamino, (C$_1$-C$_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from (C$_1$-C$_6$) alkyl and OH; and n is 1.

In another embodiment, L is —C(O)NR$^5$—, wherein R$^5$ is H, A is phenyl optionally substituted with one or more R$^4$, wherein R$^4$ is selected from —CF$_3$, CN, methoxy, and —C(R$^6$)$_2$)$_p$-heterocycloalkyl, wherein p is 1 and —C(R$^6$)$_2$)$_p$-heterocycloalkyl is CH$_2$-pyrrolidinyl, R$^1$ is H, R$^3$ is methyl, R$^2$ is —C(O)NR$^9$R$^{10}$, wherein R$^9$ is methyl and R$^{10}$ is ethyl, wherein the ethyl is optionally substituted with one or more R$^{11}$, wherein R$^{11}$ is methoxy, and n is 1. In another embodiment, R$^4$ is selected from —CF$_3$ and —CH$_2$-pyrrolidinyl. In another embodiment, R$^4$ is selected from —CF$_3$ and methoxy. In another embodiment, R$^4$ is selected from —CF$_3$ and —CN.

In another embodiment, L is —NR$^5$C(O)—, wherein R$^5$ is H, A is phenyl optionally substituted with one or more R$^4$, wherein R$^4$ is —OCF$_3$, R$^1$ is H, R$^3$ is methyl, R$^2$ is —C(O)NR$^9$R$^{10}$, wherein R$^9$ is methyl and R$^{10}$ is methyl, and n is 1.

In another embodiment, L is —NR$^5$C(O)—, wherein R$^5$ is H, A is pyridinyl optionally substituted with one or more R$^4$, wherein R$^4$ is —CF$_3$, R$^1$ is H, R$^2$ is (C$_1$-C$_6$) alkyl, —C(O)R$_8$, or —C(O)NR$^9$R$^{10}$, R$^3$ is methyl, R$^8$ is (C$_1$-C$_6$) alkyl, (C$_3$-C$_7$) cycloalkyl, (C$_2$-C$_6$) alkenyl, (C$_1$-C$_3$) alkoxy, (C$_1$-C$_6$) haloalkyl, (C$_1$-C$_6$) haloalkoxy, or 4 to 7-membered heterocycloalkyl comprising 1 to 3 heteroatoms selected from N, O, and S, R$^9$ is H, (C$_1$-C$_6$) alkyl, (C$_1$-C$_6$) haloalkyl, (C$_3$-C$_7$) cycloalkyl, or 4 to 7-membered heterocycloalkyl comprising 1 to 3 heteroatoms selected from N, O, or S, R$^{10}$ is H, (C$_1$-C$_6$) alkyl, (C$_1$-C$_6$) haloalkyl, (C$_3$-C$_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from (C$_1$-C$_6$) alkyl, —NH$_2$, (C$_1$-C$_6$) alkylamino, (C$_1$-C$_6$) dialkylamino, and —OH, and wherein the (C$_1$-C$_6$) alkyl is optionally substituted with one or more R$^{11}$, or R$^9$ and R$^{10}$ together with the nitrogen atom to which they are attached form a 4- to 7-membered heterocycloalkyl ring comprising 1 to 3 heteroatom selected from N, O, and S, optionally substituted with one or more substituent each independently selected from (C$_1$-C$_6$) alkyl, (C$_1$-C$_6$) hydroxyalkyl, —(CH$_2$)$_q$—NH$_2$, —(CH$_2$)$_q$—(C$_1$-C$_6$) alkylamino, —(CH$_2$)$_q$—(C$_1$-C$_6$) dialkylamino, —C(O)(C$_1$-C$_6$) alkyl, —OH, and 4- to 7-membered heterocycloalkyl comprising 1 to 3 heteroatom selected from N, O, and S, and optionally substituted with one or more (C$_1$-C$_6$) alkyl, R$^1$ is (C$_1$-C$_6$) alkoxy, —OH, —NH$_2$, (C$_1$-C$_6$) alkylamino, (C$_1$-C$_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from (C$_1$-C$_6$) alkyl and OH; and n is 1.

In another embodiment, L is —NR$^5$C(O)—, wherein R$^5$ is H, A is pyridinyl optionally substituted with one or more R$^4$, wherein R$^4$ is —CF$_3$, R$^1$ is H, R$^3$ is methyl, R$^2$ is —C(O)NR$^9$R$^{10}$, wherein R$^9$ is methyl and R$^{10}$ is H, (C$_1$-C$_6$) alkyl, (C$_1$-C$_6$) haloalkyl, (C$_3$-C$_7$) cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from (C$_1$-C$_6$) alkyl, —NH$_2$, (C$_1$-C$_6$) alkylamino, (C$_1$-C$_6$) dialkylamino, and —OH, and wherein the (C$_1$-C$_6$) alkyl is optionally substituted with one or more R$^{11}$, wherein R$^{11}$ is (C$_1$-C$_6$) alkoxy, —OH, —NH$_2$, (C$_1$-C$_6$) alkylamino, (C$_1$-C$_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from (C$_1$-C$_6$) alkyl and OH; and n is 1. In another embodiment, R$^{10}$ is H.

In another embodiment, L is —NR$^5$C(O)—, wherein R$^5$ is H, A is pyridinyl optionally substituted with one or more R$^4$, wherein R$^4$ is —CF$_3$, R$^1$ is H, R$^3$ is methyl, R$^2$ is —C(O)NR$^9$R$^{10}$, wherein R$^9$ is methyl and R$^{10}$ is 4 to 7-membered heterocycloalkyl comprising 1 to 3 heteroatoms selected from N, O, or S, wherein the heterocycloalkyl is optionally substituted with one or more substituents each independently selected from (C$_1$-C$_6$) alkyl, —NH$_2$, (C$_1$-C$_6$) alkylamino, (C$_1$-C$_6$) dialkylamino, and —OH, and n is 1. In another embodiment, R$^{10}$ is N-methylpiperidinyl.

In another embodiment, L is —NR$^5$C(O)—, wherein R$^5$ is H, A is pyridinyl substituted with one or more R$^4$, wherein R$^4$ is —CF$_3$, R$^1$ is H, R$^3$ is methyl, R$^2$ is —C(O)NR$^9$R$^{10}$, wherein R$^9$ is H and R$^{10}$ is H, methyl, ethyl, propyl, n-butyl, isobutyl, or cyclopropyl, wherein the methyl, ethyl, propyl, n-butyl, or isobutyl is optionally substituted with one or more R$^{11}$, wherein R$^{11}$ is (C$_1$-C$_6$) alkoxy, —OH, —NH$_2$, (C$_1$-C$_6$) alkylamino, (C$_1$-C$_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from (C$_1$-C$_6$) alkyl and OH; and n is 1.

In another embodiment, L is —NR$^5$C(O)—, wherein R$^5$ is H, A is pyridinyl substituted with one or more R$^4$, wherein R$^4$ is —CF$_3$, R$^1$ is H, R$^3$ is methyl, R$^2$ is —C(O)NR$^9$R$^{10}$, wherein R$^9$ is H and R$^{10}$ is ethyl, wherein ethyl is optionally substituted with one or more R$^{11}$, wherein R$^{11}$ is (C$_1$-C$_6$) alkoxy, —OH, —NH$_2$, (C$_1$-C$_6$) alkylamino, (C$_1$-C$_6$) dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from (C$_1$-C$_6$) alkyl and OH; and n is 1. In another embodiment, R$^{11}$ is methoxy. In another embodiment, R$^{11}$ is N-piperazinyl. In another embodiment, R$^{11}$ is —OH.

In another embodiment, L is —NR$^5$C(O)—, wherein R$^5$ is H, A is pyridinyl substituted with one or more R$^4$, wherein R$^4$ is —CF$_3$, R$^1$ is H, R$^3$ is methyl, R$^2$ is —C(O)NR$^9$R$^{10}$, wherein R$^9$ is H and R$^{10}$ is ethyl, wherein ethyl is optionally substituted with one or more R$^{11}$, wherein R$^{11}$ is (C$_1$-C$_6$) dialkylamino, and n is 1. In another embodiment, R$^1$ is dimethylamino. In another embodiment, R$^{11}$ is diethylamino.

In another embodiment, L is —NR$^5$C(O)—, wherein R$^5$ is H, A is pyridinyl substituted with one or more R$^4$, wherein R$^4$ is —CF$_3$, R$^1$ is H, R$^3$ is (C$_1$-C$_6$) alkyl, (C$_1$-C$_6$) alkoxy, (C$_1$-C$_6$) haloalkyl, (C$_1$-C$_6$) haloalkoxy, halogen, or OH, R$^2$ is —C(O)NR$^9$R$^{10}$, wherein R$^9$ is H and R$^{10}$ is ethyl, wherein the ethyl is optionally substituted with one or more R$^{11}$, wherein R$^{11}$ is methoxy, and n is 0 or 1.

In another embodiment, L is —NR$^5$C(O)—, wherein R$^5$ is H, A is pyridinyl substituted with one or more R$^4$, wherein R$^4$ is —CF$_3$, R$^1$ is H, R$^3$ is fluoro, R$^2$ is —C(O)NR$^9$R$^{10}$, wherein R$^9$ is H and R$^{10}$ is ethyl, wherein the ethyl is optionally substituted with one or more R$^{11}$, wherein R$^{11}$ is methoxy, and n is 1.

In another embodiment, L is —NR$^5$C(O)—, wherein R$^5$ is H, A is pyridinyl substituted with one or more R$^4$, wherein R$^4$ is —CF$_3$, R$^1$ is H, R$^2$ is —C(O)NR$^9$R$^{10}$, wherein R$^9$ is H and R$^{10}$ is ethyl, wherein the ethyl is optionally substituted with one or more R$^{11}$, wherein R$^{11}$ is methoxy, and n is 0.

Non-limiting illustrative compounds of the invention include:

3-((2-(3,3-dimethylureido)thiazol-5-yl)ethynyl)-4-methyl-N-(4-(trifluoromethyl)pyridin-2-yl)benzamide (I-1);
4-methyl-N-(4-(trifluoromethyl)pyridin-2-yl)-3-((2-ureidothiazol-5-yl)ethynyl)benzamide (I-2);
methyl (5-((2-methyl-5-((4-(trifluoromethyl)pyridin-2-yl)carbamoyl)phenyl)ethynyl)thiazol-2-yl)carbamate (I-3);
4-methyl-3-((2-(3-methylureido)thiazol-5-yl)ethynyl)-N-(4-(trifluoromethyl)pyridin-2-yl)benzamide (I-4);
3-((2-(3-(2-methoxyethyl)ureido)thiazol-5-yl)ethynyl)-4-methyl-N-(4-(trifluoromethyl)pyridin-2-yl)benzamide (I-5);
4-methyl-3-((2-(3-(2-morpholinoethyl)ureido)thiazol-5-yl)ethynyl)-N-(4-(trifluoromethyl)pyridin-2-yl)benzamide (I-6);
3-((2-(3-(2-methoxyethyl)-3-methylureido)thiazol-5-yl)ethynyl)-4-methyl-N-(4-(trifluoromethyl)pyridin-2-yl)benzamide (I-7);
3-((2-(3-ethyl-3-methylureido)thiazol-5-yl)ethynyl)-4-methyl-N-(4-(trifluoromethyl)pyridin-2-yl)benzamide (I-8);
3-((2-(3-(2-(dimethylamino)ethyl)-3-methylureido)thiazol-5-yl)ethynyl)-4-methyl-N-(4-(trifluoromethyl)pyridin-2-yl)benzamide (I-9);
3-((2-(3-(2-hydroxyethyl)-3-methylureido)thiazol-5-yl)ethynyl)-4-methyl-N-(4-(trifluoromethyl)pyridin-2-yl)benzamide (I-10);
3-((2-(3-(2-(dimethylamino)ethyl)ureido)thiazol-5-yl)ethynyl)-4-methyl-N-(4-(trifluoromethyl)pyridin-2-yl)benzamide (I-11);
4-methyl-3-((2-(3-(2-(pyrrolidin-1-yl)ethyl)ureido)thiazol-5-yl)ethynyl)-N-(4-(trifluoromethyl)pyridin-2-yl)benzamide (I-12);
4-methyl-3-((2-(3-((1-methylpiperidin-4-yl)methyl)ureido)thiazol-5-yl)ethynyl)-N-(4-(trifluoromethyl)pyridin-2-yl)benzamide (I-13);
4-methyl-3-((2-(3-(2-(4-methylpiperazin-1-yl)ethyl)ureido)thiazol-5-yl)ethynyl)-N-(4-(trifluoromethyl)pyridin-2-yl)benzamide (I-14);
3-((2-(3-(2-hydroxy-2-methylpropyl)ureido)thiazol-5-yl)ethynyl)-4-methyl-N-(4-(trifluoromethyl)pyridin-2-yl)benzamide (I-15);
4-methyl-3-((2-(3-methyl-3-(2-(4-methylpiperazin-1-yl)ethyl)ureido)thiazol-5-yl)ethynyl)-N-(4-(trifluoromethyl)pyridin-2-yl)benzamide (I-16);
3-((2-(3-cyclopropylureido)thiazol-5-yl)ethynyl)-4-methyl-N-(4-(trifluoromethyl)pyridin-2-yl)benzamide (I-17);
3-((2-(3-(2-(3-hydroxypyrrolidin-1-yl)ethyl)ureido)thiazol-5-yl)ethynyl)-4-methyl-N-(4-(trifluoromethyl)pyridin-2-yl)benzamide (I-18);
4-methyl-3-((2-(3-methyl-3-(2-(pyrrolidin-1-yl)ethyl)ureido)thiazol-5-yl)ethynyl)-N-(4-(trifluoromethyl)pyridin-2-yl)benzamide (I-19);
4-methyl-3-((2-(3-methyl-3-((1-methylpyrrolidin-2-yl)methyl)ureido)thiazol-5-yl)ethynyl)-N-(4-(trifluoromethyl)pyridin-2-yl)benzamide (I-20);
3-((2-(3-(2-hydroxy-2-methylpropyl)-3-methylureido)thiazol-5-yl)ethynyl)-4-methyl-N-(4-(trifluoromethyl)pyridin-2-yl)benzamide (I-21);
3-((2-(3-(4-hydroxycyclohexyl)-3-methylureido)thiazol-5-yl)ethynyl)-4-methyl-N-(4-(trifluoromethyl)pyridin-2-yl)benzamide (I-22);
4-methyl-N-(5-((2-methyl-5-((4-(trifluoromethyl)pyridin-2-yl)carbamoyl)phenyl)ethynyl)thiazol-2-yl)piperazine-1-carboxamide (I-23);
3-hydroxy-3-methyl-N-(5-((2-methyl-5-((4-(trifluoromethyl)pyridin-2-yl)carbamoyl)phenyl)ethynyl)thiazol-2-yl)azetidine-1-carboxamide (I-24);
4-methyl-N-(5-((2-methyl-5-((4-(trifluoromethyl)pyridin-2-yl)carbamoyl)phenyl)ethynyl)thiazol-2-yl)piperidine-1-carboxamide (I-25);
4-methyl-3-((2-(3-(pyridin-4-ylmethyl)ureido)thiazol-5-yl)ethynyl)-N-(4-(trifluoromethyl)pyridin-2-yl)benzamide (I-26);
4-(2-hydroxyethyl)-N-(5-((2-methyl-5-((4-(trifluoromethyl)pyridin-2-yl)carbamoyl)phenyl)ethynyl)thiazol-2-yl)piperazine-1-carboxamide (I-27);
4-methyl-3-((2-(3-methyl-3-(2-(methylamino)ethyl)ureido)thiazol-5-yl)ethynyl)-N-(4-(trifluoromethyl)pyridin-2-yl)benzamide (I-28);
4-methyl-3-((2-(3-methyl-3-(1-methylpiperidin-4-yl)ureido)thiazol-5-yl)ethynyl)-N-(4-(trifluoromethyl)pyridin-2-yl)benzamide (I-29);
N-(5-((2-methyl-5-((4-(trifluoromethyl)pyridin-2-yl)carbamoyl)phenyl)ethynyl)thiazol-2-yl)piperazine-1-carboxamide (I-30);
3-((2-(3-(4-aminobutyl)ureido)thiazol-5-yl)ethynyl)-4-methyl-N-(4-(trifluoromethyl)pyridin-2-yl)benzamide (I-31);
4-methyl-3-((2-(3-methyl-3-(1-methylpiperidin-3-yl)ureido)thiazol-5-yl)ethynyl)-N-(4-(trifluoromethyl)pyridin-2-yl)benzamide (I-32);
3-((2-(3-(4-aminocyclohexyl)-3-methylureido)thiazol-5-yl)ethynyl)-4-methyl-N-(4-(trifluoromethyl)pyridin-2-yl)benzamide (I-33);
2-((dimethylamino)methyl)-N-(5-((2-methyl-5-((4-(trifluoromethyl)pyridin-2-yl)carbamoyl)phenyl)ethynyl)thiazol-2-yl)morpholine-4-carboxamide (I-34);
N-(5-((2-methyl-5-((4-(trifluoromethyl)pyridin-2-yl)carbamoyl)phenyl)ethynyl)thiazol-2-yl)morpholine-4-carboxamide (I-35);
3-((2-(3-(3-aminopropyl)ureido)thiazol-5-yl)ethynyl)-4-methyl-N-(4-(trifluoromethyl)pyridin-2-yl)benzamide (I-36);
4-acetyl-N-(5-((2-methyl-5-((4-(trifluoromethyl)pyridin-2-yl)carbamoyl)phenyl)ethynyl)thiazol-2-yl)piperazine-1-carboxamide (I-37);
3-((2-(3-(2-aminoethyl)ureido)thiazol-5-yl)ethynyl)-4-methyl-N-(4-(trifluoromethyl)pyridin-2-yl)benzamide (I-38);
4-methyl-3-((2-(3-methyl-3-(1-methylazetidin-3-yl)ureido)thiazol-5-yl)ethynyl)-N-(4-(trifluoromethyl)pyridin-2-yl)benzamide (I-39);
3-(dimethyl amino)-N-(5-((2-methyl-5-((4-(trifluoromethyl)pyridin-2-yl)carbamoyl)phenyl)ethynyl)thiazol-2-yl)pyrrolidine-1-carboxamide (I-40);

N-(5-((2-methyl-5-((4-(trifluoromethyl)pyridin-2-yl)carbamoyl)phenyl)ethynyl)thiazol-2-yl)-4-(4-methylpiperazin-1-yl)piperidine-1-carboxamide (I-41);

2-fluoro-5-((2-(3-methylureido)thiazol-5-yl)ethynyl)-N-(4-(trifluoromethyl)pyridin-2-yl)benzamide (I-42);

2-fluoro-N-(4-(trifluoromethyl)pyridin-2-yl)-5-((2-ureidothiazol-5-yl)ethynyl)benzamide (I-43);

3-((2-(3-methylureido)thiazol-5-yl)ethynyl)-N-(4-(trifluoromethyl)pyridin-2-yl)benzamide (I-44);

4-fluoro-3-((2-(3-methylureido)thiazol-5-yl)ethynyl)-N-(4-(trifluoromethyl)pyridin-2-yl)benzamide (I-45);

3-((2-(3-(2-methoxyethyl)-3-methylureido)thiazol-5-yl)ethynyl)-4-methyl-N-(4-(pyrrolidin-1-ylmethyl)-3-(trifluoromethyl)phenyl)benzamide (I-46);

N-(2-methoxy-3-(trifluoromethyl)phenyl)-3-((2-(3-(2-methoxyethyl)-3-methylureido)thiazol-5-yl)ethynyl)-4-methylbenzamide (I-47);

N-(4-cyano-3-(trifluoromethyl)phenyl)-3-((2-(3-(2-methoxyethyl)-3-methylureido)thiazol-5-yl)ethynyl)-4-methylbenzamide (I-48);

3-((2-(cyclopropanecarboxamido)thiazol-5-yl)ethynyl)-4-methyl-N-(4-(trifluoromethyl)pyridin-2-yl)benzamide (I-49);

3-((2-(cyclopropanecarboxamido)thiazol-5-yl)ethynyl)-4-methyl-N-(4-((4-methylpiperazin-1-yl)methyl)-3-(trifluoromethyl)phenyl)benzamide (I-50);

3-((2-acetamidothiazol-5-yl)ethynyl)-4-methyl-N-(4-(trifluoromethyl)pyridin-2-yl)benzamide (I-51);

4-methyl-3-((2-pivalamidothiazol-5-yl)ethynyl)-N-(4-(trifluoromethyl)pyridin-2-yl)benzamide (I-52);

N-(4-methyl-3-((2-(3-methyl-3-(1-methylpiperidin-4-yl)ureido)thiazol-5-yl)ethynyl)phenyl)-4-(trifluoromethyl)picolinamide (I-53);

N-(3-((2-(3-(2-methoxyethyl)-3-methylureido)thiazol-5-yl)ethynyl)-4-methylphenyl)-4-(trifluoromethyl)picolinamide (I-54);

N-(4-methyl-3-((2-(3-methyl-3-(2-(4-methylpiperazin-1-yl)ethyl)ureido)thiazol-5-yl)ethynyl)phenyl)-4-(trifluoromethyl)picolinamide (I-55);

N-(3-((2-(3,3-dimethylureido)thiazol-5-yl)ethynyl)-4-methylphenyl)-3-(trifluoromethoxy)benzamide (I-56);

N-(4-methyl-3-((2-(3-methylureido)thiazol-5-yl)ethynyl)phenyl)-4-(trifluoromethyl)picolinamide (I-57);

N-(3-((2-(3-(2-(dimethylamino)ethyl)-3-methylureido)thiazol-5-yl)ethynyl)-4-methylphenyl)-4-(trifluoromethyl)picolinamide (I-58);

N-(3-((2-(3-(2-(diethylamino)ethyl)-3-methylureido)thiazol-5-yl)ethynyl)-4-methylphenyl)-4-(trifluoromethyl)picolinamide (I-59);

N-(3-((2-(3-(2-hydroxyethyl)-3-methylureido)thiazol-5-yl)ethynyl)-4-methylphenyl)-4-(trifluoromethyl)picolinamide (I-60);

N-(3-((2-(3-(2-methoxyethyl)-3-methylureido)thiazol-5-yl)ethynyl)phenyl)-4-(trifluoromethyl)picolinamide (I-61); and N-(4-fluoro-3-((2-(3-(2-methoxyethyl)-3-methylureido)thiazol-5-yl)ethynyl)phenyl)-4-(trifluoromethyl)picolinamide (I-62).

In another embodiment of the invention, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula (I) may form salts which are also within the scope of this invention. Reference to a compound of the Formula herein is understood to include reference to salts thereof, unless otherwise indicated.

The present invention relates to compounds which are modulators of c-Kit. In one embodiment, the compounds of the present invention are inhibitors of c-Kit.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Starting materials are either commercially available or made by known procedures in the reported literature or as illustrated. Compounds of the present invention can be synthesized by following the steps outlined in General Scheme 1 which comprise the assembling of (thiazol-2-yl)-carbamates or -ureas. Starting materials are either commercially available or made by known procedures in the reported literature or as illustrated.

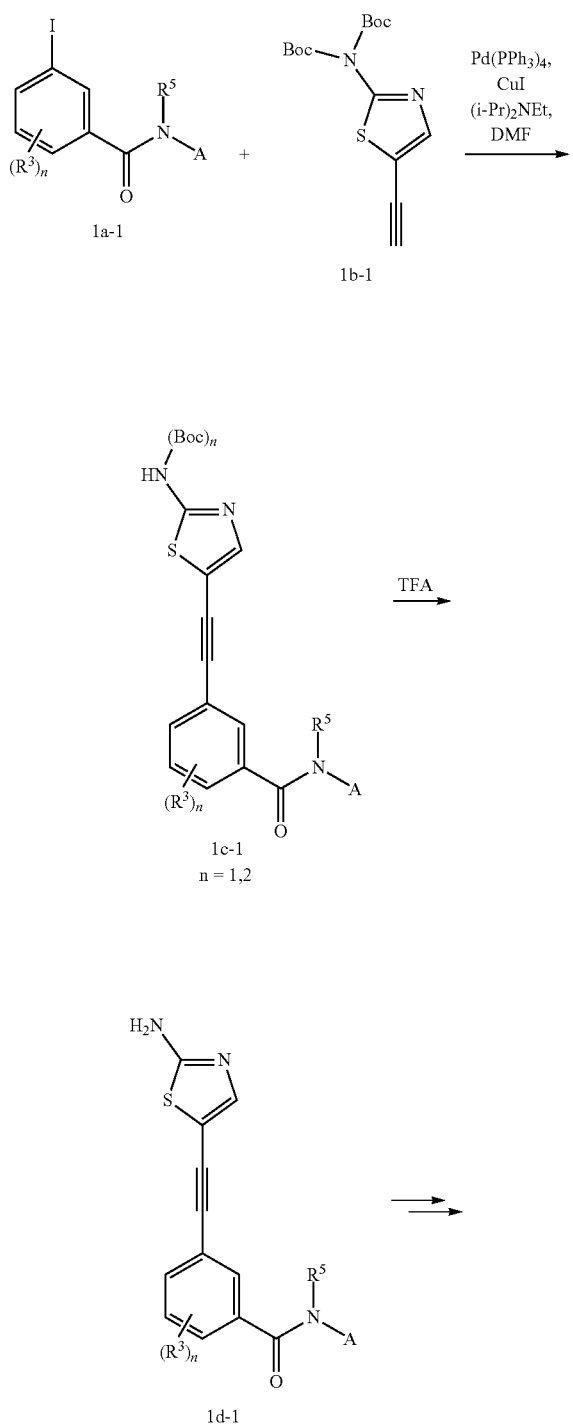

General Scheme 1

-continued

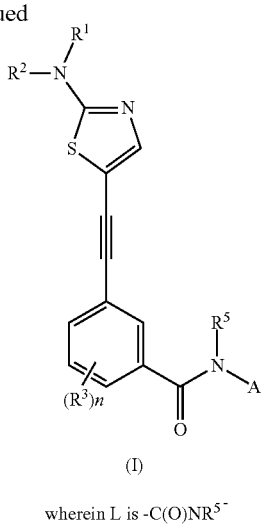

wherein L is -C(O)NR$^5$- wherein A, R$^1$-R$^3$, and R$^5$ and n are defined as in Formula (I).

The general manner of preparing target compounds of Formula (I) wherein L is —C(O)NR$^5$— by using intermediates 1a-1 and 1b-1, is outlined above in General Scheme 1. Coupling of 1a-1 to 1b-1 in the presence of a palladium (0) catalyst and a base, e.g., diisopropylethylamine (DIPEA), in a solvent (e.g., dimethylformamide (DMF), dimethylsulfoxide (DMSO), etc.) optionally at elevated temperature provides intermediate 1c-1. Deprotection in the presence of a strong acid (e.g., trifluoroacetic acid) and a solvent (e.g., dichloromethane (DCM)). Derivatization before or after the coupling step provides the desired product of Formula (I).

Compounds of Formula (I) can exist as enantiomeric or diastereomeric stereoisomers. Enantiomerically pure compounds of Formula (I) can be prepared using enantiomerically pure chiral building blocks. Alternatively, racemic mixtures of the final compounds or a racemic mixture of an advanced intermediate can be subjected to chiral purification as described herein below to deliver the desired enantiomerically pure intermediates or final compounds. In the instances where an advanced intermediate is purified into its individual enantiomers, each individual enantiomer can be carried on separately to deliver the final enantiomerically pure compounds of Formula (I).

It should be understood that in the description and formula shown above, the various groups R$^1$-R$^{11}$, L, A, n, p, and q and other variables are as defined above, except where otherwise indicated. Furthermore, for synthetic purposes, the compounds of General Scheme 1 are merely representative with elected radicals to illustrate the general synthetic methodology of the compounds of Formula (I) as defined herein.

Methods of Using the Disclosed Compounds

Another aspect of the invention relates to a method of treating a disease or disorder associated with modulation of c-Kit. The method comprises administering to a patient in need of a treatment for a disease or disorder associated with modulation of c-Kit an effective amount the compositions and compounds of Formula (I).

Another aspect of the invention relates to a method of preventing a disease or disorder associated with modulation of c-Kit. The method comprises administering to a patient in need of a treatment for a disease or disorder associated with modulation of c-Kit an effective amount the compositions and compounds of Formula (I).

Another aspect of the invention relates to a method of treating a c-Kit-mediated disease or disorder. The method comprises administering to a patient in need of a treatment of a disease or disorder associated with modulation of c-Kit an effective amount the compositions and compounds of Formula (I).

Another aspect of the invention relates to a method of preventing a c-Kit-mediated disease or disorder. The method comprises administering to a patient in need of a treatment for diseases or disorders associated with modulation of c-Kit an effective amount the compositions and compounds of Formula (I).

In another aspect, the present invention is directed to a method of inhibiting c-Kit. The method involves administering to a patient in need thereof an effective amount of a compound of Formula (I).

Another aspect of the present invention relates to a method of treating a disease or disorder in a patient associated with the inhibition of c-Kit, the method comprising administering to a patient in need thereof an effective amount of a compound of Formula (I). In one embodiment, the disease or disorder is selected from the group consisting of cancer and cell proliferative disorders, multiple sclerosis, asthma, mastocytosis, inflammatory disorders, allergic reactions, fibrotic disorders, and metabolic disorders.

Another aspect of the present invention relates to a method of preventing a disease or disorder in a patient associated with the inhibition of c-Kit, the method comprising administering to a patient in need thereof an effective amount of a compound of Formula (I).

The present invention also relates to the use of an inhibitor of c-Kit for the preparation of a medicament used in the treatment, prevention, inhibition or elimination of a disease or disorder mediated by c-Kit, wherein the medicament comprises a compound of Formula (I).

In another aspect, the present invention relates to a method for the manufacture of a medicament for treating, preventing, inhibiting, or eliminating a disease or disorder mediated by c-Kit, wherein the medicament comprises a compound of Formula (I).

Another aspect of the present invention relates to a compound of Formula (I) for use in the manufacture of a medicament for treating a disease or disorder associated with inhibiting c-Kit.

In another aspect, the present invention relates to the use of a compound of Formula (I) in the treatment of a disease or disorder associated with inhibiting c-Kit.

In another aspect, the present invention relates to the use of a compound of Formula (I) in the prevention of a disease or disorder associated with inhibiting c-Kit.

In some embodiments of the methods above, the disease or disorder is selected from the group consisting of cancer, metastasis, inflammation and auto-immune pathogenesis.

In some embodiments of the methods above, the disease or disorder is selected from the group consisting of cell proliferative disorder, a fibrotic disorder, and a metabolic disorder.

In an embodiment of the methods above, the disease or disorder is multiple sclerosis.

In an embodiment of the methods above, the disease or disorder is asthma. In another embodiment of the methods above, the disease or disorder is mastocytosis.

In an embodiment of the methods above, the disease or disorder is an allergic reaction.

In an embodiment of the methods above, the disease or disorder is inflammatory arthritis.

Another aspect of the invention relates to a method of treating cancer. The method comprises administering to a patient in need thereof an effective amount of a compound of Formula (I).

In some embodiments, the cancer is selected from liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer, Hodgkin lymphoma and diffuse large B-cell lymphoma.

In some embodiments, the cancer is selected from leukemia, mast cell tumor, small cell lung cancer, testicular cancer, cancer of the gastrointestinal tract, cancer of the central nervous system, cancer of the female genital tract, sarcoma of neuroectodermal origin, and Schwann cell neoplasia associated with neurofibromatosis.

In some embodiments, the cancer is selected from small cell lung carcinoma, acute myeloid leukemia (AML), thymic carcinoma, desmoid tumor, neuroblastoma, malignant melanomas, colorectal cancer, systemic mastocytosis (SM), and gastrointestinal stromal tumors (GISTs).

Another aspect of the invention relates to a method of inducing cell cycle arrest, apoptosis in tumor cells, and/or enhanced tumor-specific T cell immunity. The method comprises contacting the cells with an effective amount of a compound of Formula (I).

In one embodiment, the present invention relates to the use of an inhibitor of c-Kit for the preparation of a medicament used in treatment, prevention, inhibition or elimination of a disease or disorder associated with associated with cancer and metastasis.

In some embodiments, administration of a compound of Formula (I) or a pharmaceutical composition comprising a compound of the present invention and a pharmaceutically acceptable carrier induces a change in the cell cycle or cell viability.

Another aspect of the invention relates to a method of treating inflammation. The method comprises administering to a patient in need thereof an effective amount of a compound of Formula (I).

Another aspect of the invention relates to a method of treating auto-immune pathogenesis. The method comprises administering to a patient in need thereof an effective amount of a compound of Formula (I).

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of c-Kit including, cancer, metastasis, inflammation and auto-immune pathogenesis, comprising administering to a patient suffering from at least one of said diseases or disorder a compound of Formula (I).

In one embodiment, are provided methods of treating a disease or disorder associated with modulation of c-Kit including, cancer and metastasis, comprising administering to a patient suffering from at least one of said diseases or disorder a compound of Formula (I).

One therapeutic use of the compounds or compositions of the present invention which inhibit c-Kit is to provide treatment to patients or subjects suffering from cancer, metastasis, inflammation and auto-immune pathogenesis.

Another therapeutic use of the compounds or compositions of the present invention which inhibit c-Kit is to provide treatment to patients or subjects suffering from cancer and metastasis.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on Bruker spectrometers at 400 MHz. Spectra are given in ppm ($\delta$) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 µm 2.1×50 mm; Flow rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins. Abbreviations used in the following examples and elsewhere herein are:

br broad
CDI 1,1'-carbonyldiimidazole
DCM dichloromethane
DIPEA N,N-diisopropyl ethyl amine
DMAP 4-(dimethylamino)pyridine
DMF N,N-dimethylformamide
DMSO dimethyl sulfoxide
EI electron ionization
ESI electrospray ionization
Et ethyl
Et$_3$N triethylamine
EtOAc ethyl acetate
EtOH ethanol
GCMS gas chromatography-mass spectrometry
h hour(s)
HATU 2-(7-Aza-1H-benzotriazole-1-yl)-1,1,3,3-tetramethyluronium hexafluorophosphate
HPLC high-performance liquid chromatography
LCMS liquid chromatography-mass spectrometry
m multiplet
Me methyl
MeOH methanol
MHz megahertz
min minutes
MS molecular sieves
NMR nuclear magnetic resonance
ppm parts per million
PSI Pounds per square inch
s singlet
TBAF tetra-n-butylammonium fluoride
TFA trifluoroacetic acid
THF tetrahydrofuran

Methods for the Synthesis of Compounds of Formula (I)
Method A
Example 1: 3-((2-(3,3-dimethylureido)thiazol-5-yl)ethynyl)-4-methyl-N-(4-(trifluoromethyl)pyridin-2-yl)benzamide (I-1)
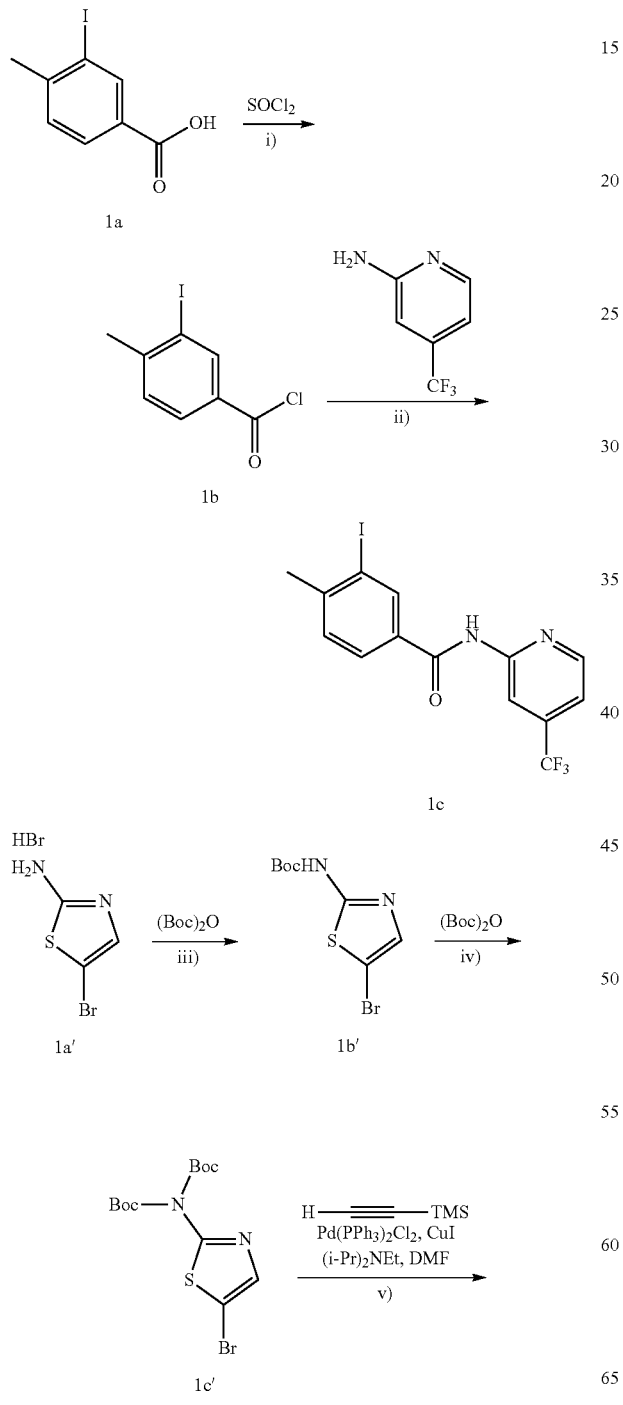
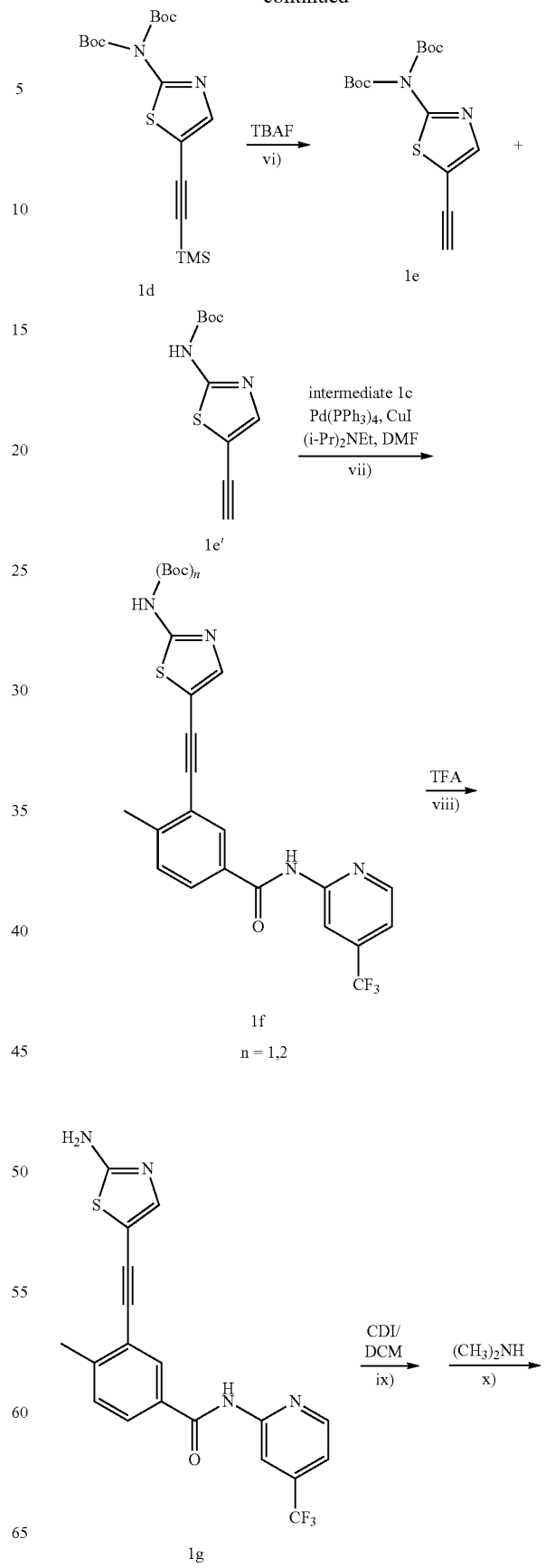

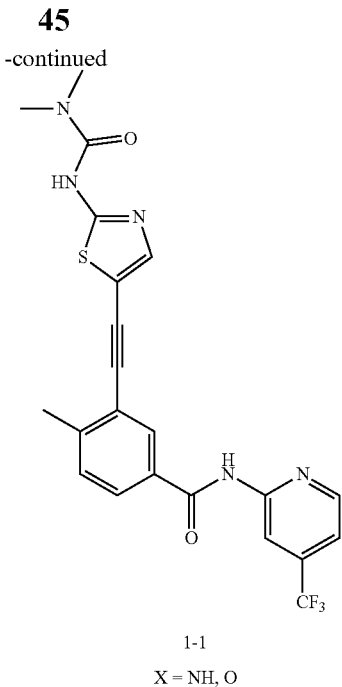

1-1

X = NH, O

Steps i and ii. 3-iodo-4-methyl-N-(4-(trifluoromethyl)pyridin-2-yl)benzamide (1c)

15.72 g (0.06 mol, 1.0 eq) of 3-iodo-4-methylbenzoic acid (1a) in 60 ml of thionyl chloride was refluxed for 1 h. The reaction mixture was evaporated by rotary evaporation to give a brown solid, 1b, which was further dried under high vacuum for 1 h. The solid 1b was then dissolved in 36 ml of THF and carried onto the next step without purification.

To a flask under $N_2$ atmosphere and with stirring was added DMAP (366 mg, 3.0 mmol, 0.05 eq), DIPEA (12.6 ml, 9.36 g, 72 mmol, 1.2 eq), 2-amino-4-(trifluoromethyl)pyridine (9.9 g, 61.2 mmol, 1.02 eq) and THF (120 ml). To this solution was then slowly added solution of an acid chloride (1b, freshly prepared as above) using a funnel under a $N_2$ atmosphere and the reaction mixture was stirred at rt overnight. Water (60 ml) was added, followed by EtOAc (150 ml). The organic layer was separated, and the aqueous layer was extracted with EtOAc (2×100 ml). The combined organic layers were dried, filtered, and concentrated in vacuo. The resulting crude product was purified by flash column chromatography on silica gel (eluting with EtOAc/Heptane 20%) to give intermediate 1c as a white solid.

Steps iii to vi. di-Boc-5-ethynylthiazol-2-amine (1d)

Di-tert-butyl dicarbonate [(Boc)$_2$O, 100.7 g, 0.461 mol, 1.2 eq] was added to a flask containing a mixture of 2-amino-5-bromothiazole monohydrobromide (1a', 100 g, 0.385 mol, 1.0 eq) and 4-(dimethylamino)pyridine (DMAP, 1.18 g, 9.7 mmol, 0.025 eq) in 900 mL of THF and 135 mL of Et$_3$N and cooled to 0° C. using an ice bath. The reaction mixture was stirred at r.t. overnight and then concentrated in vacuo. The residue was stirred in EtOAc/Heptane (1:10, 250 ml) at rt overnight and then filtered. The filtrate was washed with brine, dried, filtered, and concentrated in vacuo to furnish intermediate 1b' as a yellow solid (91% yield).

Di-tert-butyl dicarbonate [(Boc)$_2$O, 90.4 g, 0.414 mol, 1.2 eq] was added to a flask containing a mixture of intermediate 1b' (97.9 g, 0.351 mol, 1.0 eq) and 4-(dimethylamino)pyridine (DMAP, 1.07 g, 8.7 mmol, 0.025 eq) in 880 ml of THF and 121 ml of Et$_3$N and cooled to 0° C. using an ice bath. The reaction mixture was stirred at rt overnight. Water (200 ml) and DCM were added and the resulting mixture was stirred at rt for 30 min. The organic layer was separated and the aqueous layer was extracted with DCM (2×150 ml). The combined organic layers were washed with brine, dried over Na$_2$SO$_4$, filtered and concentrated in vacuo. The crude residue was purified with a short silica gel column (eluting with EtOAc/Heptane 1:20) to give intermediate 1c' as an off-white solid (113 g, 85% yield).

A mixture of the di-Boc material 1b' (48.5 g, 0.128 mol, 1.0 eq), trimethylsilylacetylene (21.8 ml, 15.1 g, 154 mmol, 1.29 eq), Pd(PPh$_3$)$_2$Cl$_2$ (4.7 g), CuI (1.5 g), and Et$_3$N (50 ml) in 200 ml of DMF was heated at 70° C. in a sealed tube under an $N_2$ atmosphere and the resulting mixture was stirred for 1.5 h. After concentrating the reaction mixture in vacuo, sat. aq. Na$_2$CO$_3$ and DCM were added to the crude residue. The organic layer was separated and the combined organic layers were concentrated in vacuo. Purification by flash column chromatography on silica gel (eluting with EtOAc/Heptane 1:10) gave intermediate 1d as a brown solid (37 g, 78% yield).

TBAF (1.0 M in THF, 108 ml) was slowly dropped to a solution of 1d (37 g, 0.1 mol) in 108 ml of DCM at rt. The resulting mixture was stirred at rt for 1 h and then water and DCM were added. The organic layer was separated and the combined organic layers were concentrated in vacuo. Purification by flash column chromatography on silica gel (eluting with EtOAc/Heptane 10% to 30%) afforded a mixture of intermediates 1e (di-Boc-5-ethynylthiazol-2-amine, 24.5 g, 75% yield) and 1e' (Boc-5-ethynylthiazol-2-amine, 2.1 g, 9% yield).

Steps vii to x. 3-((2-(3,3-dimethylureido)thiazol-5-yl)ethynyl)-4-methyl-N-(4-(trifluoromethyl)pyridin-2-yl)benzamide (I-1)

A mixture of 1e and 1e' (24.5 g, 75.5 mmol, 1.0 eq), intermediate 1c (31.4 g, 77.3 mmol, 1.02 eq), Pd(PPh$_3$)$_4$ (7.2 g), CuI (2.05 g), and DIPEA (72.5 ml) in 153 ml of DMF was heated at 100° C. under an atmosphere of $N_2$ and stirred for 3 h. After cooling to r.t., the mixture was evaporated in vacuo. Water and DCM were added with stirring. The organic layer was separated and the aqueous layer was extracted with DCM (2×100 ml). The combined organic layers were washed with brine, dried, filtered, and concentrated in vacuo to furnish a yellow solid (1f, 50 g).

The yellow solid 1f obtained above was dissolved in 200 ml of DCM and 200 ml of TFA was then added. The resulting mixture was stirred at rt for 1 h and then concentrated in vacuo. DCM and sat. aq. Na$_2$CO$_3$ were added with stirring and cooling using an ice bath until a pH of 9-10 was obtained. The organic layer was separated and the aqueous layer was extracted with DCM (2×100 ml). The combined organic layers were washed with brine, dried, filtered, and concentrated to give a yellow solid, which was purified by flash column chromatography on silica gel (MeOH/DCM 1:20) furnishing intermediate 1g as a yellow solid (20 g, 62% yield for two steps). $^1$H NMR (CD$_3$OD): δ 2.33 (3H, s), 7.03 (1H, s), 7.21 (1H, d), 7.24 (1H, d), 7.67 (1H, d), 7.85 (1H, d), 8.39 (2H, d). ESI-MS m/z: 401.1 [M−1]$^−$.

A solution of intermediate 1g (80 mg) and 1,1'-carbonyldiimidazole (CDI, 80 mg) in DCM (4 ml) was stirred at 50° C. overnight and then cooled to r.t. To the resulting suspension was added dimethylamine (2.0 M in THF, 5 eq.). The mixture was stirred at rt for 2 h, and then filtered. The filtrate was concentrated and then purified by prep HPLC to furnish the title compound I-1 (52% yield).

The compounds in Table 1 were synthesized as described in Method A above using the corresponding iodopyridinyl- or iodophenylbenzamides and di-Boc-5-ethynylthiazol-2-amine in step vii, and the corresponding alcohol or amine in step x.

TABLE 1

| Cmpd No. | Compound Structure | Amine/alcohol in step x. | Yield (%) | 1H NMR (400 MHz) ppm; ESI-MS m/z |
|---|---|---|---|---|
| I-1 | 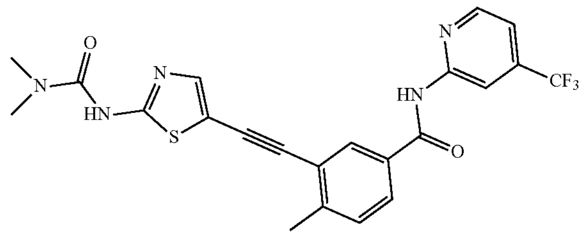 [SMILES: Cc1ccc(C(=O)Nc2cc(C(F)(F)F)ccn2)cc1C#Cc1cnc(NC(=O)N(C)C)s1] | (CH3)2NH | 53 | (CD3OD): 8.45-8.51 (m, 2H), 7.98 (d, J = 2.01 Hz, 1H), 7.78 (dd, J = 7.97, 1.94 Hz, 1H), 7.46 (s, 1H), 7.33 (d, J = 8.44 Hz, 1H), 7.30 (d, J = 5.30 Hz, 1H), 2.95 (s, 6H), 2.44 (s, 3H); [M + H]+ 474. |
| I-2 | 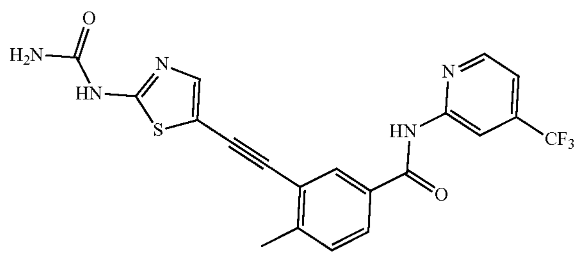 [SMILES: Cc1ccc(C(=O)Nc2cc(C(F)(F)F)ccn2)cc1C#Cc1cnc(NC(N)=O)s1] | NH3 | 21 | (CD3OD): 8.61 (d, J = 4.69 Hz, 2H), 8.12 (d, J = 5.21 Hz, 1H), 7.92 (dd, J = 7.55 Hz, 1H), 7.58 (s, 1H), 7.42-7.51 (m, 2H), 2.58 (s, 3H); [M + H]+ 446. |
| I-3 | 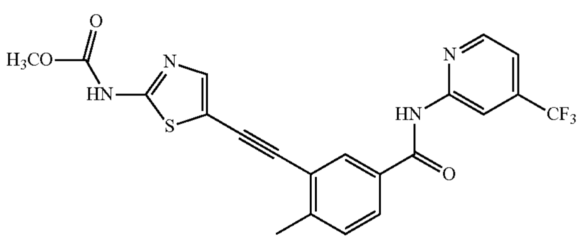 [SMILES: COC(=O)Nc1ncc(C#Cc2cc(C(=O)Nc3cc(C(F)(F)F)ccn3)ccc2C)s1] | CH3OH | 25 | (CD3OD): 8.61 (d, J = 3.68 Hz, 2H), 8.13 (d, J = 2.01 Hz, 1H), 7.94 (d, J = 1.88 Hz, 1H), 7.61 (s, 1H), 7.47 (s, 1H), 7.43 (d, J = 4.86 Hz, 1H), 3.87 (s, 3H) 2.58 (s, 3H); [M + H]+ 461. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-4 | 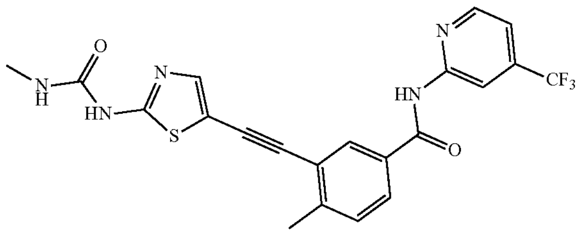 [SMILES: CNC(=O)Nc1ncc(C#Cc2cc(C(=O)Nc3cc(C(F)(F)F)ccn3)ccc2C)s1] | CH₃NH₂ | 51 | (CD₃OD): 8.44 (br s, 2H), 7.95 (d, J = 1.76 Hz, 1H), 7.75 (dd, J = 8.03, 2.01 Hz, 1H), 7.39 (s, 1H), 7.32 (d, J = 8.44 Hz, 1H), 7.26 (d, J = 5.30 Hz, 1H), 2.68 (s, 3H), 2.41 (s, 3H); [M + H]⁺ 460. |
| I-5 | 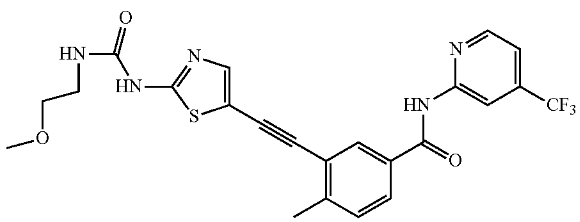 [SMILES: COCCNC(=O)Nc1ncc(C#Cc2cc(C(=O)Nc3cc(C(F)(F)F)ccn3)ccc2C)s1] | CH₃OCH₂CH₂NH₂ | 39 | (CD₃OD): 8.60 (s, 2H), 8.12 (d, J = 2.01 Hz, 1H), 7.87-7.93 (m, 1H), 7.57 (s, 1H), 7.48 (d, J = 8.03 Hz, 1H), 7.43 (d, J = 5.65 Hz, 1H), 3.55 (d, J = 7.98 Hz, 2H), 3.46 (d, J = 7.99 Hz, 2H), 3.41 (s, 3H), 2.58 (s, 3H); [M + H]⁺ 504. |
| I-6 | 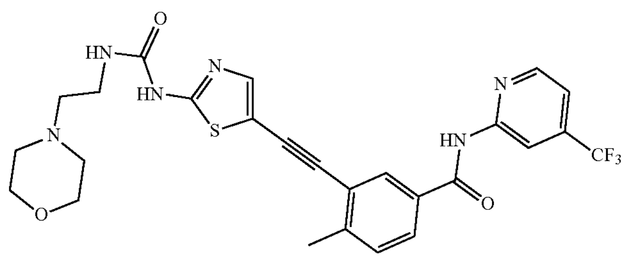 [SMILES: Cc1ccc(C(=O)Nc2cc(C(F)(F)F)ccn2)cc1C#Cc1cnc(NC(=O)NCCN2CCOCC2)s1] | | 51 | (CD₃OD): 8.61 (s, 1H), 8.11 (d, J = 2.01 Hz, 1H), 7.92 (dd, J = 8.20 Hz, 1H), 7.66 (s, 1H), 7.59 (s, 1H), 7.41-7.49 (m, 2H), 4.09 (br s, 2H), 3.81 (br. s., 2H), 3.71 (t, J = 5.77 Hz, 4H), 3.38 (t, J = 5.70, 2H), 3.23 (br s, 2H), 2.57 (s, 3H); [M + H]⁺ 559. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-7 | (structure) | (2-methoxyethyl)(methyl)amine | 63 | (CDCl₃): 9.58 (br s, 1H), 8.76 (br s., 1H), 8.61 (s, 1H), 8.40 (d, J = 5.14 Hz, 1H), 7.93 (d, J = 1.88 Hz, 1H), 7.72 (dd, J = 7.97, 1.94 Hz, 1H), 7.51 (s, 1H), 7.30 (d, J = 8.03 Hz, 1H), 7.22 (d, J = 5.19 Hz, 1H), 3.59 (m, 2H), 3.42-3.49 (m, 2H), 3.39 (s, 3H), 3.00 (s, 3H), 2.47 (s, 3H); [M + H]⁺ 518. |
| I-8 | (structure) | CH₃CH₂NHCH₃ | 55 | (CDCl₃): 9.01 (s, 1H), 8.60 (s, 1H), 8.40 (d, J = 5.02 Hz, 1H), 7.94 (d, J = 1.76 Hz, 1H), 7.74 (dd, J = 7.97, 1.94 Hz, 1H), 7.52 (s, 1H), 7.31 (d, J = 8.16 Hz, 1H), 7.23 (d, J = 5.36 Hz, 1H), 3.30-3.46 (q, J = 7.96 Hz, 2H), 2.95 (s, 3H), 2.47 (s, 3H), 1.14 (t, J = 7.96 Hz, 3H); [M + H]⁺ 488. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-9 | ![structure] | ![amine] | 57 | (CDCl$_3$): 8.85 (s, 1H), 8.71 (s, 1H), 8.49 (d, J = 5.14 Hz, 1H), 8.03 (d, J = 2.01 Hz, 1H), 7.81 (dd, J = 7.91, 2.01 Hz, 1H), 7.59 (s, 1H), 7.39 (d, J = 8.03 Hz, 1H), 7.29 (d, J = 5.46 Hz, 1H), 3.32-3.46 (m, 2H), 3.07 (s, 3H), 2.61-2.74 (m, 2H), 2.56 (s, 3H), 2.47 (s, 6H); [M + H]$^+$ 531. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-10 | (structure) | HO(CH₂)₂NHCH₃ | 38 | (CDCl₃): 8.59-8.63 (m, 2H), 8.41 (d, J = 2.01 Hz, 1H), 7.74 (dd, J = 7.78, 2.01 Hz, 1H), 7.48 (s, 1H), 7.31 (d, J = 7.99 Hz, 1H), 7.22 (d, J = 5.42 Hz, 1H), 3.88 (t, J = 7.89 Hz, 2H), 3.49 (t, J = 7.99 Hz, 2H), 3.04 (s, 3H), 2.49 (s, 3H); [M + H]⁺ 504. |

TABLE 1-continued

| Cmpd No. | Compound Structure | Amine/alcohol in step x. | Yield (%) | $^1$H NMR (400 MHz) ppm; ESI-MS m/z |
|---|---|---|---|---|
| I-11 | (structure) | (structure with NH$_2$ and N(CH$_3$)$_2$) | 23 | (DMSO-d$_6$): 11.30 (s, 1H), 10.82 (s, 1H), 8.66 (d, J = 5.14 Hz, 1H), 8.49 (s, 1H), 8.19 (d, J = 2.01 Hz, 1H), 7.96 (dd, J = 8.03, 2.01 Hz, 1H), 7.62 (s, 1H), 7.44-7.50 (m, 2H), 3.10 (d, J = 5.65 Hz, 2H), 2.53 (s, 3H), 2.38-2.47 (m, 2H), 2.17-2.30 (m, 6H); [M + H]$^+$ 517. |

TABLE 1-continued

| Cmpd No. | Compound Structure | Amine/alcohol in step x. | Yield (%) | $^1$H NMR (400 MHz) ppm; ESI-MS m/z |
|---|---|---|---|---|
| I-12 | [structure: pyrrolidine-ethyl-NH-C(O)-NH-thiazole-C≡C-phenyl(CH3)-C(O)-NH-pyridine-CF3] | [structure: pyrrolidine-CH2CH2-NH2] | 10 | (CD$_3$OD): 12.04-12.16 (m, 2H), 9.50 (d, J = 5.14 Hz, 1H), 9.34 (s, 1H), 9.00 (d, J = 1.76 Hz, 1H), 8.78 (dd, J = 6.16 Hz, 1H), 8.54 (s, 1H), 8.29-8.38 (m, 2H), 7.86 (br s, 1H), 4.30-4.37 (m, 4H), 3.85 (br s, 2H), 2.82 (br s, 2H), 2.69 (br s, 2H); [M + H]$^+$ 543. |

| Cmpd No. | Compound Structure | Amine/alcohol in step x. | Yield (%) | 1H NMR (400 MHz) ppm; ESI-MS m/z |
|---|---|---|---|---|
| I-13 | (structure) | (1-methylpiperidin-4-yl)methanamine | 22 | (DMSO-d6): 11.30 (s, 1H), 10.70 (s, 1H), 8.69 (d, J = 5.14 Hz, 1H), 8.53 (s, 1H), 8.21 (s, 1H), 7.96 (dd, J = 7.97, 1.82 Hz, 1H), 7.70 (s, 1H), 7.58 (d, J = 2.08 Hz, 1H), 7.51 (d, J = 7.99 Hz, 1H), 6.67 (br s, 1H), 3.06 (t, J = 8.01 Hz, 2H), 2.77 (d, J = 8.00, 2H), 2.15 (s, 3H), 1.81 (t, d = 8.06 Hz, 2H), 1.61 (d, J = 8.05 Hz, 2H), 1.40 (m, 1H), 1.11-1.24 (m, 2H); [M + H]+ 557. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-14 | ![structure] | ![amine] | 47 | (DMSO-d6): 11.30 (s, 1H), 10.92 (s, 1H), 8.69 (d, J = 5.14 Hz, 1 H), 8.53 (s, 1H), 8.20 (d, J = 2.01 Hz, 1H), 7.96 (dd, J = 7.97, 1.94 Hz, 1H), 7.70 (s, 1H), 7.54 (dd, J = 5.02, 1.00 Hz, 1H), 7.49 (d, J = 8.03 Hz, 1H), 6.58 (s, 1H), 3.20-3.29 (m, 4H), 2.28-2.37 (m, 8H), 2.17 (s, 3H); [M + H]+ 572. |

TABLE 1-continued

| Cmpd No. | Compound Structure | Amine/alcohol in step x. | Yield (%) | $^1$H NMR (400 MHz) ppm; ESI-MS m/z |
|---|---|---|---|---|
| I-15 | (structure) | (structure with OH and NH₂) | 23 | (DMSO-d$_6$): 11.30 (s, 1H), 10.72 (s, 1H), 8.69 (d, J = 5.14 Hz, 1H), 8.53 (s, 1H), 8.20 (d, J = 2.01 Hz, 1H), 7.96 (dd, J = 8.03, 1.88 Hz, 1H), 7.70 (s, 1H), 7.64 (d, J = 2.02 Hz, 1H), 7.48 (d, J = 7.98 Hz, 1H), 6.66 (s, 1H), 3.10 (d, J = 5.65 Hz, 2H), 1.11 (s, 6H); [M + H]$^+$ 518. |

TABLE 1-continued
| Cmpd No. | Compound Structure | Amine/alcohol in step x. | Yield (%) | $^1$H NMR (400 MHz) ppm; ESI-MS m/z |
|---|---|---|---|---|
| I-16 | 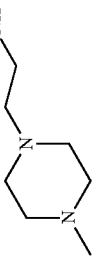 | 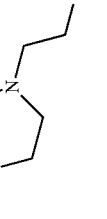 | 65 | (CD$_3$OD): 8.60 (s, 2H), 8.11 (d, J = 2.01 Hz, 1H), 7.91 (dd, J = 8.03, 2.01 Hz, 1H), 7.60 (s, 1H), 7.47 (d, J = 7.62 Hz, 1H), 7.43 (d, J = 5.27 Hz, 1H), 3.52 (m, 2H), 3.06 (s, 3H) 2.63-2.82 (m, 8H), 2.58 (s, 3H), 2.37 (s, 3H); [M + H]$^+$ 586. |

TABLE 1-continued
| Cmpd No. | Compound Structure | Amine/alcohol in step x. | Yield (%) | $^1$H NMR (400 MHz) ppm; ESI-MS m/z |
|---|---|---|---|---|
| I-17 | 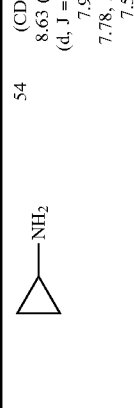 |  | 54 | (CD$_3$OD): 8.59-8.63 (m, 2H), 8.12 (d, J = 2.01 Hz, 1H), 7.92 (dd, J = 7.78, 2.01 Hz, 1H), 7.58 (s, 1H), 7.42-7.50 (m, 2H), 2.63-2.69 (m, 1H), 2.58 (s, 3H), 0.78-0.83 (m, 2H), 0.58 (dd, J = 3.51, 2.01 Hz, 2H); [M + H]$^+$ 486. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-18 | [structure] | [structure] | 36 | (DMSO-d6): 11.31 (s, 1H), 10.85 (s., 1 H), 8.69 (d, J = 5.14 Hz, 1H), 8.53 (s, 1H), 8.19 (s, 1H), 7.92-7.98 (m, 1H), 7.69 (s, 1H), 7.47-7.56 (m, 2H), 6.66 (s, 1H), 4.72 (br s, 2H), 4.23 (br s, 2H), 2.78 (br s, 2H), 2.62-2.72 (m, 2H), 2.40 (br s, 3H), 2.34 (d, J = 1.76 Hz, 2H), 2.19 (m, 1H), 1.58 (br s, 2H); [M + H]+ 586. |

TABLE 1-continued

| Cmpd No. | Compound Structure | Amine/alcohol in step x. | Yield (%) | $^1$H NMR (400 MHz) ppm; ESI-MS m/z |
|---|---|---|---|---|
| I-19 | (structure) | (structure: 2-(pyrrolidin-1-yl)-N-methylethanamine) | 32 | (DMSO-d$_6$): 11.30 (s, 1H), 8.69 (d, J = 5.14 Hz, 1H), 8.53 (s, 1H), 8.19 (d, J = 1.88 Hz, 1H), 7.95 (dd, J = 7.91, 1.88 Hz, 1H), 7.70 (s, 1H), 7.54 (d, J = 5.07 Hz, 1H), 7.49 (d, J = 8.16 Hz, 1H), 3.46 (t, J = 5.33 Hz, 2H), 2.97 (s, 3H), 2.75 (s, 2H), 2.67 (br s, 4H), 1.81 (br s, 4H); [M + H]$^+$ 557. |

TABLE 1-continued

| Cmpd No. | Compound Structure | Amine/alcohol in step x. | Yield (%) | $^1$H NMR (400 MHz) ppm; ESI-MS m/z |
|---|---|---|---|---|
| I-20 | 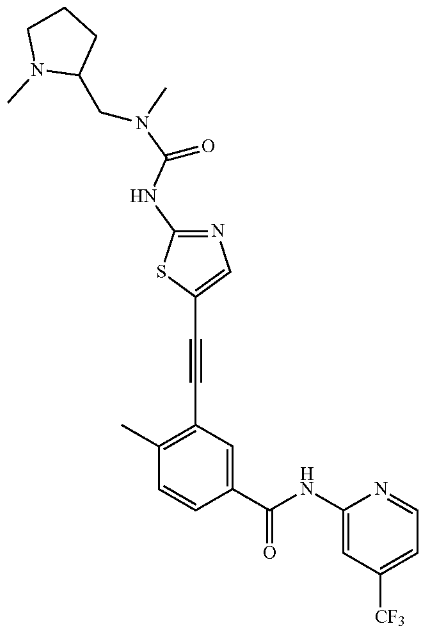 [SMILES: Cc1ccc(C(=O)Nc2cc(C(F)(F)F)ccn2)cc1C#Cc1cnc(NC(=O)N(C)CC2CCCN2C)s1] | | 55 | (DMSO-d$_6$): 11.30 (s, 1H), 8.69 (d, J = 5.14 Hz, 1H), 8.53 (s, 1H), 8.19 (d, J = 1.88 Hz, 1H), 7.95 (dd, J = 7.97, 1.94 Hz, 1H), 7.70 (s, 1H), 7.55 (d, J = 5.23 Hz, 1H), 7.49 (d, J = 8.16 Hz, 1H), 3.60 (br s, 1H), 3.06 (br s, 2H), 2.98 (s, 3H), 1.94 (br s, 2H), 1.79 (br s, 2H), 1.63 (br s, 2H); [M + H]$^+$ 557. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-21 | (structure) | (structure) | 76 | (DMSO-d6) 11.30 (s, 1H), 8.69 (d, J = 5.14 Hz, 1H), 8.53 (s, 1H), 8.20 (d, J = 1.88 Hz, 1H), 7.96 (dd, J = 7.97, 1.94 Hz, 1H), 7.73 (s, 1H), 7.47-7.56 (m, 2H), 3.34 (s, 2H), 3.04 (br s, 3H), 1.08-1.26 (m, 6H); [M + H]+ 532. |

TABLE 1-continued

| Cmpd No. | Compound Structure | Amine/alcohol in step x. | Yield (%) | $^1$H NMR (400 MHz) ppm; ESI-MS m/z |
|---|---|---|---|---|
| I-22 | (structure) | (structure) | 47 | (DMSO-d$_6$) 11.31 (s, 1H), 11.20 (s, 1H), 8.69 (d, J = 5.14 Hz, 1H), 8.54 (s, 1H), 8.20 (d, J = 2.01 Hz, 1H), 7.96 (dd, J = 7.91, 1.88 Hz, 1H), 7.75 (s, 1H), 7.48-7.56 (m, 2H), 4.55 (d, J = 4.64 Hz, 1H), 3.28 (s, 1H), 2.83 (s, 3H), 1.87 (d, J = 11.54 Hz, 2H), 1.55 (d, J = 7.03 Hz, 4H), 1.30 (dd, J = 11.29, 4.52 Hz, 2H); [M + H]$^+$ 558. |

TABLE 1-continued
| Cmpd No. | Compound Structure | Amine/alcohol in step x. | Yield (%) | $^{1}$H NMR (400 MHz) ppm; ESI-MS m/z |
|---|---|---|---|---|
| I-23 | 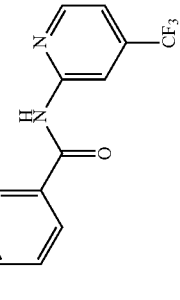 | 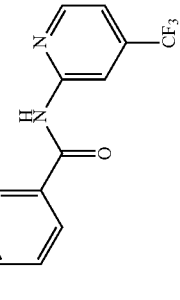 | 28 | (CD$_3$OD): 8.60 (s, 2H), 8.10 (d, J = 1.88 Hz, 1H), 7.92 (dd, J = 7.97, 1.94 Hz, 1H), 7.56 (s, 1H), 7.41-7.49 (m, 2H), 4.53 (br s, 2H), 3.57 (br s, 2H), 3.15 (br s, 2H), 2.97 (s, 3H), 2.57 (s, 3H); [M + H]$^+$ 529. |

TABLE 1-continued

| Cmpd No. | Compound Structure | Amine/alcohol in step x. | Yield (%) | $^1$H NMR (400 MHz) ppm; ESI-MS m/z |
|---|---|---|---|---|
| I-24 | (structure) | (structure) | 29 | (CD$_3$OD): 8.59 (s, 1H), 8.58 (s, 1H), 8.10 (d, J = 1.88 Hz, 1H), 7.91 (dd, J = 7.97, 1.95 Hz, 1H), 7.59 (s, 1H), 7.42-7.48 (m, 2H), 4.01 (s, 4H), 2.56 (s, 3H), 1.52 (s, 3H); [M + H]$^+$ 516 |

TABLE 1-continued
| Cmpd No. | Compound Structure | Amine/alcohol in step x. | Yield (%) | 1H NMR (400 MHz) ppm; ESI-MS m/z |
|---|---|---|---|---|
| I-25 | 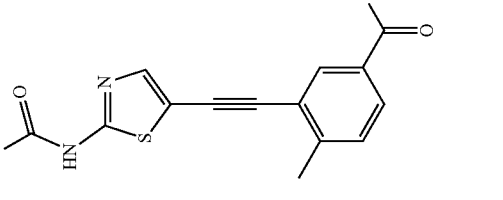 | | 29 | (CD$_3$OD): 8.48-8.56 (m, 2H), 8.02 (d, J = 2.01 Hz, 1H), 7.83 (dd, J = 8.03, 2.01 Hz, 1H), 7.45 (s, 2H), 7.30-7.43 (m, 2H), 3.77-3.87 (m, 1H), 3.46-3.57 (m, 2H), 3.02-3.23 (m, 2H), 2.85 (s, 3H), 2.48 (s, 3H), 2.19 (d, J = 14.93 Hz, 2H), 1.73 (m, 2H); [M + H]$^+$ 543. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-26 | ![structure] | ![4-pyridylmethylamine] | 29 | (CD$_3$OD): 8.60 (d, J = 4.81 Hz, 2H), 8.51 (d, J = 5.03 Hz, 2H), 8.12 (d, J = 2.01 Hz, 1H), 7.92 (dd, J = 8.03, 2.01 Hz, 1H), 7.59 (s, 1H), 7.48 (d, J = 8.03 Hz, 1H), 7.41-7.44 (m, 3H), 4.53-4.55 (m, 2H), 2.57 (s, 3H); [M + H]$^+$ 537. |

TABLE 1-continued
| Cmpd No. | Compound Structure | Amine/alcohol in step x. | Yield (%) | $^1$H NMR (400 MHz) ppm; ESI-MS m/z |
|---|---|---|---|---|
| I-27 | 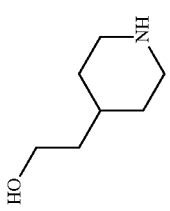 | 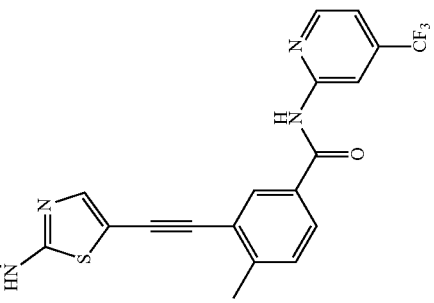 | 41 | (CD$_3$OD): 8.59-8.63 (m, 2H), 8.11 (d, J = 2.01 Hz, 1H), 7.92 (dd, J = 7.97, 1.94 Hz, 1H), 7.57 (s, 1H), 7.47 (d, J = 7.73 Hz, 1H), 7.42-7.44 (m, 1H), 3.69-3.91 (m, 6H), 2.99 (br s, 6H), 2.57 (s, 3H); [M + H]$^+$ 559. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-28 | (structure) | (structure) | 33 | (CD3OD): 8.61 (d, J = 4.52 Hz, 2H), 8.10 (d, J = 1.76 Hz, 1H), 7.92 (dd, J = 8.03, 2.01 Hz, 1H), 7.60 (s, 1H), 7.48 (d, J = 7.75 Hz, 1H), 7.42-7.45 (m, 1H), 3.77 (t, J = 5.52 Hz, 2H), 3.27 (t, J = 5.52 Hz, 2H), 3.15 (s, 3H), 2.77 (s, 3H), 2.57 (s, 3H); [M + H]+ 517. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-29 | 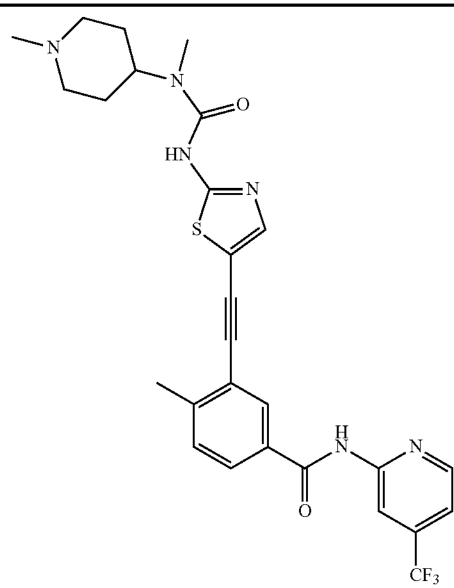 | | 28 | (CD3OD): 8.37-8.41 (m, 2H), 7.89 (d, J = 2.01 Hz, 1H), 7.69 (dd, J = 8.03, 2.01 Hz, 1H), 7.37 (s, 1H), 7.25 (d, J = 7.75 Hz, 1H), 7.21 (d, J = 5.20 Hz, 1H), 3.93-4.02 (m, 1H), 2.73-2.80 (m, 5H), 2.36 (s, 3H), 2.10 (s, 3H), 1.93-2.05 (m, 2H), 1.60-1.74 (m, 2H), 1.37-1.54 (m, 2H); [M + H]+ 557. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-30 | (structure) | (piperazine, piperazine) | 29 | (CD$_3$OD): 8.60 (d, J = 4.70 Hz, 1H), 8.59 (s, 1H), 8.10 (d, J = 2.01 Hz, 1H), 7.91 (dd, J = 8.03, 2.01 Hz, 1H), 7.55 (s, 1H), 7.46 (d, J = 8.35 Hz, 1H), 7.42 (d, J = 5.31 Hz, 1H), 3.85-3.95 (m, 4H), 3.33 (s, 3H), 3.28-3.31 (m, 4H), 2.56 (s, 3H); [M + H]$^+$ 515. |

TABLE 1-continued
| Cmpd No. | Compound Structure | Amine/alcohol in step x. | Yield (%) | $^1$H NMR (400 MHz) ppm; ESI-MS m/z |
|---|---|---|---|---|
| I-31 | 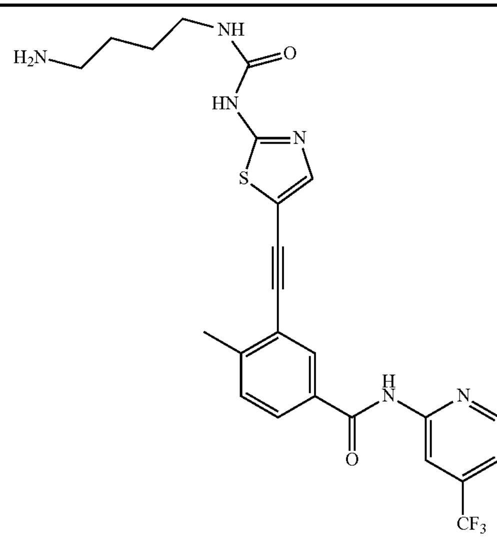 |  | 21 | (CD$_3$OD): 8.61 (s, 1H), 8.60 (s, 1H), 8.11 (d, J = 2.01 Hz, 1H), 7.92 (dd, J = 8.03, 1.88 Hz, 1H), 7.58 (s, 1H), 7.47 (d, J = 7.75 Hz, 1H), 7.43 (d, J = 5.16 Hz, 1H), 7.28 (t, J = 3.00 Hz, 2H), 2.57 (s, 3H), 1.62-1.78 (m, 4H); [M + H]$^+$ 517. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-32 | 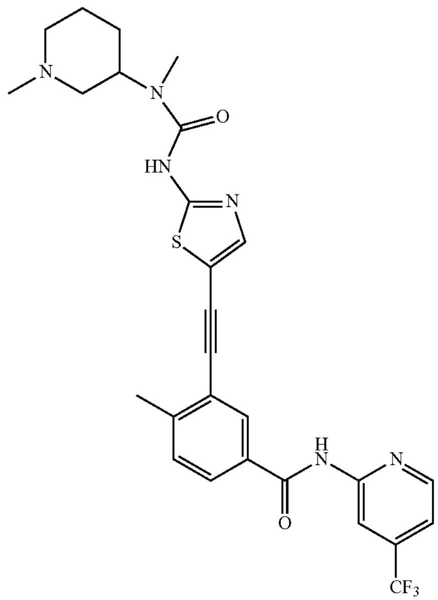 [SMILES: Cc1ccc(C(=O)Nc2cc(C(F)(F)F)ccn2)cc1C#Cc1cnc(NC(=O)N(C)C2CCCN(C)C2)s1] | | 33 | (CD₃OD): 8.58-8.63 (s, 2H), 8.11 (d, J = 2.01 Hz, 1H), 7.92 (dd, J = 7.91, 1.88 Hz, 1H), 7.60 (s, 1H), 7.39-7.52 (m, 2H), 4.51 (m, 1H), 3.50 (m, 2H), 3.20 (t, J = 11.92 Hz, 2H), 3.05 (s, 3H), 2.93 (s, 3H), 2.57 (s, 3H), 2.15 (d, J = 8.28 Hz, 1H), 1.81-2.02 (m, 3H); [M + H]⁺ 557. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-33 | (structure) | (structure) | 58 | (CD₃OD): 8.50-8.54 (m, 2H), 8.03 (d, J = 2.01 Hz, 1H), 7.83 (dd, J = 8.03, 2.01 Hz, 1H), 7.53 (s, 1H), 7.34-7.42 (m, 2H), 4.06-4.15 (m, 1H), 3.01-3.23 (m, 1H), 2.94 (s, 3H), 2.49 (s, 3H), 2.08 (d, J = 12.55 Hz, 2H), 1.72-1.90 (m, 4H), 1.53-1.65 (m, 2H); [M + H]⁺ 557. |

TABLE 1-continued

| Cmpd No. | Compound Structure | Amine/alcohol in step x. | Yield (%) | ¹H NMR (400 MHz) ppm; ESI-MS m/z |
|---|---|---|---|---|
| I-34 | [structure] | [structure] | 12 | (DMSO-d₆) 11.71 (br s, 1H), 11.30 (s, 1H), 8.69 (d, J = 5.14 Hz, 1H), 8.52-8.58 (m, 1H), 8.20 (d, J = 1.88 Hz, 1H), 7.96 (dd, J = 8.03, 1.88 Hz, 1H), 7.76 (s, 1H), 7.64 (s, 1H), 7.43-7.57 (m, 2H), 6.99-7.05 (br s, 1H), 4.16 (d, J = 12.92 Hz, 1H), 4.04 (d, J = 12.92 Hz, 1H), 3.86 (dd, J = 11.61, 2.20 Hz, 1H), 3.34-3.57 (m, 3H), 2.92-3.14 (m, 1H), 2.68 (dd, J = 13.05, 10.67 Hz, 1H), 2.28-2.39 (m, 2H); [M + H]⁺ 585. |

TABLE 1-continued
| Cmpd No. | Compound Structure | Amine/alcohol in step x. | Yield (%) | $^1$H NMR (400 MHz) ppm; ESI-MS m/z |
|---|---|---|---|---|
| I-35 | 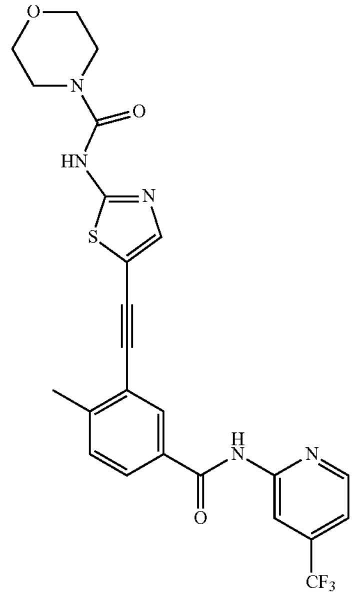 [SMILES: Cc1ccc(C(=O)Nc2cc(C(F)(F)F)ccn2)cc1C#Cc1cnc(NC(=O)N2CCOCC2)s1] |  | 25 | (CD$_3$OD): 8.57-8.64 (m, 2H), 8.11 (d, J = 2.01 Hz, 1H), 7.91 (dd, J = 8.03, 2.01 Hz, 1H), 7.59 (s, 1H), 7.42-7.45 (m, 2H), 3.68-3.77 (m, 4H), 3.55-3.64 (m, 4H), 2.57 (s, 3H); [M + H]$^+$ 516. |

TABLE 1-continued
| Cmpd No. | Compound Structure | Amine/alcohol in step x. | Yield (%) | 1H NMR (400 MHz) ppm; ESI-MS m/z |
|---|---|---|---|---|
| I-36 | 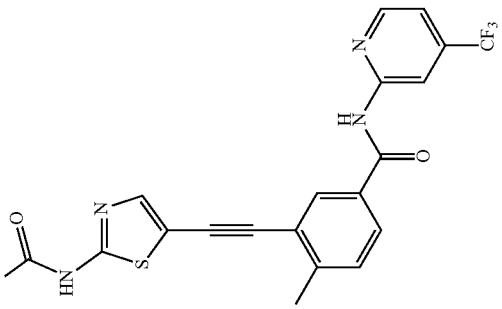 |  | 37 | (CD3OD): 8.60 (s, 1H), 8.59 (s, 1H), 8.10 (d, J = 2.01 Hz, 1H), 7.91 (dd, J = 7.91, 1.88 Hz, 1H), 7.58 (s, 1H), 7.46 (d, J = 7.76 Hz, 1H), 7.43 (d, J = 5.27 Hz, 1H), 3.40 (t, J = 6.65 Hz, 2H), 3.03 (t, J = 7.28 Hz, 2H), 2.56 (s, 3H) 1.85-2.01 (m, 2H); [M + H]+ 503. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-37 | ![structure] | ![structure] | 28 | (CD$_3$OD): 8.58-8.64 (m, 2H), 8.12 (d, J = 1.76 Hz, 1H), 7.92 (dd, J = 6.71 Hz, 1H), 7.60 (s, 1H), 7.43-7.50 (m, 2H), 3.61-3.71 (m, 8H), 2.58 (s, 3H), 2.16 (s, 3H); [M + H]$^+$ 557. |

TABLE 1-continued

| Cmpd No. | Compound Structure | Amine/alcohol in step x. | Yield (%) | $^1$H NMR (400 MHz) ppm; ESI-MS m/z |
|---|---|---|---|---|
| I-38 | (structure) | H₂N-CH₂CH₂-NH₂ | 33 | (CD$_3$OD): 8.60 (s, 1H), 8.59 (s, 1H), 8.09 (d, J = 2.01 Hz, 1H), 7.91 (dd, J = 7.97, 1.94 Hz, 1H), 7.58 (s, 1H), 7.46 (d, J = 8.31 Hz, 1H), 7.42 (d, J = 5.28 Hz, 1H), 3.57 (t, J = 5.83 Hz, 2H), 3.14 (t, J = 5.77 Hz, 2H), 2.56 (s, 3H); [M + H]$^+$ 489. |

TABLE 1-continued
| Cmpd No. | Compound Structure | Amine/alcohol in step x. | Yield (%) | 1H NMR (400 MHz) ppm; ESI-MS m/z |
|---|---|---|---|---|
| I-39 | 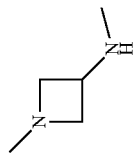 | | 51 | (CD3OD): 8.58 (s, 2H); 8.09 (d, J = 1.76 Hz, 1H); 7.90 (dd, J = 8.03, 2.01 Hz, 1H); 7.62 (s, 1H), 7.34-7.53 (m, 2H), 4.26-4.40 (m, 1H), 4.09-4.21 (m, 1H), 4.03 (dd, J = 10.79, 6.02 Hz, 1H), 3.39-3.52 (m, 2H), 2.99 (s, 3H), 2.84 (s, 3H), 2.55 (s, 3H); [M + H]+ 529. |

TABLE 1-continued
| Cmpd No. | Compound Structure | Amine/alcohol in step x. | Yield (%) | 1H NMR (400 MHz) ppm; ESI-MS m/z |
|---|---|---|---|---|
| I-40 | 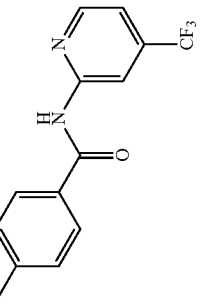 | | 32 | (CD$_3$OD): 8.60 (s, 2H), 8.10 (d, J = 2.01 Hz, 1H), 7.91 (dd, J = 8.03, 2.01 Hz, 1H), 7.55-7.66 (m, 1H), 7.47 (d, J = 7.70 Hz, 1H), 7.43 (d, J = 5.28 Hz, 1H), 3.97-4.09 (m, 2H), 3.84 (ddd, J = 10.54, 8.78, 3.51 Hz, 1H), 3.57-3.74 (m, 2H), 3.00 (s, 6H), 2.47-2.65 (m, 4H), 2.18-2.41 (m, 1H); [M + H]$^+$ 543. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-41 | (structure) | (structure) | 26 | (CD$_3$OD): 8.60 (s, 1H), 8.59 (s, 1H), 8.10 (d, J = 1.76 Hz, 1H), 7.91 (dd, J = 7.91, 1.88 Hz, 1H), 7.58 (s, 1H), 7.46 (d, J = 8.30 Hz, 1H), 7.43 (d, J = 5.23 Hz, 1H), 4.44 (d, J = 13.80 Hz, 2H), 3.57 (br s, 4H), 3.47-3.54 (m, 4H), 3.35-3.45 (m, 1H), 2.95-3.04 (m, 5H), 2.56 (s, 3H), 2.16 (d, J = 10.79 Hz, 2H), 1.62-1.78 (m, 2H); [M + H]$^+$ 612. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-42 | (structure: methylaminocarbonylamino-thiazole-alkyne-fluorobenzamide-N-(4-trifluoromethylpyridin-2-yl)) | CH₃NH₂ | 90 | (CD₃OD): 8.59-8.63 (m, 2H), 7.96 (dd, J = 6.78, 2.26 Hz, 1H), 7.73 (ddd, J = 8.60, 4.83, 2.13 Hz, 1H), 7.55 (s, 1H), 7.45-7.47 (m, 1H), 7.33-7.36 (m, 1H), 2.85 (s, 3H); [M + H]⁺ 464. |
| I-43 | (structure: aminocarbonylamino-thiazole-alkyne-fluorobenzamide-N-(4-trifluoromethylpyridin-2-yl)) | NH₃ | 32 | (CD₃OD): 8.59-8.62 (m, 2H), 7.96 (dd, J = 6.90, 2.13 Hz, 1H), 7.74 (ddd, J = 6.02 Hz, 1H), 7.57 (s, 1H), 7.46 (d, J = 5.38 Hz, 1H), 7.34 (d, J = 2.01 Hz, 1H); [M + H]⁺ 450. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-44 | 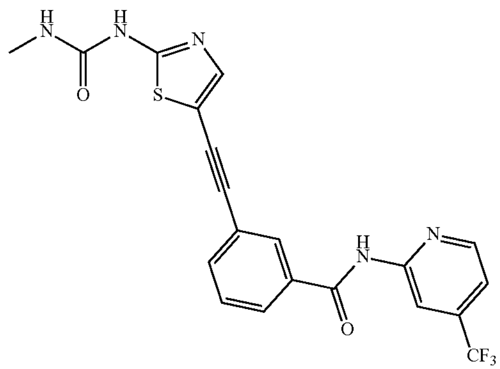 [SMILES: CNC(=O)Nc1ncc(C#Cc2cccc(C(=O)Nc3cc(C(F)(F)F)ccn3)c2)s1] | CH3NH2 | | (CD3OD): 8.59-8.64 (m, 2H), 8.14 (s, 1H), 8.00 (d, J = 7.80 Hz, 1H), 7.74 (d, J = 7.66 Hz, 1H), 7.55-7.60 (m, 2H), 7.44 (d, J = 5.10 Hz, 1H), 3.37 (s, 1H), 2.85 (s, 3H); [M + H]+ 446.0. |
| I-45 | 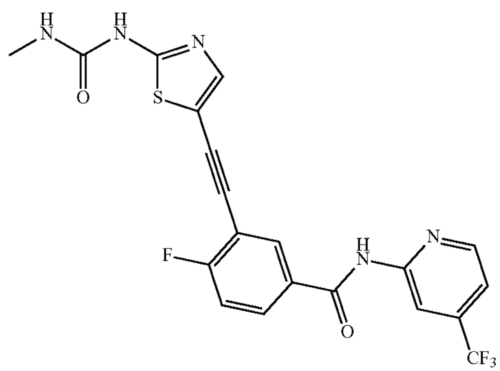 [SMILES: CNC(=O)Nc1ncc(C#Cc2cc(C(=O)Nc3cc(C(F)(F)F)ccn3)ccc2F)s1] | CH3NH2 | | (DMSO-d6): 11.39 (s, 1H), 10.97 (s, 1H), 8.70 (d, J = 5.27 Hz, 1H), 8.51-8.54 (m, 1H), 8.34 (dd, J = 6.90, 2.38 Hz, 1H), 8.10 (ddd, J = 8.72, 4.96, 2.38 Hz, 1H), 7.75 (s, 1H), 7.48-7.59 (m, 2H), 2.72 (d, J = 4.52 Hz, 3H); [M + H]+ 464.0. |

| Cmpd No. | Compound Structure | Amine/alcohol in step x. | Yield (%) | ¹H NMR (400 MHz) ppm; ESI-MS m/z |
|---|---|---|---|---|
| I-46 | 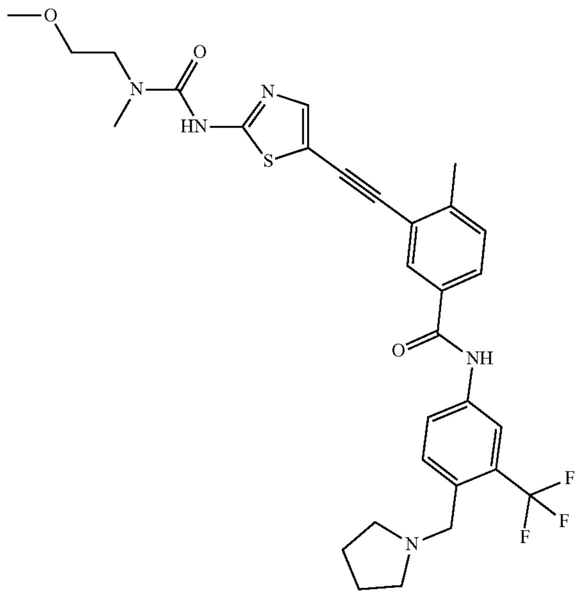 [SMILES: COCCN(C)C(=O)Nc1ncc(C#Cc2cc(C(=O)Nc3ccc(CN4CCCC4)c(C(F)(F)F)c3)ccc2C)s1] | | | (CDCl₃) 12.48-12.73 (m, 1H), 8.70 (s, 1H), 8.47 (d, J = 1.76 Hz, 1H), 8.04 (d, J = 1.51 Hz, 1H), 7.93 (d, J = 8.53 Hz, 1H), 7.86 (dd, J = 1.76, 8.03 Hz, 1H), 7.73 (br d, J = 6.78 Hz, 1H), 7.52 (s, 1H), 7.40 (d, J = 8.03 Hz, 1H), 4.43 (s, 2H), 3.66-3.74 (m, 2H), 3.66-3.74 (m, 2H), 3.60-3.68 (m, 4H), 3.58-3.72 (m, 6H), 3.36-3.44 (m, 3H), 3.11-3.26 (m, 3H), 2.82-2.98 (m, 2H), 2.50-2.60 (m, 3H), 2.04-2.20 (m, 4H); [M + H]⁺ 600.2. |

| Cmpd No. | Compound Structure | Amine/alcohol in step x. | Yield (%) | ¹H NMR (400 MHz) ppm; ESI-MS m/z |
|---|---|---|---|---|
| I-47 | (structure) | (structure) | 50 | (CDCl₃) 8.57 (dd, J = 1.26, 8.03 Hz, 1H), 8.29 (s, 1H), 7.90 (d, J = 2.01 Hz, 1H), 7.69 (dd, J = 2.01, 7.78 Hz, 1H), 7.52 (br s, 1H), 7.25-7.35 (m, 2H), 7.20-7.23 (m, 1H), 3.84 (s, 3H), 3.52-3.59 (m, 2H), 3.43-3.49 (m, 2H), 3.40 (s, 3H), 3.01 (s, 3H), 2.48 (s, 3H); [M + H]⁺ 547.3. |

TABLE 1-continued

| Cmpd No. | Compound Structure | Amine/alcohol in step x. | Yield (%) | 1H NMR (400 MHz) ppm; ESI-MS m/z |
|---|---|---|---|---|
| I-48 | (structure) | (structure) | 17 | (CDCl₃) 9.60 (br s, 1H), 8.78 (s, 1H), 8.22 (d, J = 2.01 Hz, 1H), 8.14 (dd, J = 2.01, 8.53 Hz, 1H), 7.95 (d, J = 2.01 Hz, 1H), 7.84 (d, J = 8.67 Hz, 1H), 7.79 (d, J = 7.64 Hz, 1H), 7.53-7.63 (m, 1H), 7.37 (d, J = 8.03 Hz, 1H), 3.59-3.64 (m, 2H), 3.46-3.54 (m, 2H), 3.43-3.46 (m, 3H), 3.05 (s, 3H), 2.54 (s, 3H); [M + H]⁺ 542.3. |

131

Method B

Example 2: 3-((2-(cyclopropanecarboxamido)thiazol-5-yl)ethynyl)-4-methyl-N-(4-(trifluoromethyl)pyridin-2-yl)benzamide (I-49)

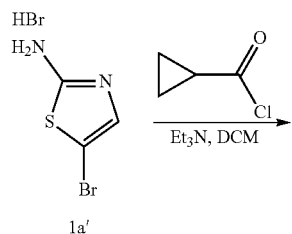

1a'

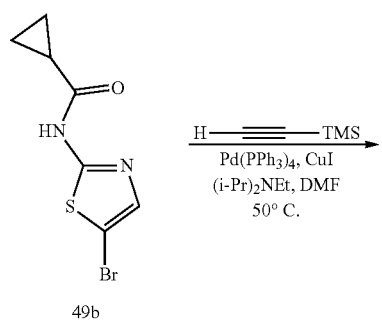

49b

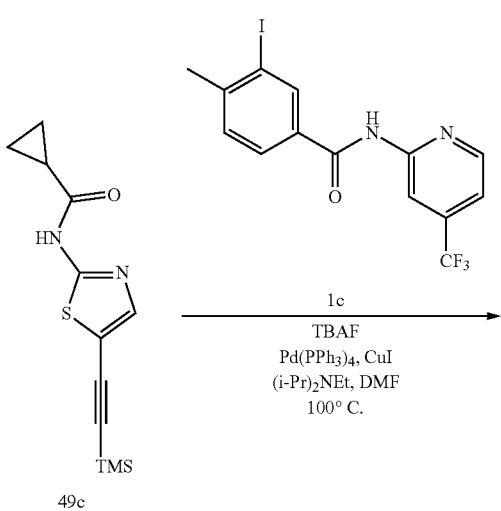

49c

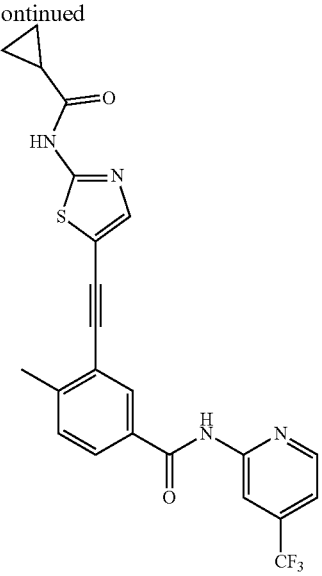

I-49

Step 1. N-(5-bromothiazol-2-yl)cyclopropanecarboxamide (49b)

To a solution of 2-amino-5-bromothiazole monohydrobromide (1a') (5.2 g, 20.0 mmol, 1.0 eq) in 40 ml of DCM was added 4.2 ml of Et$_3$N. To the resulting mixture was slowly added a solution of cyclopropanecarbonyl chloride (1.83 ml, 2.09 g, 20.0 mmol, 1.0 eq) in 10 ml of DCM at −78° C. After stirring at rt for 30 min, an additional 0.5 ml of cyclopropanecarbonyl chloride in 5 ml of DCM was added at −78° C. and the mixture was then stirred at rt for an additional 1 h. Sat. aq. Na$_2$CO$_3$ (15 ml) was added with stirring at rt over 15 min. The organic layers were separated and the aqueous layer was extracted with DCM (1×20 ml). The combined organics were washed with brine, dried over Na$_2$SO$_4$, filtered, and concentrated by rotary evaporation to give a white solid (49b) which was washed with EtOAc, dried under vacuum and then used directly in the next step without purification (3 g, 60%).

Step 2. N-(5-((trimethylsilyl)ethynyl)thiazol-2-yl)cyclopropanecarboxamide (49c)

A sealed tube was charged with N-(5-bromothiazol-2-yl)cyclopropanecarboxamide (49b) (3.0 g, 12.1 mmol, 1.0 eq), Pd(PPh$_3$)$_4$ (583 mg), CuI (191 mg), trimethylsilylacetylene (2.25 ml, 1.57 g, 15.9 mmol, 1.3 eq), DIPEA (2.57 ml) and DMF (25 mL). After degassing with N$_2$, the reaction mixture was stirred at 50° C. overnight. The solvents were removed by rotary evaporation and sat. aq. Na$_2$CO$_3$ and DCM were added. The combined organic layers from extraction were concentrated and the crude mixture was purified by flash column chromatography on silica gel (eluting with EtOAc/Heptane 1:5) to provide intermediate 49c as a yellow solid.

Step 3. 3-((2-(cyclopropanecarboxamido)thiazol-5-yl)ethynyl)-4-methyl-N-(4-(trifluoromethyl)pyridin-2-yl)benzamide (I-49)

A mixture of intermediate 1c (1.727 g, 4.25 mmol, 1.0 eq), intermediate 49c (1.238 g, 4.68 mmol, 1.14 eq), Pd(PPh$_3$)$_4$ (489 mg), CuI (126 mg), DIPEA (6.3 ml) and TBAF (1.0 M in THF, 5.2 ml) in 10 ml of DMF was degassed with N₂ and then heated with stirring at 100° C. overnight. After removing volatiles by rotary evaporation, sat. aq. Na₂CO₃ and DCM were added. The combined organic layers from extraction were concentrated and the crude mixture was purified by flash column chromatography on silica gel (eluting with EtOAc/Heptane 1:5) to provide a yellow solid, which was washed with EtOAc, filtered, and further washed with MeOH to give the title compound I-49 as a light yellow solid.

The compounds in Table 2 were synthesized according to Method B above using the corresponding acyl chloride in step 1 and the corresponding iodopyridinyl- or iodophenyl-benzamides.

TABLE 2

| Cmpd No. | Compound | Acyl chloride in step 1 | ¹H NMR (400 MHz) (δ ppm) | ESI-MS m/z |
|---|---|---|---|---|
| I-49 | | | (DMSO-d₆): 12.74 (br s, 1H), 11.31 (s, 1H), 8.69 (d, J = 5.15 Hz, 1H), 8.53 (s, 1H), 8.21 (d, J = 1.76 Hz, 1H), 7.97 (dd, J = 6.16 Hz, 1H), 7.84 (s, 1H), 7.42-7.62 (m, 2H), 1.93-2.04 (m, 1H), 0.86-1.04 (m, 4H). | [M + H]⁺ 437 |
| I-50 | | | (CD₃OD) 8.15 (d, J = 2.13 Hz, 1H), 8.08 (d, J = 2.01 Hz, 1H), 7.95 (dd, J = 2.07, 8.60 Hz, 1H), 7.87 (dd, J = 1.95, 7.97 Hz, 1H), 7.77 (d, J = 8.41 Hz, 1H), 7.66 (s, 1H), 7.45 (d, J = 8.16 Hz, 1H), 3.69 (s, 2H), 2.69-2.51 (br, s, 11H), 2.39 (s, 3H), 1.88-1.95 (m, 1H), 0.86-1.11 (m, 4H). | [M + H]⁺ 582.2 |

TABLE 2-continued
| Cmpd No. | Compound | Acyl chloride in step 1 | 1H NMR (400 MHz) (δ ppm) | ESI-MS m/z |
|---|---|---|---|---|
| I-51 | | | (DMSO-d6) 12.45 (s, 1H), 11.30 (s, 1H), 8.70 (br s, 1H), 8.54 (s, 1H), 8.22 (d, J = 1.63 Hz, 1H), 7.95-8.03 (m, 1H), 7.84 (s, 1H), 7.47-7.62 (m, 2H), 2.19 (s, 3H). | [M + H]+ 445 |
| I-52 | | | (CDCl3): 9.28 (br s, 1H), 8.79 (br s, 1H), 8.61 (s, 1H), 8.41 (br s, 1H), 7.96 (s, 1H), 7.74 (d, J = 7.98 Hz, 1H), 7.66 (br s, 1H), 7.32 (d, J = 8.03 Hz, 1H), 7.22 (d, J = 5.34 Hz, 1H), 2.48 (s, 3H), 1.28 (s, 9H). | [M + H]+ 487 |
Method C
Example 3: N-(3-((2-(3-(2-(dimethylamino)ethyl)-3-methylureido)thiazol-5-yl)ethynyl)-4-methylphenyl)-4-(trifluoromethyl)picolinamide (I-61)
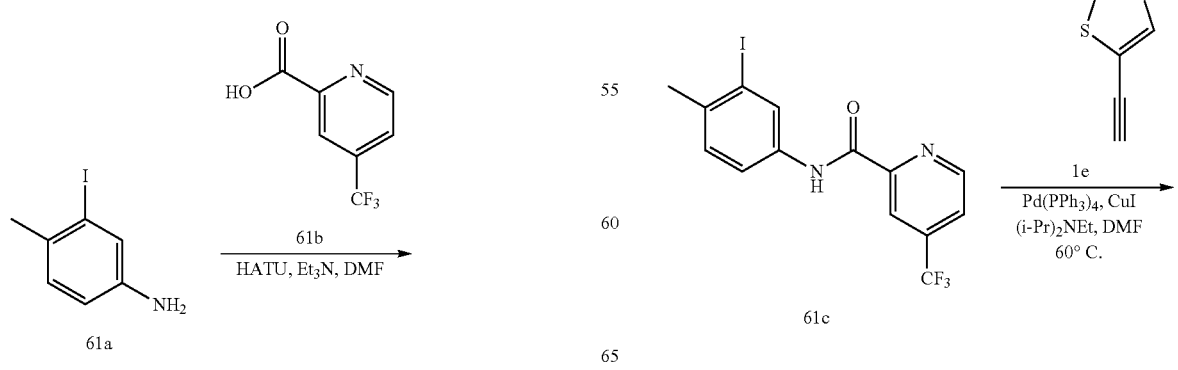

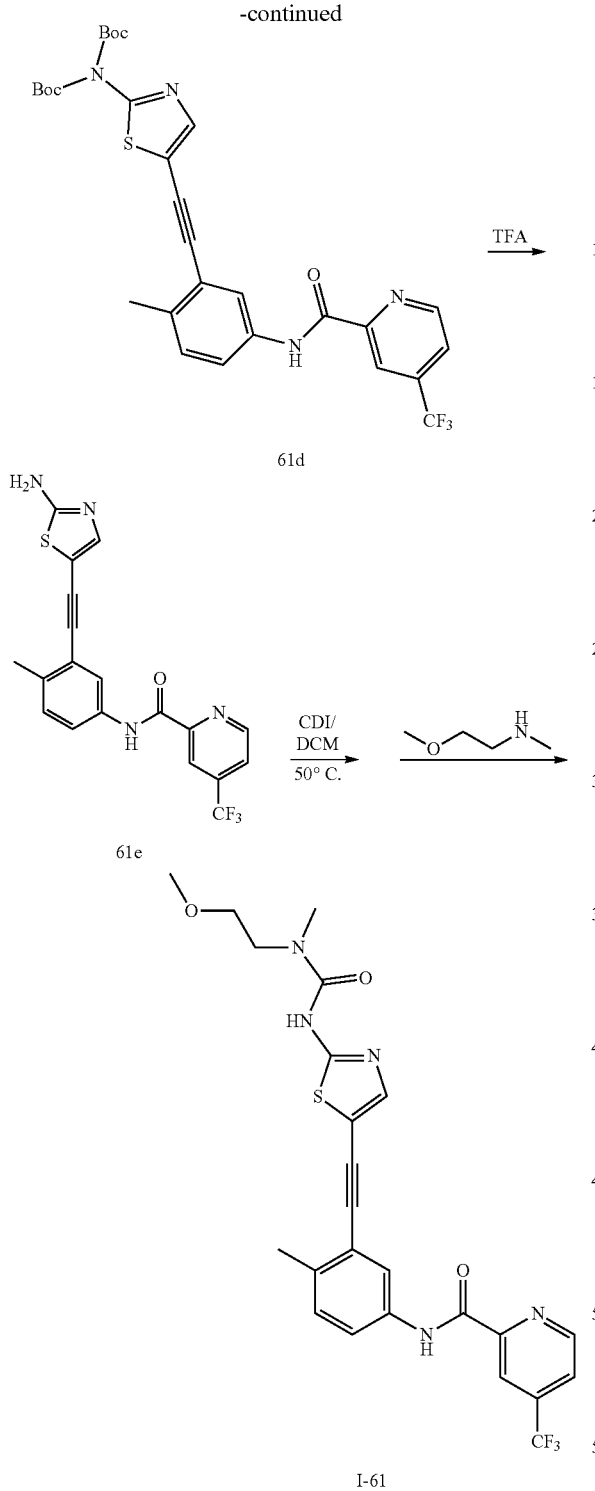

After stirring for 15 min., the solid was collected by filtration and washed with water. The solid product was dried in vacuo to give a white solid (61c, 22 g, 94%).

Step 2. tert-butyl N-tert-butoxycarbonyl-N-[5-[2-[2-methyl-5-[[4-(trifluoromethyl)pyridine-2-carbonyl]amino]phenyl]ethynyl]thiazol-2-yl]carbamate (61d)

A mixture of bis-tert-butyl (5-bromothiazol-2-yl)carbamate 1e (6.2 g), N-(3-iodo-4-methylphenyl)-4-(trifluoromethyl)picolinamide 61c (7.4 g), tetrakis(triphenylphosphine)palladium(0) (1.3 g), and CuI (0.2 g) in DMF (100 mL) was degassed and DIPEA (4.7 mL) was then added. After stirring at 60° C. for 2 h, the mixture was concentrated by rotary evaporation. The resulting residue was dissolved in DCM (200 mL) and washed with water (100 mL). The organic layer was dried, filtered, and concentrated in vacuo. The crude product was purified by flash column chromatography on silica gel (eluting with 10% EtOAc in heptane) to give a solid (61d, 7.5 g, 68%).

Step 3. N-(3-((2-aminothiazol-5-yl)ethynyl)-4-methylphenyl)-4-(trifluoromethyl) picolinamide (61e)

To a solution of tert-butyl N-tert-butoxycarbonyl-N-[5-[2-[2-methyl-5-[[4-(trifluoromethyl)pyridine-2-carbonyl]amino]phenyl]ethynyl]thiazol-2-yl]carbamate 61d (12 g) in DCM (30 ml) was added TFA (30 ml) at room temperature and the resulting mixture was stirred for 1 h. Volatile components were removed by rotary evaporation and the resulting residue was dissolved in DCM (300 mL) and washed with water (100 mL). The organic layer was dried, filtered, and concentrated in vacuo. The crude product was purified by flash column chromatography on silica gel (eluting with 5% MeOH in dichloromethane) to give intermediate 61e as a light brown solid (7.3 g, 91%). $^1$H NMR (400 MHz, CD$_3$OD) δ 8.97-8.99 (d, J=5.15 Hz, 1H), 8.45 (s, 1H), 7.92-7.96 (m, 2H), 7.65-7.68 (dd, J=8.28, 2.38 Hz, 1H), 7.28-7.30 (d, J=8.41 Hz, 1H), 7.22 (s, 1H), 2.45 (s, 3H). EI-MS: [M+H]$^+$ 403.1.

Steps 4 and 5. N-(3-((2-(3-(2-(dimethylamino)ethyl)-3-methylureido)thiazol-5-yl)ethynyl)-4-methylphenyl)-4-(trifluoromethyl)picolinamide (I-61)

To a solution of intermediate 61e (0.07 g) in DCM (20 ml) was added CDI (0.07 g). After the reaction mixture was stirred at 50° C. overnight, N,N,N'-trimethylethylenediamine (0.35 g) was added and then stirred for additional 1 h. After filtration and concentration of the filtrates, the crude product was purified by flash column chromatography on silica gel (eluting with 5% MeOH in dichloromethane) to give the title compound I-61 (0.049 g, 53.1%).

The compounds in Table 3 were synthesized according to Method C above using the corresponding N-(iodophenyl)-4-(trifluoromethyl)picolinamide or N-(3-iodo-4-methylphenyl)-3-(trifluoromethoxy)benzamide in step 2, and the corresponding amine in step 5.

Step 1. N-(3-iodo-4-methylphenyl)-4-(trifluoromethyl)picolinamide (61c)

To a solution of 4-(trifluoromethyl)pyridine-2-carboxylic acid (61b, 11 g) and 3-iodo-4-methyl-aniline (61a, 13.4 g) in DMF (70 mL) was added HATU (26.3 g) and triethylamine (29.6 mL). The resulting mixture was stirred at room temperature overnight and then diluted with water (400 mL).

TABLE 3

| Cmpd No. | Compound Structure | $^1$H NMR (400 MHz): δ (ppm) | ESI-MS m/z |
|---|---|---|---|
| I-53 | 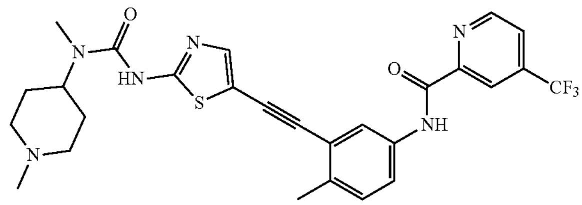 [SMILES: Cc1ccc(NC(=O)c2cc(C(F)(F)F)ccn2)cc1C#Cc1cnc(NC(=O)N(C)C2CCN(C)CC2)s1] | (CDCl$_3$): 9.80 (s, 1H), 8.74 (d, J = 5.02 Hz, 1H), 8.34-8.59 (m, 1H), 8.08 (s, 1H), 7.77 (d, J = 2.26 Hz, 1H), 7.62-7.67 (m, 2H), 7.46 (s, 1H), 7.18 (d, J = 8.00 Hz, 2H), 4.12 (br s, 1H), 2.81-2.90 (m, 5H), 2.39 (s, 3H), 2.18 (s, 3H), 1.92-2.09 (m, 2H), 1.75 (m, 2H), 1.59-1.67 (m, 2H) | [M + H]$^+$ 557.2 |
| I-54 | 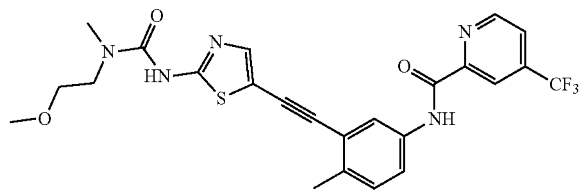 [SMILES: COCCN(C)C(=O)Nc1ncc(C#Cc2cc(NC(=O)c3cc(C(F)(F)F)ccn3)ccc2C)s1] | (CDCl$_3$) 9.89 (s, 1H), 9.54 (br s, 1H), 8.83 (d, J = 5.02 Hz, 1H), 8.56 (s, 1H), 7.84 (d, J = 2.38 Hz, 1H), 7.72-7.78 (m, 2H), 7.56 (s, 1H), 7.26-7.30 (m, 1H), 3.44-3.66 (m, 7H), 3.08 (s, 3H) 2.49 (s, 3H). | [M + H]$^+$ 518.2 |
| I-55 | 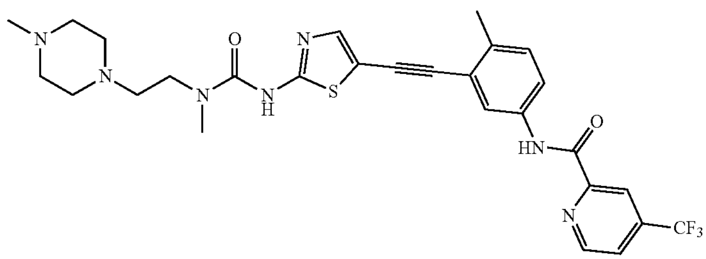 [SMILES: Cc1ccc(NC(=O)c2cc(C(F)(F)F)ccn2)cc1C#Cc1cnc(NC(=O)N(C)CCN2CCN(C)CC2)s1] | (CD$_3$OD) 8.98 (d, J = 5.02 Hz, 1H), 8.46 (s, 1H), 7.98 (s, 1H), 7.93 (d, J = 5.05 Hz, 1H), 7.70 (dd, J = 8.28, 2.26 Hz, 1H), 7.57 (s, 1H), 7.31 (d, J = 8.41 Hz, 1H), 3.49-3.57 (m, 2H), 3.05 (s, 3H), 2.59-2.84 (m, 10H), 2.48 (s, 3H), 2.36 (s, 3H). | [M + H]$^+$ 586.2 |
| I-56 | 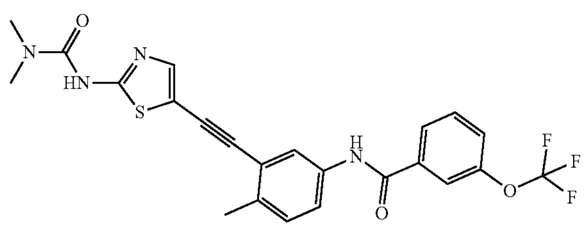 [SMILES: Cc1ccc(NC(=O)c2cccc(OC(F)(F)F)c2)cc1C#Cc1cnc(NC(=O)N(C)C)s1] | (DMSO-d$_6$): 11.06 (br. s., 1H), 10.38 (s, 1H), 8.03 (dt, J = 7.8, 1.2 Hz, 1H), 7.93 (d, J = 2.3 Hz, 2H), 7.60-7.75 (m, 4H), 7.33 (s, 1H), 2.98 (s, 6H), 2.41 (s, 3H). | [M + H]$^+$ 489.1 |
| I-57 | 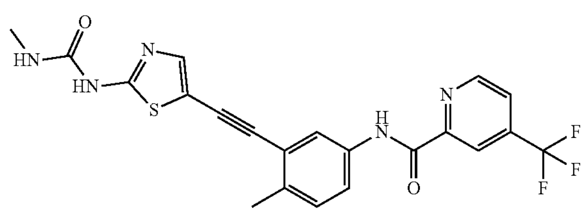 [SMILES: CNC(=O)Nc1ncc(C#Cc2cc(NC(=O)c3cc(C(F)(F)F)ccn3)ccc2C)s1] | (DMSO-d$_6$): 10.85 (s, 2 H) 9.04-9.05 (d, J = 5.14 Hz, 1H) 8.35-8.36 (m, 1H) 8.09-8.11 (d, J = 5.56 Hz, 2H) 7.80-7.83 (dd, J = 8.28, 2.26 Hz, 1H) 7.67 (s, 1H) 7.32-7.34 (d, J = 8.41 Hz, 1H) 2.72 (d, J = 4.64 Hz, 3H) 2.41 (s, 3H). | [M + H]$^+$ 460.0 |
| I-58 | 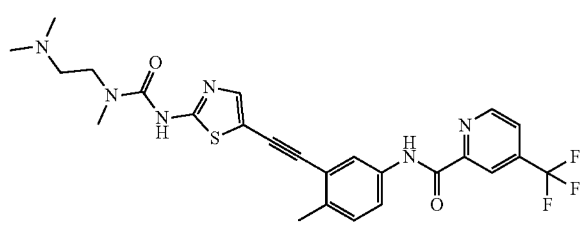 [SMILES: Cc1ccc(NC(=O)c2cc(C(F)(F)F)ccn2)cc1C#Cc1cnc(NC(=O)N(C)CCN(C)C)s1] | (CD$_3$OD): 8.98 (d, J = 5.02 Hz, 1H), 8.39-8.51 (m, 1H), 7.97 (s, 1H), 7.93 (d, J = 5.27 Hz, 1H), 7.69 (dd, J = 2.26, 8.28 Hz, 1H), 7.54 (s, 1H), 7.30 (d, J = 8.28 Hz, 1H), 3.60 (t, 2H), 3.06 (s, 3H), 2.69 (t, J = 5.33 Hz, 2H), 2.36-2.53 (m, 9H). | [M + H]$^+$ 531.2 |
| I-59 | 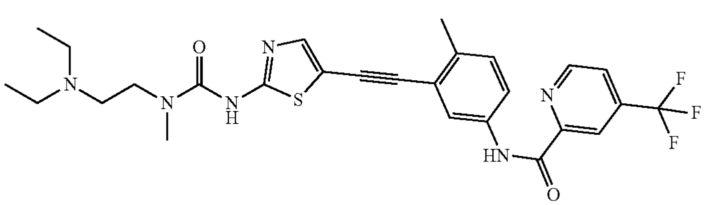 [SMILES: CCN(CC)CCN(C)C(=O)Nc1ncc(C#Cc2cc(NC(=O)c3cc(C(F)(F)F)ccn3)ccc2C)s1] | (CD$_3$OD): 8.98 (d, J = 5.02 Hz, 1H), 8.44-8.47 (m, 1H), 7.96 (s, 1H), 7.92 (d, J = 5.07 Hz, 1H), 7.69 (dd, J = 2.32, 8.22 Hz, 1H), 7.54 (s, 1H), 7.30 (d, J = 8.41 Hz, 1H), 3.57 (t, 2H), 3.05 (s, 3H), 2.72-2.85 (m, 6H), 2.47 (s, 3H), 1.17 (t, J = 7.22 Hz, 6H). | [M + H]$^+$ 559.2 |

TABLE 3-continued

| Cmpd No. | Compound Structure | ¹H NMR (400 MHz): δ (ppm) | ESI-MS m/z |
|---|---|---|---|
| I-60 | 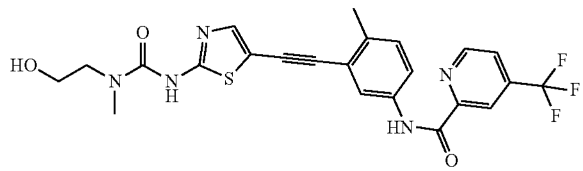 [SMILES: Cc1ccc(NC(=O)c2cc(C(F)(F)F)ccn2)cc1C#Cc1cnc(NC(=O)N(C)CCO)s1] | (DMSO-$d_6$): 10.96 (br d, J = 1.25 Hz, 1H), 10.85 (s, 1H), 9.05 (d, J = 5.02 Hz, 1H), 8.36 (s, 1H), 8.09 (s, 1H), 8.10 (d, J = 5.41 Hz, 2H), 7.82 (dd, J = 2.26, 8.28 Hz, 1H), 7.73 (s, 1H), 7.33 (d, J = 8.53 Hz, 1H), 3.52-3.62 (m, 2H), 3.50 (t, 2H), 3.28 (t, 1H), 3.02 (s, 3H), 2.41 (s, 3H). | [M + H]⁺ 504.1 |
| I-61 | 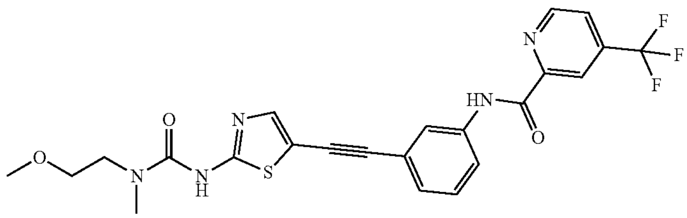 [SMILES: COCCN(C)C(=O)Nc1ncc(C#Cc2cccc(NC(=O)c3cc(C(F)(F)F)ccn3)c2)s1] | (DMSO-$d_6$): 10.99 (br s, 1H), 10.93 (s, 1H), 9.06 (d, J = 5.02 Hz, 1H), 8.36-8.38 (m, 1H), 8.10-8.16 (m, 2H), 7.93 (ddd, J = 1.00, 2.13, 8.28 Hz, 1H), 7.74 (s, 1H), 7.44 (t, J = 7.97 Hz, 1H), 7.31 (td, J = 1.19, 7.91 Hz, 1H), 3.42-3.63 (m, 4H), 3.29 (s, 3H), 3.01 (s, 3H). | [M + H]⁺ 504.1 |
| I-62 | 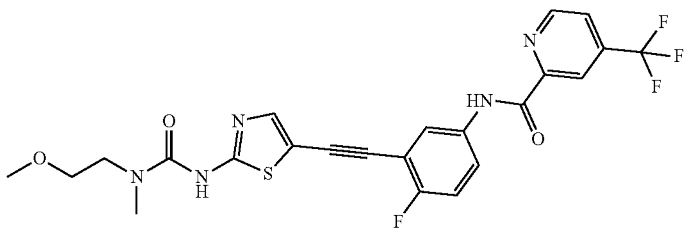 [SMILES: COCCN(C)C(=O)Nc1ncc(C#Cc2cc(NC(=O)c3cc(C(F)(F)F)ccn3)ccc2F)s1] | (CD₃OD): 8.98 (d, J = 5.02 Hz, 1H), 8.46 (s, 1H), 8.04 (dd, J = 2.70, 6.21 Hz, 1H), 7.93 (d, J = 5.06 Hz, 1H), 7.83 (ddd, J = 2.76, 4.52, 9.03 Hz, 1H), 7.60 (s, 1H), 7.22 (t, J = 9.03 Hz, 1H), 3.59-3.67 (m, 4H), 3.43 (s, 3H), 3.10 (s, 3H). | [M + H]⁺ 522.0 |

Biochemical Assays

Example 4: c-Kit Assay

Generation of Ba/F3 KIT Mutant Engineered Cell Lines

KIT cDNAs were synthesized by GenScript and cloned into the pLVX-IRES-Puro vector (Clontech). Viral particles were produced by transfecting pLVX-IRES-puro vectors containing KIT mutant genes into HEK293 cells (Invitrogen) using the Trans-Lentiviral ORF Packaging Kit (Thermo Scientific). 48 hours post-transfection, virus-containing supernatants were harvested and incubated for another 48-72 hours with parental Ba/F3 cells (DSMZ) in the presence of 10 ng/mL IL-3 (R&D Systems). Transduced Ba/F3 cells were then selected by IL-3 withdrawal and puromycin (0.5-1 μg/mL, Invitrogen).

Viability Assays

Cell lines (e.g., EX11DEL, EX11DEL/D816H, EX11DEL/T670I, and EX11DEL/V654A) were plated into 384 well plates using RPMI 1640 supplemented with 10% FBS at densities that produced linear growth and incubated at 37° C. in 5% (v/v) $CO_2$. Cells were treated with eight concentrations of compound over a 4-fold dilution (10 μM to 0.61 nM) and viability was assessed using Cell Titer-Glo assay (Promega) after 72 hours. Data were plotted as percent viability relative to vehicle-treated cells. Dose-responses curves were generated and used to calculate $IC_{50}$ values.

Table 4: c-Kit activity of compounds of the invention in the c-Kit assay. ++++ indicates an $IC_{50}$ of less than about 10 nM, +++ indicates an $IC_{50}$ between about 10 nM and about 50 nM, ++ indicates an $IC_{50}$ between about 50 nM and about 100 nM, and + indicates an $IC_{50}$ greater than about 100 nM and less than about 10 μM.

TABLE 4 cKit Assay.

| Cmpd No. | BAF3 FL KIT EX11DEL (nM) | BAF3 FL KIT EX11DEL/ D816H (nM) | BAF3 FL KIT EX11DEL/ T670I (nM) | BAF3 FL KIT EX11DEL/ V654A (nM) |
|---|---|---|---|---|
| I-1 | ++++ | ++++ | ++++ | ++++ |
| I-2 | ++++ | +++ | ++++ | ++++ |
| I-3 | ++++ | +++ | +++ | +++ |
| I-4 | ++++ | ++++ | ++++ | +++ |
| I-5 | ++++ | +++ | +++ | +++ |
| I-6 | ++++ | +++ | +++ | +++ |
| I-7 | ++++ | +++ | ++++ | +++ |
| I-8 | ++++ | ++++ | ++++ | +++ |
| I-9 | ++++ | +++ | ++++ | +++ |
| I-10 | ++++ | ++++ | ++++ | ++++ |
| I-11 | ++++ | +++ | +++ | +++ |
| I-12 | ++++ | +++ | ++ | ++ |
| I-13 | ++++ | +++ | +++ | +++ |
| I-14 | ++++ | +++ | +++ | +++ |
| I-15 | ++++ | +++ | +++ | +++ |
| I-16 | ++++ | +++ | ++++ | +++ |
| I-17 | ++++ | +++ | +++ | +++ |
| I-18 | ++++ | +++ | +++ | +++ |
| I-19 | ++++ | +++ | +++ | +++ |
| I-20 | ++++ | +++ | +++ | +++ |
| I-21 | ++++ | +++ | +++ | +++ |
| I-22 | ++++ | ++++ | ++++ | ++++ |
| I-23 | ++++ | +++ | ++++ | +++ |
| I-24 | ++++ | ++++ | ++++ | ++++ |
| I-25 | +++ | +++ | +++ | +++ |
| I-26 | +++ | +++ | +++ | +++ |
| I-27 | ++++ | +++ | ++++ | +++ |
| I-28 | ++++ | +++ | +++ | +++ |
| I-29 | ++++ | ++++ | ++++ | +++ |
| I-30 | ++++ | +++ | +++ | +++ |
| I-31 | +++ | ++ | +++ | ++ |
| I-32 | ++++ | +++ | +++ | +++ |

TABLE 4-continued cKit Assay.

| Cmpd No. | BAF3 FL KIT EX11DEL (nM) | BAF3 FL KIT EX11DEL/ D816H (nM) | BAF3 FL KIT EX11DEL/ T670I (nM) | BAF3 FL KIT EX11DEL/ V654A (nM) |
|---|---|---|---|---|
| I-33 | +++ | ++ | +++ | ++ |
| I-34 | ++++ | +++ | +++ | +++ |
| I-35 | ++++ | ++++ | ++++ | +++ |
| I-36 | ++++ | +++ | +++ | +++ |
| I-37 | ++++ | ++++ | ++++ | ++++ |
| I-38 | ++++ | ++ | ++ | ++ |
| I-39 | +++ | + | + | + |
| I-40 | ++++ | +++ | ++++ | +++ |
| I-41 | ++++ | +++ | +++ | +++ |
| I-42 | ++++ | + | + | + |
| I-43 | ++++ | + | + | + |
| I-44 | ++++ | +++ | ++++ | +++ |
| I-45 | ++++ | +++ | ++++ | +++ |
| I-46 | +++ | +++ | +++ | ++ |
| I-47 | ++++ | +++ | + | +++ |
| I-48 | ++++ | +++ | +++ | ++ |
| I-49 | ++++ | +++ | +++ | +++ |
| I-50 | +++ | +++ | +++ | + |
| I-51 | ++++ | +++ | +++ | +++ |
| I-52 | +++ | + | + | + |
| I-53 | +++ | ++ | +++ |  |
| I-54 | ++++ | +++ | +++ | +++ |
| I-55 | +++ | ++ | +++ |  |
| I-56 | ++++ | +++ | +++ | +++ |
| I-57 | ++++ | ++++ | +++ | ++++ |
| I-58 | ++++ | ++ | + | ++ |
| I-59 | +++ | ++ | + | + |
| I-60 | ++++ | +++ | ++ | +++ |
| I-61 | ++++ | +++ | +++ | +++ |
| I-62 | ++++ | +++ | ++++ | +++ |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of one of the following formulae (Ig) or (Ih):

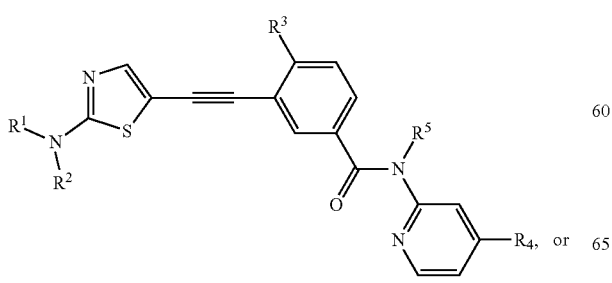

(Ig)

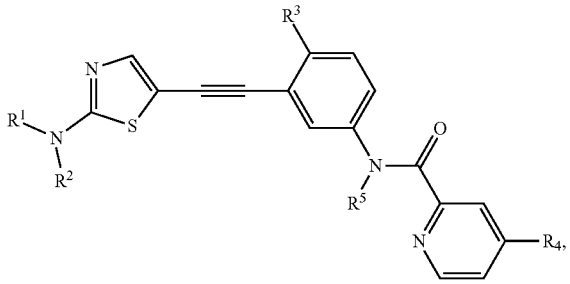

(Ih)

or a pharmaceutically acceptable salt thereof,
wherein:
$R^1$ is H, $(C_1-C_6)$ alkyl, —$(CH_2)C(O)OH$, or —$C(O)N(R^7)_2$;
$R^2$ is $(C_1-C_6)$ alkyl, —$C(O)R^8$, or —$C(O)NR^9R^{10}$;
each $R^3$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or OH;
each $R^4$ is independently at each occurrence $(C_1-C_6)$ alkyl, $(C_1-C_6)$ alkoxy, $(C_1-C_6)$ haloalkyl, $(C_1-C_6)$ haloalkoxy, halogen, —OH, CN, —$(C(R^6)_2)_p$-heterocycloalkyl wherein the heterocycloalkyl comprises a 4- to 7-membered ring and 1 to 3 heteroatoms selected from N, O, and S, or —$(C(R^6)_2)_p$-heteroaryl wherein the heteroaryl comprises a 5- or 6-membered ring and 1 to 3 heteroatoms selected from N, O, and S, and wherein the heterocycloalkyl or heteroaryl is optionally substituted with one or more substituents each independently selected from $(C_1-C_6)$ alkyl, —$NH_2$, $(C_1-C_6)$ alkylamino, and $(C_1-C_6)$ dialkylamino;
$R^5$ is H, $(C_1-C_6)$ alkyl, or $(C_1-C_6)$ haloalkyl;
each $R^6$ is independently H or $(C_1-C_6)$ alkyl;
each $R^7$ is independently H or $(C_1-C_6)$ alkyl;
$R^8$ is $(C_1-C_6)$ alkyl, $(C_3-C_7)$ cycloalkyl, $(C_2-C_6)$ alkenyl, $(C_1-C_3)$ alkoxy, $(C_1-C_6)$ haloalkyl, $(C_1-C_6)$ haloalkoxy, or 4 to 7-membered heterocycloalkyl comprising 1 to 3 heteroatoms selected from N, O, and S;
$R^9$ is H, $(C_1-C_6)$ alkyl, $(C_1-C_6)$ haloalkyl, $(C_3-C_7)$ cycloalkyl, or 4 to 7-membered heterocycloalkyl comprising 1 to 3 heteroatoms selected from N, O, or S;
$R^{10}$ is H, $(C_1-C_6)$ alkyl, $(C_1-C_6)$ haloalkyl, $(C_3-C_7)$ cycloalkyl, or 4 to 7-membered heterocycloalkyl comprising 1 to 3 heteroatoms selected from N, O, or S, wherein the cycloalkyl or heterocycloalkyl is optionally substituted with one or more substituents each independently selected from $(C_1-C_6)$ alkyl, —$NH_2$, $(C_1-C_6)$ alkylamino, $(C_1-C_6)$ dialkylamino, and —OH, and wherein the $(C_1-C_6)$ alkyl is optionally substituted with one or more $R^{11}$;
or $R^9$ and $R^{10}$ together with the nitrogen atom to which they are attached form a 4- to 7-membered heterocycloalkyl ring comprising 1 to 3 heteroatom selected from N, O, and S, optionally substituted with one or more substituent each independently selected from $(C_1-C_6)$ alkyl, $(C_1-C_6)$ hydroxyalkyl, —$(CH_2)_q$—$NH_2$, —$(CH_2)_q$—$(C_1-C_6)$ alkylamino, —$(CH_2)_q$—$(C_1-C_6)$ dialkylamino, —$C(O)(C_1-C_6)$ alkyl, —OH, and 4- to 7-membered heterocycloalkyl comprising 1 to 3 heteroatom selected from N, O, and S, and optionally substituted with one or more $(C_1-C_6)$ alkyl;
$R^{11}$ is $(C_1-C_6)$ alkoxy, —OH, —$NH_2$, $(C_1-C_6)$ alkylamino, $(C_1-C_6)$ dialkylamino, 5- or 6-membered heteroaryl comprising 1 to 3 heteroatoms selected from N, O, or S, or 4- to 7-membered heterocycloalkyl comprising 1 to 3 heteroatoms selected from N, O, or S, wherein the heterocycloalkyl is optionally substituted with one or more substituents each independently selected from $(C_1-C_6)$ alkyl and OH; and each p and q is independently 0, 1 or 2.

2. The compound of claim 1, wherein $R^5$ is H.

3. The compound of claim 1, wherein $R^4$ is $(C_1-C_6)$ haloalkyl.

4. The compound of claim 1, wherein $R^4$ is $CF_3$.

5. The compound of claim 1, wherein $R^3$ is methyl.

6. The compound of claim 1, wherein $R^1$ is H and $R^2$ is $-C(O)NR^9R^{10}$.

7. The compound of claim 6, wherein $R^9$ is $(C_1-C_6)$ alkyl and $R^{10}$ is $(C_1-C_6)$ alkyl substituted with one $R^{11}$.

8. The compound of claim 7, wherein R is —OH.

9. The compound of claim 6, wherein $R^9$ and $R^{10}$ together with the nitrogen atom to which they are attached form a 4- to 6-membered heterocycloalkyl ring comprising 1 to 3 heteroatom selected from N, O, and S, optionally substituted with one or more substituents each independently selected from $(C_1-C_6)$ alkyl, $(C_1-C_6)$ hydroxyalkyl, $-(CH_2)_q-(C_1-C_6)$ dialkylamino, $-C(O)(C_1-C_6)$ alkyl, OH, or 6-membered heterocycloalkyl comprising 1 to 3 heteroatom selected from N, O, and S, and optionally substituted with $(C_1-C_6)$ alkyl.

10. A compound selected from:
3-((2-(3,3-dimethylureido)thiazol-5-yl)ethynyl)-4-methyl-N-(4-(trifluoromethyl)pyridin-2-yl)benzamide (I-1);
4-methyl-N-(4-(trifluoromethyl)pyridin-2-yl)-3-((2-ureidothiazol-5-yl)ethynyl)benzamide (I-2);
methyl (5-((2-methyl-5-((4-(trifluoromethyl)pyridin-2-yl)carbamoyl)phenyl)ethynyl)thiazol-2-yl)carbamate (I-3);
4-methyl-3-((2-(3-methylureido)thiazol-5-yl)ethynyl)-N-(4-(trifluoromethyl)pyridin-2-yl)benzamide (I-4);
3-((2-(3-(2-methoxyethyl)ureido)thiazol-5-yl)ethynyl)-4-methyl-N-(4-(trifluoromethyl)pyridin-2-yl)benzamide (I-5);
4-methyl-3-((2-(3-(2-morpholinoethyl)ureido)thiazol-5-yl)ethynyl)-N-(4-(trifluoromethyl)pyridin-2-yl)benzamide (I-6);
3-((2-(3-(2-methoxyethyl)-3-methylureido)thiazol-5-yl)ethynyl)-4-methyl-N-(4-(trifluoromethyl)pyridin-2-yl)benzamide (I-7);
3-((2-(3-ethyl-3-methylureido)thiazol-5-yl)ethynyl)-4-methyl-N-(4-(trifluoromethyl)pyridin-2-yl)benzamide (I-8);
3-((2-(3-(2-(dimethylamino)ethyl)-3-methylureido)thiazol-5-yl)ethynyl)-4-methyl-N-(4-(trifluoromethyl)pyridin-2-yl)benzamide (I-9);
3-((2-(3-(2-hydroxyethyl)-3-methylureido)thiazol-5-yl)ethynyl)-4-methyl-N-(4-(trifluoromethyl)pyridin-2-yl)benzamide (I-10);
3-((2-(3-(2-(dimethylamino)ethyl)ureido)thiazol-5-yl)ethynyl)-4-methyl-N-(4-(trifluoromethyl)pyridin-2-yl)benzamide (I-11);
4-methyl-3-((2-(3-(2-(pyrrolidin-1-yl)ethyl)ureido)thiazol-5-yl)ethynyl)-N-(4-(trifluoromethyl)pyridin-2-yl)benzamide (I-12);
4-methyl-3-((2-(3-((1-methylpiperidin-4-yl)methyl)ureido)thiazol-5-yl)ethynyl)-N-(4-(trifluoromethyl)pyridin-2-yl)benzamide (I-13);
4-methyl-3-((2-(3-(2-(4-methylpiperazin-1-yl)ethyl)ureido)thiazol-5-yl)ethynyl)-N-(4-(trifluoromethyl)pyridin-2-yl)benzamide (I-14);
3-((2-(3-(2-hydroxy-2-methylpropyl)ureido)thiazol-5-yl)ethynyl)-4-methyl-N-(4-(trifluoromethyl)pyridin-2-yl)benzamide (I-15);
4-methyl-3-((2-(3-methyl-3-(2-(4-methylpiperazin-1-yl)ethyl)ureido)thiazol-5-yl)ethynyl)-N-(4-(trifluoromethyl)pyridin-2-yl)benzamide (I-16);
3-((2-(3-cyclopropylureido)thiazol-5-yl)ethynyl)-4-methyl-N-(4-(trifluoromethyl)pyridin-2-yl)benzamide (I-17);
3-((2-(3-(2-(3-hydroxypyrrolidin-1-yl)ethyl)ureido)thiazol-5-yl)ethynyl)-4-methyl-N-(4-(trifluoromethyl)pyridin-2-yl)benzamide (I-18);
4-methyl-3-((2-(3-methyl-3-(2-(pyrrolidin-1-yl)ethyl)ureido)thiazol-5-yl)ethynyl)-N-(4-(trifluoromethyl)pyridin-2-yl)benzamide (I-19);
4-methyl-3-((2-(3-methyl-3-((1-methylpyrrolidin-2-yl)methyl)ureido)thiazol-5-yl)ethynyl)-N-(4-(trifluoromethyl)pyridin-2-yl)benzamide (I-20);
3-((2-(3-(2-hydroxy-2-methylpropyl)-3-methylureido)thiazol-5-yl)ethynyl)-4-methyl-N-(4-(trifluoromethyl)pyridin-2-yl)benzamide (I-21);
3-((2-(3-(4-hydroxycyclohexyl)-3-methylureido)thiazol-5-yl)ethynyl)-4-methyl-N-(4-(trifluoromethyl)pyridin-2-yl)benzamide (I-22);
4-methyl-N-(5-((2-methyl-5-((4-(trifluoromethyl)pyridin-2-yl)carbamoyl)phenyl)ethynyl)thiazol-2-yl)piperazine-1-carboxamide (I-23);
3-hydroxy-3-methyl-N-(5-((2-methyl-5-((4-(trifluoromethyl)pyridin-2-yl)carbamoyl)phenyl)ethynyl)thiazol-2-yl)azetidine-1-carboxamide (I-24);
4-methyl-N-(5-((2-methyl-5-((4-(trifluoromethyl)pyridin-2-yl)carbamoyl)phenyl)ethynyl)thiazol-2-yl)piperidine-1-carboxamide (I-25);
4-methyl-3-((2-(3-(pyridin-4-ylmethyl)ureido)thiazol-5-yl)ethynyl)-N-(4-(trifluoromethyl)pyridin-2-yl)benzamide (I-26);
4-(2-hydroxyethyl)-N-(5-((2-methyl-5-((4-(trifluoromethyl)pyridin-2-yl)carbamoyl)phenyl)ethynyl)thiazol-2-yl)piperazine-1-carboxamide (I-27);
4-methyl-3-((2-(3-methyl-3-(2-(methylamino)ethyl)ureido)thiazol-5-yl)ethynyl)-N-(4-(trifluoromethyl)pyridin-2-yl)benzamide (I-28);
4-methyl-3-((2-(3-methyl-3-(1-methylpiperidin-4-yl)ureido)thiazol-5-yl)ethynyl)-N-(4-(trifluoromethyl)pyridin-2-yl)benzamide (I-29);
N-(5-((2-methyl-5-((4-(trifluoromethyl)pyridin-2-yl)carbamoyl)phenyl)ethynyl)thiazol-2-yl)piperazine-1-carboxamide (I-30);
3-((2-(3-(4-aminobutyl)ureido)thiazol-5-yl)ethynyl)-4-methyl-N-(4-(trifluoromethyl)pyridin-2-yl)benzamide (I-31);
4-methyl-3-((2-(3-methyl-3-(1-methylpiperidin-3-yl)ureido)thiazol-5-yl)ethynyl)-N-(4-(trifluoromethyl)pyridin-2-yl)benzamide (I-32);
3-((2-(3-(4-aminocyclohexyl)-3-methylureido)thiazol-5-yl)ethynyl)-4-methyl-N-(4-(trifluoromethyl)pyridin-2-yl)benzamide (I-33);
2-((dimethylamino)methyl)-N-(5-((2-methyl-5-((4-(trifluoromethyl)pyridin-2-yl)carbamoyl)phenyl)ethynyl)thiazol-2-yl)morpholine-4-carboxamide (I-34);
N-(5-((2-methyl-5-((4-(trifluoromethyl)pyridin-2-yl)carbamoyl)phenyl)ethynyl)thiazol-2-yl)morpholine-4-carboxamide (I-35);

3-((2-(3-(3-aminopropyl)ureido)thiazol-5-yl)ethynyl)-4-methyl-N-(4-(trifluoromethyl)pyridin-2-yl)benzamide (I-36);

4-acetyl-N-(5-((2-methyl-5-((4-(trifluoromethyl)pyridin-2-yl)carbamoyl)phenyl)ethynyl)thiazol-2-yl)piperazine-1-carboxamide (I-37);

3-((2-(3-(2-aminoethyl)ureido)thiazol-5-yl)ethynyl)-4-methyl-N-(4-(trifluoromethyl)pyridin-2-yl)benzamide (I-38);

4-methyl-3-((2-(3-methyl-3-(1-methylazetidin-3-yl)ureido)thiazol-5-yl)ethynyl)-N-(4-(trifluoromethyl)pyridin-2-yl)benzamide (I-39);

3-(dimethylamino)-N-(5-((2-methyl-5-((4-(trifluoromethyl)pyridin-2-yl)carbamoyl)phenyl)ethynyl)thiazol-2-yl)pyrrolidine-1-carboxamide (I-40);

N-(5-((2-methyl-5-((4-(trifluoromethyl)pyridin-2-yl)carbamoyl)phenyl)ethynyl)thiazol-2-yl)-4-(4-methylpiperazin-1-yl)piperidine-1-carboxamide (I-41);

2-fluoro-5-((2-(3-methylureido)thiazol-5-yl)ethynyl)-N-(4-(trifluoromethyl)pyridin-2-yl)benzamide (I-42);

2-fluoro-N-(4-(trifluoromethyl)pyridin-2-yl)-5-((2-ureidothiazol-5-yl)ethynyl)benzamide (I-43);

3-((2-(3-methylureido)thiazol-5-yl)ethynyl)-N-(4-(trifluoromethyl)pyridin-2-yl)benzamide (I-44);

4-fluoro-3-((2-(3-methylureido)thiazol-5-yl)ethynyl)-N-(4-(trifluoromethyl)pyridin-2-yl)benzamide (I-45);

3-((2-(3-(2-methoxyethyl)-3-methylureido)thiazol-5-yl)ethynyl)-4-methyl-N-(4-(pyrrolidin-1-ylmethyl)-3-(trifluoromethyl)phenyl)benzamide (I-46);

N-(2-methoxy-3-(trifluoromethyl)phenyl)-3-((2-(3-(2-methoxyethyl)-3-methylureido)thiazol-5-yl)ethynyl)-4-methylbenzamide (I-47);

N-(4-cyano-3-(trifluoromethyl)phenyl)-3-((2-(3-(2-methoxyethyl)-3-methylureido)thiazol-5-yl)ethynyl)-4-methylbenzamide (I-48);

3-((2-(cyclopropanecarboxamido)thiazol-5-yl)ethynyl)-4-methyl-N-(4-(trifluoromethyl)pyridin-2-yl)benzamide (I-49);

3-((2-(cyclopropanecarboxamido)thiazol-5-yl)ethynyl)-4-methyl-N-(4-((4-methylpiperazin-1-yl)methyl)-3-(trifluoromethyl)phenyl)benzamide (I-50);

3-((2-acetamidothiazol-5-yl)ethynyl)-4-methyl-N-(4-(trifluoromethyl)pyridin-2-yl)benzamide (I 51);

4-methyl-3-((2-pivalamidothiazol-5-yl)ethynyl)-N-(4-(trifluoromethyl)pyridin-2-yl)benzamide (I-52);

N-(4-methyl-3-((2-(3-methyl-3-(1-methylpiperidin-4-yl)ureido)thiazol-5-yl)ethynyl)phenyl)-4-(trifluoromethyl)picolinamide (I-53);

N-(3-((2-(3-(2-methoxyethyl)-3-methylureido)thiazol-5-yl)ethynyl)-4-methylphenyl)-4-(trifluoromethyl)picolinamide (I-54);

N-(4-methyl-3-((2-(3-methyl-3-(2-(4-methylpiperazin-1-yl)ethyl)ureido)thiazol-5-yl)ethynyl)phenyl)-4-(trifluoromethyl)picolinamide (I-55);

N-(3-((2-(3,3-dimethylureido)thiazol-5-yl)ethynyl)-4-methylphenyl)-3-(trifluoromethoxy)benzamide (I-56);

N-(4-methyl-3-((2-(3-methylureido)thiazol-5-yl)ethynyl)phenyl)-4-(trifluoromethyl)picolinamide (I-57);

N-(3-((2-(3-(2-(dimethylamino)ethyl)-3-methylureido)thiazol-5-yl)ethynyl)-4-methylphenyl)-4-(trifluoromethyl)picolinamide (I-58);

N-(3-((2-(3-(2-(diethylamino)ethyl)-3-methylureido)thiazol-5-yl)ethynyl)-4-methylphenyl)-4-(trifluoromethyl)picolinamide (I-59);

N-(3-((2-(3-(2-hydroxyethyl)-3-methylureido)thiazol-5-yl)ethynyl)-4-methylphenyl)-4-(trifluoromethyl)picolinamide (I-60);

N-(3-((2-(3-(2-methoxyethyl)-3-methylureido)thiazol-5-yl)ethynyl)phenyl)-4-(trifluoromethyl)picolinamide (I-61); and N-(4-fluoro-3-((2-(3-(2-methoxyethyl)-3-methylureido)thiazol-5-yl)ethynyl)phenyl)-4-(trifluoromethyl)picolinamide (I-62), or a pharmaceutically acceptable salt thereof.

11. A pharmaceutical composition comprising a compound of claim claim 1, or a pharmaceutically acceptable salt thereof, and a pharmaceutically acceptable diluent, excipient or carrier.

12. The compound of claim 9, wherein $R^9$ and $R^{10}$ together with the nitrogen atom to which they are attached form a heterocycloalkyl ring that is azetidinyl, morpholinyl, piperidinyl, or piperazinyl, and which is optionally substituted with one or more substituent each independently selected from $(C_1-C_6)$ alkyl, $(C_1-C_6)$ hydroxyalkyl, —$(CH_2)_q$—$(C_1-C_6)$ dialkylamino, —$C(O)(C_1-C_6)$ alkyl, —OH, and 4- to 7-membered heterocycloalkyl comprising 1 to 3 heteroatom selected from N, O, and S, and optionally substituted with one or more $(C_1-C_6)$ alkyl.

13. The compound of claim 12, wherein said heterocycloalkyl ring is substituted with one substituent that is $(C_1-C_6)$ alkyl, $(C_1-C_6)$ hydroxyalkyl, —$(CH_2)_q$—$(C_1-C_6)$ dialkylamino, —$C(O)(C_1-C_6)$ alkyl, —OH, and 4- to 7-membered heterocycloalkyl comprising 1 to 3 heteroatom selected from N, O, and S, and optionally substituted with one or more $(C_1-C_6)$ alkyl.

14. The compound of claim 12, wherein said heterocycloalkyl ring is substituted with one substituent that is $(C_1-C_6)$ alkyl, $(C_1-C_6)$ hydroxyalkyl, —$(CH_2)_q$—$(C_1-C_6)$ dialkylamino, —$C(O)(C_1-C_6)$ alkyl, or —OH.

* * * * *